United States Patent
Black et al.

(10) Patent No.: US 10,590,143 B2
(45) Date of Patent: Mar. 17, 2020

(54) HERBICIDALLY ACTIVE (ALKYNYL-PHENYL)-SUBSTITUTED CYCLIC DIONE COMPOUNDS AND DERIVATIVES THEREOF

(71) Applicant: Syngenta Limited, Guildford, Surrey (GB)

(72) Inventors: Janice Black, Bracknell Berkshire (GB); James Nicholas Scutt, Bracknell Berkshire (GB); Louisa Whalley, Bracknell Berkshire (GB); Nigel James Willets, Bracknell Berkshire (GB)

(73) Assignee: Syngenta Limited, Guildford, Surrey (GB)

( * ) Notice: Subject to any disclaimer, the term of this patent is extended or adjusted under 35 U.S.C. 154(b) by 632 days.

(21) Appl. No.: 14/894,842

(22) PCT Filed: May 29, 2014

(86) PCT No.: PCT/EP2014/061207
§ 371 (c)(1),
(2) Date: Nov. 30, 2015

(87) PCT Pub. No.: WO2014/191535
PCT Pub. Date: Dec. 4, 2014

(65) Prior Publication Data
US 2016/0143277 A1    May 26, 2016

(30) Foreign Application Priority Data

May 30, 2013  (GB) .................................. 1309679.7
Dec. 23, 2013 (GB) .................................. 1322855.6

(51) Int. Cl.
| | | |
|---|---|---|
| *C07C 49/587* | (2006.01) | |
| *A01N 35/06* | (2006.01) | |
| *C07D 493/08* | (2006.01) | |
| *A01N 43/16* | (2006.01) | |
| *C07D 309/32* | (2006.01) | |
| *C07D 311/96* | (2006.01) | |
| *A01N 37/02* | (2006.01) | |
| *A01N 37/10* | (2006.01) | |
| *A01N 47/06* | (2006.01) | |
| *C07C 49/577* | (2006.01) | |
| *C07C 69/24* | (2006.01) | |
| *C07C 69/78* | (2006.01) | |
| *C07C 69/96* | (2006.01) | |

(Continued)

(52) U.S. Cl.
CPC .......... *C07D 493/08* (2013.01); *A01N 35/06* (2013.01); *A01N 37/02* (2013.01); *A01N 37/10* (2013.01); *A01N 43/16* (2013.01); *A01N 43/90* (2013.01); *A01N 47/06* (2013.01); *C07C 49/517* (2013.01); *C07C 49/577* (2013.01); *C07C 69/24* (2013.01); *C07C 69/78* (2013.01); *C07C 69/96* (2013.01); *C07C 381/14* (2013.01); *C07D 309/32* (2013.01); *C07D 311/96* (2013.01)

(58) Field of Classification Search
None
See application file for complete search history.

(56) References Cited

U.S. PATENT DOCUMENTS

2005/0054535 A1    3/2005  Fischer et al.

FOREIGN PATENT DOCUMENTS

| PG | 2011073060 A2 | 6/2011 |
|---|---|---|
| WO | 2008110307 A1 | 9/2008 |

(Continued)

OTHER PUBLICATIONS

International Search Report of International Application PCT/EP2014/061207, dated Sep. 9, 2015.

*Primary Examiner* — Sue X Liu
*Assistant Examiner* — Frank Choi
(74) *Attorney, Agent, or Firm* — Baker & Hostetler, LLP; Toni-Junell Herbert

(57) ABSTRACT

The present invention relates to a compound of formula (I): wherein: X is methyl or chlorine; $R^1$ is fluorine or bromine; $R^2$ is ethynyl, $C_1$-$C_3$alkoxy, $C_1$-$C_3$haloalkoxy, or $C_1$-$C_3$alkoxy-$C_1$-$C_3$alkoxy-; and Q is a pyran-3,5-dione-4-yl, a thiopyran-3,5-dione-4-yl, a piperidine-3,5-dione-4-yl, a cyclohexane-1,3,5-trione-2-yl, a cyclohexane-1,3-dione-2-yl, a cycloheptane-1,3-dione-2-yl, in which each cyclic dione is bridged by alkanediyl, or a derivative thereof (e.g. an enol ketone tautomer derivative thereof), wherein Q is further defined herein; and wherein the compound of formula (I) is optionally present as an agrochemically acceptable salt thereof. Preferably, X is methyl; and/or $R^1$ is fluorine; and/or $R^2$ is —O—$R^{2A}$, wherein $R^{2A}$ is methyl, ethyl, trifluoromethyl, difluoromethyl, trifluoroethyl, or —$CH_2CH_2OCH_3$. These compounds are suitable for use as herbicides. The invention therefore also relates to a method of controlling weeds, especially grassy monocotyledonous weeds, in crops of useful plants, comprising applying a compound of formula (I), or a herbicidal composition comprising such a compound, to the weeds and/or to the plants and/or to the locus thereof.

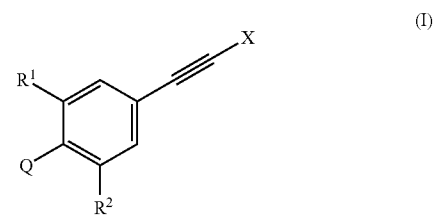

(I)

22 Claims, No Drawings

(51) Int. Cl.
*C07C 381/14* (2006.01)
*A01N 43/90* (2006.01)
*C07C 49/517* (2006.01)

(56) References Cited

FOREIGN PATENT DOCUMENTS

| | | | |
|---|---|---|---|
| WO | 2008145336 | A1 | 12/2008 |
| WO | 2009019015 | A1 | 2/2009 |
| WO | 2010081689 | A2 | 7/2010 |
| WO | 2013079708 | A1 | 6/2013 |

HERBICIDALLY ACTIVE (ALKYNYL-PHENYL)-SUBSTITUTED CYCLIC DIONE COMPOUNDS AND DERIVATIVES THEREOF

RELATED APPLICATION INFORMATION

This application is a 371 of International Application No. PCT/EP2014/061207, filed May 29, 2014, which claims priority to 1309679.7 filed May 30, 2013, and 1322855.6 filed Dec. 23, 2013, the contents of which are incorporated herein by reference herein.

The present invention relates to herbicidally active (alkynyl-phenyl)-substituted cyclic dione compounds, in particular pyrandione, thiopyrandione, piperidinedione, cyclohexanedione, cyclohexanetrione or cycloheptanedione compounds, more particularly (alkynyl-phenyl)-substituted and alkanediyl-bridged cyclic dione compounds such as pyrandione, thiopyrandione, piperidinedione, cyclohexanedione, cyclohexanetrione or cycloheptanedione compounds, and derivatives thereof (e.g. enol ketone tautomer derivatives thereof and/or fused and/or bicyclic derivatives thereof as appropriate), to processes for their preparation, to herbicidal compositions comprising those compounds, and to their use in controlling weeds such as grassy monocotyledonous weeds, especially in crops of useful plants, or in inhibiting undesired plant growth.

WO 01/17972 A2 (Syngenta Participations AG) discloses (4-methyl-phenyl)-substituted (such as 4-methyl-2,6-diethyl-phenyl-substituted) carbocycles or heterocycles, in particular carbocyclic or heterocyclic diones, suitable for use as herbicides. Amongst many compounds specifically disclosed in WO 01/17972 A2 is compound 21.115

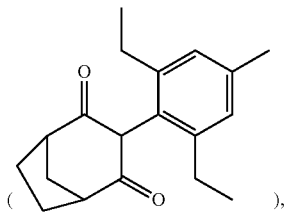 [SMILES: CCc1cc(C)cc(CC)c1C1C(=O)C2CCC(C2)C1=O]

which is disclosed on page 105 of WO 01/17972 A2.

WO 03/013249 A1 (Bayer AG) and its equivalent US 2005/0054535 A1 disclose selective herbicidal compositions comprising (a) a (substituted-phenyl)-substituted cyclic ketoenol and (b) a compound which improves crop plant compatibility, in particular cloquintocet-mexyl or mefenpyr-diethyl. In WO 03/013249 A1 and US 2005/0054535 A1, the cyclic ketoenol (whose tautomer is a cyclic dione) can in particular be a 3-(substituted-phenyl)-pyrrolidine-2,4-dione, a 3-(substituted-phenyl)-tetrahydrofuran-2,4-dione, a 3-(substituted-phenyl)-pyran-2,4-dione derivative, a 2-(substituted-phenyl)-cyclopentane-1,3-dione, or a 2-(substituted-phenyl)-cyclohexane-1,3-dione, et al., or a derivative (e.g. ester or carbonate derivative) of these cyclic ketoenols/cyclic diones.

WO 2007/068427 A2 (Bayer CropScience AG) and its equivalent US 2009/0227563 A1 disclose a composition comprising (a) a (substituted-phenyl)-substituted cyclic ketoenol as a herbicide, and (b) an ammonium and/or phosphonium salt to boost activity. In WO 2007/068427 A2 and US 2009/0227563 A1, the cyclic ketoenol (whose tautomer is a cyclic dione) can in particular be a 3-(substituted-phenyl)-pyrrolidine-2,4-dione, a 3-(substituted-phenyl)-tetrahydrofuran-2,4-dione, a 3-(substituted-phenyl)-pyran-2,4-dione derivative, a 2-(substituted-phenyl)-cyclopentane-1,3-dione, or a 2-(substituted-phenyl)-cyclohexane-1,3-dione, a 4-(substituted-phenyl)-pyrazolidine-3,5-dione, et al., or a derivative (e.g. ester or carbonate derivative) of these cyclic ketoenols/cyclic diones.

WO 2008/071405 A1 and WO 2009/074314 A1 (both Syngenta Limited and Syngenta Participations AG) each disclose herbicidally active pyran-3,5-diones, thiopyran-3,5-diones and cyclohexane-1,3,5-triones, each substituted at the 4-position of the cyclic dione or trione by an aryl-substituted-phenyl or by a heteroaryl-substituted-phenyl.

WO 2010/081755 A1 and WO 2010/089211 A1 (both Syngenta Limited) each disclose herbicidally active pyran-3,5-diones, thiopyran-3,5-diones, cyclohexanediones, cycloheptanediones and cyclohexanetriones, each substituted by an aryloxy-substituted-phenyl or by a heteroaryloxy-substituted-phenyl.

WO 2008/110308 A1 (Syngenta Participations AG) discloses 2-(substituted-phenyl)-cyclohexane-1,3-dione compounds and derivatives, containing a $R^8$—X—$(CR^6R^7)_n$— substituent (wherein X is O, S, S(O) or S(O)$_2$), which can e.g. be a heteroatom-X-containing-spirocyle, at the 5-position of the cyclohexane-1,3-dione, and having herbicidal properties. WO 2010/081689 A2 (Bayer CropScience AG) discloses the use of 2-(substituted-phenyl)-5-[$R^8$—X—$(CR^6R^7)_n$—]-cyclohexane-1,3-dione compounds or derivatives (i.e. compounds substantially as disclosed in WO 2008/110308) as insecticides and/or acaricides and/or fungicides.

WO 2008/110307 A1 (Syngenta Participations AG) discloses 2-(substituted-phenyl)-5-(carbon-linked-heterocyclyl)-cyclohexane-1,3-dione compounds and derivatives, and their use as herbicides. WO 2010/081687 A1 (Bayer CropScience AG) discloses the use of 2-(substituted-phenyl)-5-(carbon-linked-heterocyclyl)-cyclohexane-1,3-dione compounds or derivatives (i.e. compounds substantially as disclosed in WO 2008/110307) as insecticides and/or acaricides and/or fungicides.

WO 2010/046194 A1 (Syngenta Limited) discloses 2-(substituted-phenyl)-cyclohexane-1,3-dione compounds and derivatives, containing a Q-$CR^6R^7$— substituent at the 5-position of the cyclohexane-1,3-dione (wherein Q is a saturated or mono-unsaturated heterocycle), and having herbicidal properties.

WO 2008/145336 A1 and A8 (Syngenta Limited) disclose herbicidally active phenyl-substituted bicyclic (carbon-bridged, e.g. alkanediyl-bridged) 1,3-dione compounds, such as 3-(substituted-phenyl)bicyclo[3.2.1]octane-2,4-diones.

Cyclopentane-1,3-dione compounds substituted at the 2-position by substituted-phenyl and having herbicidal activity are described, for example, in WO 2010/000773 A1, WO 2010/069834 A1, WO 2010/089210 A1, WO 2010/102848 A1 and WO 2011/007146 A1 (all Syngenta Limited et al.). For example, WO 2010/000773 A1 (Syngenta Limited) discloses 5-(heterocyclylalkyl)-3-hydroxy-2-phenylcyclopent-2-en-1-one compounds and certain derivatives thereof as herbicides. WO 2011/073060 A2 (Syngenta Participations AG) discloses a method of combating and controlling insects, acarines, nematodes or moluscs comprising applying a WO 2010/000773 A1 compound. Also, for example, WO 2010/069834 A1 (Syngenta Limited) discloses cyclopentane-1,3-diones having both heteroarylmethyl- and 2-(substituted-phenyl)-substituents on the cyclopentane ring, and derivatives thereof containing latentiating groups; these compounds are disclosed as having herbicidal properties. Fused bicyclic and oxygen-bridged cyclopentanedione derivatives, specifically 10-oxatricyclo-[5.2.1. $0^{2,6}$]decane-3,5-diones and derivatives, which are substituted by substituted-phenyl and which have herbicidal activity, are disclosed in WO 2009/019005 A2 and WO 2009/019015 A1 (both Syngenta Limited). Phenyl-substituted bicyclooctane-1,3-dione derivatives, and their use as pesticides and/or herbicides, are disclosed in WO 2010/040460 A2 (Bayer Cropscience AG).

Copending PCT application PCT/EP2012/074118, filed on 30 Nov. 2012 and published on 6 Jun. 2013 as WO 2013/079672 A1 (Syngenta Limited and Syngenta Participations AG) discloses that certain substituted spiroheterocyclic pyrrolidine dione compounds, having an alkynyl-phenyl-headgroup, have herbicidal properties.

Copending PCT application PCT/EP2012/074172, filed on 30 Nov. 2012 and published on 6 Jun. 2013 as WO 2013/079708 A1 (Syngenta Limited and Syngenta Participations AG) discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl and at the 2-position by (specifically) either methyl or chlorine, and derivatives of the enol ketone tautomer of such cyclopentanediones, which have herbicidal activity and/or plant-growth-inhibiting properties, especially in the control of grassy monocotyledonous weeds and/or when used post-emergence.

Alkanediyl-bridged cyclic 1,3-dione compounds (wherein one carbonyl ring-carbon is defined as being the 1-position of the cycle/ring) and derivatives (e.g. spirocyclic bicyclic derivatives) thereof, which are substituted at the 2-position of the cyclic 1,3-dione by a phenyl which itself is substituted at the 4-position by (specifically) either prop-1-ynyl or chloroethynyl and at the 2-position by (specifically) either fluorine or bromine, and derivatives of the enol ketone tautomer of such cyclic 1,3-diones, which have herbicidal activity and/or plant-growth-inhibiting properties, especially in the control of grassy monocotyledonous weeds and/or when used post-emergence, have now been found, which are encompassed by the present invention.

The present invention is based on the finding that cyclic diones of the general formula (I)

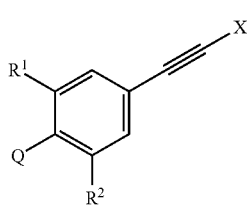

wherein:
X is methyl or chlorine (preferably methyl);
$R^1$ is fluorine or bromine (preferably fluorine);
$R^2$ is ethynyl, $C_1$-$C_3$alkoxy-, $C_1$-$C_3$haloalkoxy-, or $C_1$-$C_3$alkoxy-$C_1$-$C_3$alkoxy- (preferably —O—$R^{2A}$, wherein $R^{2A}$ is methyl, ethyl, trifluoromethyl, difluoromethyl, trifluoroethyl, or —CH$_2$CH$_2$OCH$_3$; more preferably —O—$R^{2A}$, wherein $R^{2A}$ is methyl, ethyl, trifluoromethyl or difluoromethyl); and Q is a pyran-3,5-dione-4-yl, a thiopyran-3,5-dione-4-yl, a piperidine-3,5-dione-4-yl, a cyclohexane-1,3,5-trione-2-yl, a cyclohexane-1,3-dione-2-yl, or a cycloheptane-1,3-dione-2-yl, in which each cyclic dione is bridged by alkanediyl, as well as derivatives thereof (e.g. spirocyclic derivatives, and/or enol ketone tautomer derivatives thereof), in particular wherein Q is as further defined herein, are novel;

and that the exemplified compounds A1, A2, A3, A4, A5, A6, A7, A8, P1, P2, P3, P4 and P5 within this formula (I) and disclosed herein appear to be potent post-emergent herbicides when used against grassy (in particular warm climate grassy) monocotyledonous weeds, when applied at about 250 and/or 30 g/ha post-emergence (e.g. as shown in Biological Examples 1 and 2 hereinafter), or, for exemplified compounds A1, A3, A4, A7, P1, P2 and P4, when applied at 8 g/ha post-emergence with certain adjuvant systems (e.g. see Biological Example 3).

In particular, the results in Biological Example 1A hereinafter appear to show that Compound A1, within the present formula (I), having a 2-fluoro-6-methoxy-4-(prop-1-ynyl)-phenyl moiety attached to a bicyclo[3.2.1]octane-2,4-dione, is a more potent herbicide against the grassy monocotyledonous weeds ALOMY (*Alopecurus myosuroides*) and ECHCG (*Echinochloa crus-galli*) than compound B1, having a 2-fluoro-6-methoxy-4-ethynyl-phenyl moiety attached to the same bicyclo[3.2.1]octane-2,4-dione, when applied post-emergence at 30 and 8 g/ha under the conditions stated in Biological Example 1A.

Also, in particular, Compound A1

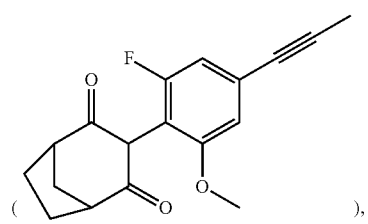 [SMILES: CC#Cc1cc(F)c(C2C(=O)C3CCC(C3)C2=O)c(OC)c1]

within the presently invented formula (I), appears at first sight to have higher post-emergence activities at 30 g/ha against the grassy monocotyledonous weeds LOLPE (*Lolium perenne*), POAAN (*Poa annua*), BROTE (*Bromus tectorum*) and SORVU (*Sorghum bicolor* (L.) *Moench* ssp. Bicolor, or *Sorghum vulgare* Pers.), than those of comparator compound X10

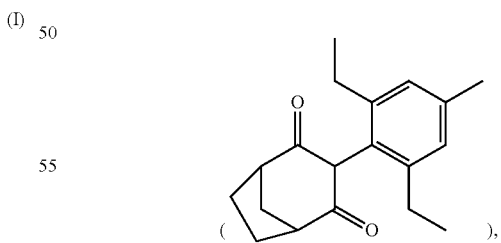

disclosed as compound 21.115 on page 105 of WO 01/17972 A2 (see Biological Example 2 hereinafter, and the notes at the end of its post-emergence herbicidal activity results table).

Also, the exemplified compounds A1, A2, A7, P1, P2, P3, P4 and P5 within the present formula (I), e.g. when applied at 30 g/ha post-emergence appear to exhibit a low or reasonably low phytotoxicity against certain docotyledonous crops, in particular soybean and/or sugarbeet (e.g. see Biological Example 2 hereinafter); see also Biological Example 3 for the low phytotoxicity of certain exemplified compounds including A1, A3, A4, A7, P1, P2 and P4 on soybean. Finally, compounds A1, A2, A7, P1 and P5 within the present formula (I) appear to exhibit a medium or reasonably low phytotoxicity against wheat relative to their (generally higher) herbicidal activity (phytotoxicity) against warm-climate grassy monocotyledonous weeds, e.g. when applied post-emergence (e.g. see Biological Example 2 hereinafter).

Thus, in a first aspect of the invention, there is provided a compound of formula (I)

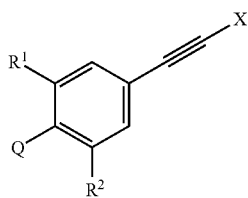

(I)

wherein:
X is methyl or chlorine;
$R^1$ is fluorine or bromine;
$R^2$ is ethynyl, $C_1$-$C_3$alkoxy-, $C_1$-$C_3$haloalkoxy- (in particular $C_1$-$C_3$fluoroalkoxy-), or $C_1$-$C_3$alkoxy-$C_1$-$C_3$alkoxy-;
and Q is a group of formula Q2:

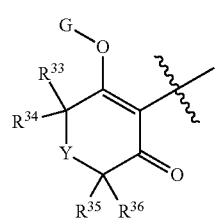

(Q2)

wherein in Q2:
$R^{33}$ and $R^{36}$, independently of each other, are hydrogen, $C_1$-$C_5$alkyl (in particular $C_1$-$C_4$alkyl, e.g. $C_1$-$C_2$alkyl), $C_2$-$C_4$ alkenyl (in particular $C_2$-$C_3$alkenyl-$CH_2$—, e.g. ethenyl-$CH_2$—), $C_2$-$C_4$ alkynyl (in particular $C_2$-$C_3$alkynyl-$CH_2$—, e.g. ethynyl-$CH_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, said heterocyclyl being attached at a ring carbon atom within the heterocyclyl (in particular tetrahydrofuranyl such as tetrahydrofuran-3-yl, or tetrahydropyranyl such as tetrahydropyran-4-yl); provided that no more than one (in particular none) of $R^{33}$ and $R^{36}$ is alkenyl, alkynyl, alkoxyalkyl, alkylthioalkyl, alkylsulfinylalkyl, alkylsulfonylalkyl, cycloalkyl or heterocyclyl; and
$R^{34}$ and $R^{35}$ taken together are —$(CH_2)_{n34}$— or —$(CH_2)_{n35}$—$C(R^{37a})(R^{37b})$—$(CH_2)_{n36}$—;
wherein $R^{37a}$ is $C_1$-$C_2$alkyl; $R^{37b}$ is hydrogen or $C_1$-$C_2$alkyl;

n34 is 1, 2 or 3; and
n35 and n36 are independently 0, 1 or 2 provided that n35+n36 is 0, 1 or 2; and
Y is O, S, S(O), S(O)$_2$, N($C_1$-$C_2$alkyl), N($C_1$-$C_2$alkoxy), C(O), $CR^{38}R^{39}$ or —$CR^{310}R^{311}CR^{312}R^{313}$—; and
$R^{38}$ and $R^{39}$ are, independently of each other: hydrogen, $C_1$-$C_6$alkyl (in particular $C_1$-$C_4$alkyl, e.g. $C_1$-$C_2$alkyl), $C_2$-$C_4$alkenyl (in particular $C_2$-$C_3$alkenyl-$CH_2$—, e.g. ethenyl-$CH_2$—), $C_2$-$C_4$alkynyl (in particular $C_2$-$C_3$alkynyl-$CH_2$—, e.g. ethynyl-$CH_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl; $C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring $CH_2$ moiety of a $C_4$-$C_6$cycloalkyl is optionally (e.g. preferably) replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; $C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl); $C_5$-$C_6$cycloalkenyl or $C_5$-$C_6$cycloalkenyl substituted by one or two $C_1$-$C_3$alkyl (in particular methyl) substituents; $C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl, and in which one ring $CH_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; $C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or HetA or HetA-$CH_2$—;
wherein HetA is a heteroaryl, attached at a ring-carbon, which is optionally substituted by 1, 2 or 3 (in particular 1 or 2, e.g. 1) ring-carbon substituents independently $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), $SR^{6E}$, S(O)$R^{6E}$, —S(O)$_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;
provided that no more than one of $R^{38}$ and $R^{39}$ is an optionally substituted cycloalkyl; an optionally substituted cycloalkyl in which one ring $CH_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), S(O)$_2$, NH, N($C_1$-

$C_3$alkyl), $N(C_1$-$C_2$fluoroalkyl), $N[C(O)C_1$-$C_3$alkyl], $N[C(O)C_1$-$C_2$fluoroalkyl]$ or $N(C_1$-$C_2$alkoxy) moiety; or HetA or HetA-$CH_2$—;

or $R^{38}$ is hydrogen or $C_1$-$C_2$alkyl (in particular H or Me), and $R^{39}$ is $C_1$-$C_2$alkoxy (in particular methoxy);

or $R^{38}$ and $R^{39}$ taken together are —$(CH_2)_{n37}$— or —$(CH_2)_{n38}$—$X^{32}$—$(CH_2)_{n39}$—;

wherein $X^{32}$ is O, S, S(O), $S(O)_2$, NH, $N(C_1$-$C_3$alkyl), $N(C_1$-$C_2$fluoroalkyl), $N[C(O)C_1$-$C_3$alkyl]$, $N[C(O)C_1$-$C_2$fluoroalkyl]$, $N(C_1$-$C_2$alkoxy), $C(H)(C_1$-$C_3$alkyl), $C(C_1$-$C_2$alkyl)$_2$ or $C(H)(C_1$-$C_3$alkoxy);

n37 is 2, 3, 4, 5 or 6 (in particular 4 or 5); and n38 and n39 are independently 0, 1, 2 or 3 provided that n38+n39 is 2, 3, 4 or 5 (in particular 3 or 4); and $R^{310}$, $R^{311}$, $R^{312}$ and $R^{313}$ are independently of each other hydrogen or $C_1$-$C_4$alkyl (in particular $C_1$-$C_2$alkyl) provided that no more than one of $R^{310}$, $R^{311}$, $R^{312}$ and $R^{313}$ is $C_3$-$C_4$alkyl;

and wherein:

$R^{6AA}$ is $C_1$fluoroalkyl (preferably trifluoromethyl), fluorine, chlorine or bromine;

$R^{6BB}$, $R^{6C1}$ and $R^{6C2}$ independently are hydrogen, methyl, $C_1$fluoroalkyl (preferably trifluoromethyl), fluorine or chlorine; provided that $R^{6BB}$, $R^{6C1}$ and $R^{6C2}$ in total contain no more than one carbon atom, and $R^{6BB}$, $R^{6C1}$ and $R^{6C2}$ in total comprise no more than one chlorine; and provided that —$C(R^{6BB})$=$C(R^{6C1})(R^{6C2})$ is not $C_2$-$C_3$alkenyl; and $R^{6E}$ is $C_1$-$C_3$alkyl (preferably $C_1$-$C_2$alkyl such as methyl), $C_1$fluoroalkyl (preferably trifluoromethyl), or —$N(R^{6H})(R^{6J})$;

$R^{6F}$ is —$C(O)$—$C_1$-$C_2$alkyl (preferably —$C(O)$-methyl), —$C(O)$—$C_1$fluoroalkyl (preferably —$C(O)$-trifluoromethyl), —$S(O)_2$—$C_1$-$C_2$alkyl (preferably —$S(O)_2$-methyl), —$S(O)_2$—$C_1$fluoroalkyl (preferably —$S(O)_2$-trifluoromethyl), $C_1$-$C_2$alkyl (preferably methyl), or $C_1$fluoroalkyl (preferably trifluoromethyl);

$R^{6G}$ and $R^{6J}$ independently are hydrogen, methyl or $C_1$fluoroalkyl (preferably trifluoromethyl); and $R^{6H}$ is hydrogen, $C_1$-$C_2$alkyl (preferably methyl), or $C_1$fluoroalkyl (preferably trifluoromethyl); and and wherein in Q2:

G is hydrogen; an agriculturally acceptable metal, or an agriculturally acceptable sulfonium or ammonium group; or G is —$C(X^a)$—$R^a$, —$C(X^b)$—$X^c$—$R^b$, —$C(X^d)$—$N(R^e)$—$R^d$, —$SO_2$—$R^e$, —$P(X^e)(R^f)$—$R^g$, —$CH_2$—$X^f$—$R^h$; or phenyl-$CH_2$— or phenyl-$CH(C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-$CH(C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-$C(O)$—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-$C(O)$—$CH_2$—, $C_1$-$C_6$alkoxy-$C(O)$—CH=CH—, $C_2$-$C_7$alken-1-yl-$CH_2$—, $C_2$-$C_7$alken-1-yl-$CH(C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-$CH(C_1$-$C_2$alkyl)-;

wherein $X^a$, $X^b$, $X^c$, $X^d$, $X^e$ and $X^f$ are independently of each other oxygen or sulfur (in particular oxygen); and wherein $R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

and wherein "heteroaryl" means an aromatic ring system containing at least one ring heteroatom and consisting either of a single ring or of two fused rings;

and wherein the compound of formula (I) is optionally present (e.g. where chemically possible) as an agrochemically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF$—, $CF_3CH_2$—, $CHF_2CH_2$—, $CH_2FCH_2$—, $CHF_2CF_2$— or $(CH_3)_2CF$—. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO$—, $CF_3CH_2O$—, $CHF_2CH_2O$— or $CH_2FCH_2O$—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single heteroaryl rings will contain 1, 2 or 3 ring heteroatoms and/or bicyclic heteroaryl systems will contain 1, 2, 3 or 4 ring heteroatoms, each of which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula [N($R_a$$R_b$$R_c$$R_d$)]OH, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e$$R_f$$R_g$]OH, wherein $R_e$, $R_f$ and $R_g$ are each independently of the others $C_1$-$C_4$alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups (i.e. leaving or removeable groups) within G (for example, without limitation, the latentiating groups where G is —C($X^a$)—$R^a$ or —C($X^b$)—$X^c$—$R^b$, et al.) are generally selected to allow their removal, typically by one or a combination of biochemical, chemical or physical processes, to afford the corresponding compound of formula (I) where G is H, before, during or following (preferably during or following) application of the compound of formula (I) to the treated area (e.g. field) or to plants. Examples of these processes include enzymatic cleavage or other in/on-plant cleavage (e.g. cleavage of ester, carbonate and/or thiocarbonate moieties), chemical hydrolysis, and/or photoloysis. Some compounds bearing such groups G occasionally offer certain advantages or different technical properties, such as improved and/or more consistent and/or different penetration of the cuticula of the plants treated, increased and/or different tolerance (non-phytotoxicity) on certain crops, improved and/or different compatibility or stability in formulated mixtures containing other herbicides, herbicide safeners, plant growth regulators, fungicides or insecticides, or reduced and/or different leaching properties in soils.

The preferred, suitable and/or particular values of the substituents in or other features of the compound of formula (I), in particular G, X, Y, $R^1$, $R^2$, $R^{2A}$, $R^{6AA}$, $R^{6BB}$, $R^{6C1}$, $R^{6C2}$, $R^{6E}$, $R^{6F}$, $R^{6G}$, $R^{6H}$, $R^{6J}$, $R^{33}$, $R^{34}$, $R^{35}$, $R^{36}$, $R^{37}$, $R^{37a}$, $R^{37b}$, $R^{38}$, $R^{39}$, $R^{310}$, $R^{311}$, $R^{312}$, $R^{313}$, $R^a$, $R^b$, $R^c$, $R^d$, $R^e$, $R^f$, $R^g$, $R^h$, $X^a$, $X^b$, $X^c$, $X^d$, $X^e$, $X^f$, Q, V, HetA, $X^{32}$, n34, n35, n36, n37, n38, and/or n39, are set out below (and/or generally herein), and can be either taken alone or taken together with one or more of any other preferred, suitable and/or particular features in any combination(s) thereof. In this paragraph, "preferred" is intended to encompass more preferred, even or still or yet more preferred, particularly or highly preferred, most preferred and all similar terms. For the avoidance of doubt, preferred, suitable and/or particular features can be combined together with preferred, suitable and/or particular features with different levels of ranking (e.g. with different levels of preference).

In one particular embodiment of the invention, X is chlorine. However, in the present invention, most preferably, X is methyl.

In the present invention, most preferably, $R^1$ is fluorine. In a further preferable embodiment of the invention, $R^1$ is bromine.

Therefore, most preferably, X is methyl, and $R^1$ is fluorine, for all aspects and/or embodiments of the invention. In an alternative, also highly preferable, embodiment of the invention (which e.g. can apply to all aspects and/or embodiments of the invention), X is methyl, and $R^1$ is bromine.

As described above, $R^2$ is ethynyl, $C_1$-$C_3$alkoxy-, $C_1$-$C_3$haloalkoxy- (in particular $C_1$-$C_3$fluoroalkoxy-), or $C_1$-$C_3$alkoxy-$C_1$-$C_3$alkoxy-.

In one embodiment, $R^2$ is ethynyl.

Preferably, $R^2$ is —O—$R^{2A}$, wherein $R^{2A}$ is $C_1$-$C_3$alkyl, $C_1$-$C_3$haloalkyl (in particular $C_1$-$C_3$fluoroalkyl), or $C_1$-$C_3$alkoxy-$C_1$-$C_3$alkyl-. Where $R^{2A}$ is $C_1$-$C_3$alkyl, $R^{2A}$ being methyl or ethyl is preferred. Where $R^{2A}$ is $C_1$-$C_3$haloalkyl, $R^{2A}$ being $C_1$-$C_3$fluoroalkyl is preferred (more preferably $C_1$-$C_2$fluoroalkyl, even more preferably $C_1$fluoroalkyl). Where $R^{2A}$ is $C_1$-$C_3$haloalkyl or $C_1$-$C_3$fluoroalkyl, more specifically, $R^{2A}$ being trifluoromethyl, difluoromethyl, or trifluoroethyl (e.g. 2,2,2-trifluoroethyl) is especially preferred, most particularly trifluoromethyl or difluoromethyl. Where $R^{2A}$ is $C_1$-$C_3$alkoxy-$C_1$-

$C_3$alkyl-, —$CH_2CH_2OCH_3$ (i.e. 2-methoxyethyl-) is preferred. In these preferred embodiments, preferably $R^1$ is fluorine and/or X is methyl.

Therefore, more preferably, in all aspects and/or embodiments of the invention, $R^2$ is —O—$R^{2A}$, wherein $R^{2A}$ is methyl, ethyl, $C_1$-$C_2$fluoroalkyl (in particular trifluoromethyl, difluoromethyl, or trifluoroethyl such as 2,2,2-trifluoroethyl), or —$CH_2CH_2OCH_3$ (i.e. 2-methoxyethyl-). In this more preferred embodiment, preferably $R^1$ is fluorine and/or X is methyl.

Even more preferably, in all aspects and/or embodiments of the invention, $R^2$ is —O—$R^{2A}$, wherein $R^{2A}$ is methyl, ethyl or $C_1$fluoroalkyl, in particular methyl, ethyl, trifluoromethyl or difluoromethyl. In these even more preferred embodiments, preferably $R^1$ is fluorine and/or X is methyl.

Most preferably, in all aspects and/or embodiments of the invention, $R^2$ is —O—$R^{2A}$, wherein $R^{2A}$ is methyl. In this most preferred embodiment, preferably $R^1$ is fluorine and/or X is methyl.

Therefore, most preferably, in all aspects and/or embodiments of the invention, X is methyl, $R^1$ is fluorine, and $R^2$ is —O—$R^{2A}$ wherein $R^{2A}$ is methyl.

Preferably, e.g. in all aspects and/or embodiments of the invention, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is —$C(X^a)$—$R^a$, —$C(X^b)$—$X^c$—$R^b$, —$SO_2$—$R^e$, or —$CH_2$—$X^f$—$R^h$; wherein $X^a$, $X^b$, $X^c$, $X^f$, $R^a$, $R^b$, $R^e$ and $R^h$ are as defined herein.

More preferably, e.g. in all aspects and/or embodiments of the invention, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is —$C(X^a)$—$R^a$ or —$C(X^b)$—$X^c$—$R^b$, wherein $X^a$, $R^a$, $X^b$, $X^c$ and $R^b$ are as defined herein.

In a particular embodiment, G is a group —$C(X^a)$—$R^a$ or —$C(X^b)$—$X^c$—$R^b$, wherein $X^a$, $R^a$, $X^b$, $X^c$ and $R^b$ are as defined herein.

Preferably, e.g. in all aspects and/or embodiments of the invention, $X^a$, $X^b$, $X^c$, $X^d$, $X^e$ and/or $X^f$ are oxygen; and/or $X^c$ is sulfur.

More preferably, $X^a$, $X^b$, $X^e$ and $X^f$ are oxygen; and $X^c$ is oxygen or sulfur. Even more preferably, $X^a$, $X^b$, $X^c$, $X^e$ and $X^f$ are oxygen.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl. Alternatively, preferably, $R^a$ is $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro; or heteroaryl or heteroaryl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1C_3$alkoxy (e.g. $C_1$alkoxy), $C_1$-$C_3$fluoroalkoxy (e.g. $C_1$fluoroalkoxy), halogen (e.g. fluorine, chlorine or bromine), or cyano (in which the heteroaryl preferably consists of a single ring).

More preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_1$-$C_4$alkoxy$C_1$-$C_4$alkyl, $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro.

Preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl. Alternatively, preferably, $R^b$ is $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro; or heteroaryl or heteroaryl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), or cyano (in which the heteroaryl preferably consists of a single ring).

More preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_1$-$C_4$alkoxy$C_1$-$C_4$alkyl, $C_3$-$C_7$cycloalkyl$C_1$alkyl; or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro.

Preferably, $R^e$ is $C_1$-$C_{10}$alkyl (e.g. $C_1$-$C_6$alkyl or $C_1$-$C_4$alkyl), $C_1$-$C_{10}$fluoroalkyl (e.g. $C_1$-$C_3$fluoroalkyl); or phenyl or phenyl substituted by 1, 2 or 3 (e.g. 1 or 2) of, independently, $C_1$-$C_3$alkyl (e.g. $C_1$alkyl), $C_1$-$C_3$fluoroalkyl (e.g. $C_1$fluoroalkyl), $C_1$-$C_3$alkoxy (e.g. $C_1$alkoxy), $C_1$-$C_3$fluoroalkoxy (e.g. $C_1$fluoroalkoxy), halogen (e.g. fluorine, chlorine or bromine), cyano or nitro.

Preferably, $R^h$ is $C_1$-$C_{10}$alkyl (e.g. $C_1$-$C_6$alkyl or $C_1$-$C_4$alkyl), $C_1$-$C_{10}$fluoroalkyl (e.g. $C_1$-$C_3$fluoroalkyl) or $C_1$-$C_6$alkyl-C(O)— (e.g. $C_1$-$C_4$alkyl-C(O)—). In particular, $R^e$ is $C_1$-$C_{10}$alkyl (e.g. $C_1$-$C_6$alkyl or $C_1$-$C_4$alkyl).

When G is —$C(X^a)$—$R^a$ or —$C(X^b)$—$X^c$—$R^b$, then preferably $X^a$ and $X^b$ are oxygen, and $X^c$ is oxygen or sulfur, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl; and $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl.

In a further particular embodiment, G is hydrogen, or an agriculturally acceptable alkali metal or alkaline earth metal (e.g. lithium, sodium, potassium, magnesium or calcium), or an agriculturally acceptable sulfonium or ammonium group. More preferably, G is hydrogen, or an agriculturally acceptable alkali metal or alkaline earth metal (e.g. lithium, sodium, potassium, magnesium or calcium). Most preferably G is hydrogen.

In a particularly preferable embodiment of the invention, the compound of formula (I) is a compound described in any of Tables 1, 2, 3, 4, 5 or 6, as described and/or illustrated herein, optionally present (e.g. where chemically possible) as an agrochemically acceptable salt thereof.

In a more particularly preferable embodiment of the invention, the compound of formula (I) is any one of the compounds A1 to A7, or A8, or A9 or A10, or P1 to P5, as described and/or illustrated herein, optionally present (e.g. where chemically possible) as an agrochemically acceptable salt (e.g. agrochemically acceptable metal, sulfonium or ammonium salt) thereof.

In an even more particularly preferable embodiment of the invention, the compound of formula (I) is any one of the compounds A1 to A7, or A8, or P1 to P5, as described and/or illustrated herein, optionally present (e.g. where chemically possible) as an agrochemically acceptable salt (e.g. agrochemically acceptable metal, sulfonium or ammonium salt) thereof.

In the present invention, Q is a subgroup of formula Q2 as defined above, and so a compound of formula (I) has the general structure (I-2)

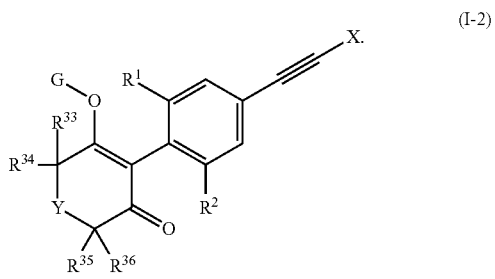

(I-2)

In all aspects and/or embodiments of the invention, $R^{34}$ and $R^{35}$ taken together are —$(CH_2)_{n34}$— or —$(CH_2)_{n35}$—$C(R^{37a})(R^{37b})$—$(CH_2)_{n36}$—.

In the present invention, $R^{37a}$ is $C_1$-$C_2$alkyl; and $R^{37b}$ is hydrogen or $C_1$-$C_2$alkyl.

In all aspects and/or embodiments of the invention:
$R^{34}$ and $R^{35}$ taken together are —$(CH_2)_{n34}$— or —$(CH_2)_{n35}$—$C(R^{37a})(R^{37b})$—$(CH_2)_{n36}$—;
wherein $R^{37a}$ is $C_1$-$C_2$alkyl; $R^{37b}$ is hydrogen or $C_1$-$C_2$alkyl;
n34 is 1, 2 or 3 (preferably 2 or 3); and
n35 and n36 are independently 0, 1 or 2 provided that n35+n36 is 0, 1 or 2 (preferably 1 or 2).

Preferably, n34 is 2 or 3.
Preferably, n35 and n36 are independently 0, 1 or 2 provided that n35+n36 is 1 or 2.

Preferably, e.g. in all aspects and/or embodiments of the invention when Q is Q2, $R^{33}$ and/or $R^{36}$, independently of each other, are hydrogen, $C_1$-$C_4$alkyl (e.g. $C_1$-$C_2$alkyl), $C_2$-$C_4$ alkynyl (in particular $C_2$-$C_3$alkynyl-$CH_2$—, e.g. ethynyl-$CH_2$—), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkyl-sulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, said heterocyclyl being attached at a ring carbon atom within the heterocyclyl (in particular tetrahydrofuranyl such as tetrahydrofuran-3-yl, or tetrahydropyranyl such as tetrahydropyran-4-yl); provided that no more than one (in particular none) of $R^{33}$ and $R^{36}$ is alkenyl, alkynyl, alkoxyalkyl, alkylthioalkyl, alkylsulfinylalkyl, alkylsulfonylalkyl, cycloalkyl or heterocyclyl;
and/or $R^{34}$ and $R^{35}$ taken together are —$(CH_2)_{n34}$— or —$(CH_2)_{n35}$—$C(R^{37a})(R^{37b})$—$(CH_2)_{n36}$—; wherein $R^{37a}$ is $C_1$-$C_2$alkyl; $R^{37b}$ is hydrogen or $C_1$-$C_2$alkyl; n34 is 1, 2 or 3 (preferably 2 or 3); and n35 and n36 are independently 0, 1 or 2 provided that n35+n36 is 0, 1 or 2 (preferably 1 or 2).

More preferably, e.g. in all aspects and/or embodiments of the invention when Q is Q2, $R^{33}$ and/or $R^{36}$, independently of each other, are hydrogen, $C_1$-$C_4$alkyl (in particular $C_1$-$C_2$alkyl), $C_2$-$C_4$alkynyl (in particular $C_2$-$C_3$alkynyl-$CH_2$—, e.g. ethynyl-$CH_2$—), $C_1$-$C_3$alkoxy$C_1$-$C_3$alkyl (in particular $C_1$-$C_2$alkoxy$C_1$-$C_2$alkyl), $C_1$-$C_3$alkylthio$C_1$-$C_3$alkyl (in particular $C_1$-$C_2$alkylthio$C_1$-$C_2$alkyl), $C_1$-$C_3$alkylsulfinyl$C_1$-$C_3$alkyl (in particular $C_1$-$C_2$alkylsulfinyl$C_1$-$C_2$alkyl), $C_1$-$C_3$alkylsulfonyl$C_1$-$C_3$alkyl (in particular $C_1$-$C_2$alkylsulfonyl$C_1$-$C_2$alkyl); $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, said heterocyclyl being attached at a ring carbon atom within the heterocyclyl (in particular tetrahydrofuranyl such as tetrahydrofuran-3-yl, or tetrahydropyranyl such as tetrahydropyran-4-yl); provided that no more than one (in particular none) of $R^{33}$ and $R^{36}$ is alkenyl, alkynyl, alkoxyalkyl, alkylthioalkyl, alkylsulfinylalkyl, alkylsulfonylalkyl, cycloalkyl or heterocyclyl;
and/or $R^{34}$ and $R^{35}$ taken together are —$(CH_2)_{n34}$— or —$(CH_2)_{n35}$—$C(R^{37a})(R^{37b})$—$(CH_2)_{n36}$—; wherein $R^{37a}$ is $C_1$-$C_2$alkyl; $R^{37b}$ is hydrogen or $C_1$-$C_2$alkyl; n34 is 2 or 3; and n35 and n36 are independently 0, 1 or 2 provided that n35+n36 is 1 or 2.

Still more preferably, $R^{33}$ and/or $R^{36}$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^{33}$ and $R^{36}$ is alkoxyalkyl; and/or $R^{34}$ and $R^{35}$ taken together are —$(CH_2)_{n34}$— or —$(CH_2)_{n35}$—$C(R^{37a})(R^{37b})$—$(CH_2)_{n36}$—; wherein $R^{37a}$ is $C_1$-$C_2$alkyl; $R^{37b}$ is hydrogen or $C_1$-$C_2$alkyl; n34 is 2 or 3; and n35 and n36 are independently 0, 1 or 2 provided that n35+n36 is 1 or 2.

Even more preferably, $R^{33}$ and/or $R^{36}$, independently of each other, are hydrogen or $C_1$-$C_2$alkyl (preferably hydrogen or methyl); and/or $R^{34}$ and $R^{35}$ taken together are —$(CH_2)_{n34}$— wherein n34 is 2 or 3, and more preferably n34 is 2.

Most preferably (especially when Y is $CR^{38}R^{39}$ or —$CR^{310}R^{311}CR^{312}R^{313}$—), $R^{33}$ and $R^{36}$ are hydrogen; and/or $R^{34}$ and $R^{35}$ taken together are —$(CH_2)_{n34}$— wherein n34 is 2 or 3, and $R^{33}$ and $R^{36}$ are hydrogen.

Preferably, e.g. in all aspects and/or embodiments of the invention when Q is Q2, at least one (more preferably 2, 3 or 4, still more preferably 3 or 4, most preferably all four) of $R^{33}$ and $R^{36}$, independently of each other, are hydrogen or $C_1$-$C_4$alkyl (e.g. H or $C_1$-$C_3$alkyl, or H or $C_1$-$C_2$alkyl); and/or $R^{34}$ and $R^{35}$ are taken together as described herein.

Preferably, e.g. in all aspects and/or embodiments of the invention when Q is Q2, Y is O, S, S(O), S(O)$_2$, C(O), $CR^{38}R^{39}$ or —$CR^{310}R^{311}CR^{312}R^{313}$—. More preferably, Y is O, C(O), $CR^{38}R^{39}$ or —$CR^{310}R^{311}CR^{312}R^{313}$—. Even more preferably, Y is O or $CR^{38}R^{39}$, in particular Y is O or $CH_2$. Most preferably, Y is $CR^{38}R^{39}$, in particular Y is $CH_2$.

Preferably, e.g. in all aspects and/or embodiments of the invention, in $R^{38}$ and $R^{39}$, one or both of $R^{38}$ and $R^{39}$ is or are hydrogen; or $R^{38}$ and $R^{39}$ taken together are —$(CH_2)_{n37}$— or preferably —$(CH_2)_{n38}$—$X^{32}$—$(CH_2)_{n39}$—. In this embodiment, preferably Y is $CR^{38}R^{39}$ and/or preferably $X^{32}$ is O.

19

In one particular embodiment when Q is Q2, $R^{38}$ and $R^{39}$ are taken together and are —$(CH_2)_{n37}$— or —$(CH_2)_{n38}$—$X^{32}$—$(CH_2)_{n39}$—. In this embodiment, preferably Y is $CR^{38}R^{39}$ and/or preferably $X^{32}$ is O.

Preferably, e.g. in all aspects and/or embodiments of the invention when Q is Q2, $X^{32}$ is O, S, S(O), $S(O)_2$, C(H)($C_1$-$C_3$alkyl), $C(C_1$-$C_2$alkyl$)_2$ or C(H)($C_1$-$C_3$alkoxy). Most preferably, $X^{32}$ is O.

Preferably, n37 is 2, 3, 4 or 5, more preferably 4 or 5.

Preferably, n38 and n39 are independently 1, 2 or 3 provided that n38+n39 is 2, 3 or 4. Preferably, n38+n39 is 3 or 4. Most preferably, n38 is 2 and n39 is 2 (in which case, preferably, $X^{32}$ is O).

Preferably, e.g. in all aspects and/or embodiments of the invention when Q is Q2, $R^{38}$ and $R^{39}$ are, independently of each other:

hydrogen, $C_1$-$C_4$alkyl (in particular $C_1$-$C_2$alkyl), $C_2$-$C_3$alkenyl-$CH_2$— (in particular ethenyl-$CH_2$—), $C_2$-$C_3$alkynyl-$CH_2$— (in particular ethynyl-$CH_2$—), $C_1$-$C_2$fluoroalkyl (in particular $C_1$fluoroalkyl), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring $CH_2$ moiety of a $C_4$-$C_6$cycloalkyl is optionally (e.g. preferably) replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl, and in which one ring $CH_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or HetA or HetA-$CH_2$—, wherein HetA is a heteroaryl, attached at a ring-carbon, which is optionally substituted by 1, 2 or 3 (in particular 1 or 2, e.g. 1) ring-carbon substituents independently being $C_1$-$C_3$alkyl (e.g. $C_1$-$C_2$alkyl), $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl (e.g. ethenyl or prop-1-enyl), $C_2$-$C_3$alkynyl (e.g. ethynyl or prop-1-ynyl), $C_1$-$C_3$alkoxy (e.g. $C_1$-$C_2$alkoxy), $C_1$-$C_2$fluoroalkoxy, halogen (e.g. fluorine or chlorine), cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;

20 provided that no more than one of $R^{38}$ and $R^{39}$ is an optionally substituted cycloalkyl; an optionally substituted cycloalkyl in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; or HetA or HetA-$CH_2$—;

or $R^{38}$ is hydrogen or $C_1$-$C_2$alkyl (in particular H or Me), and $R^{39}$ is $C_1$-$C_2$alkoxy (in particular methoxy);

or $R^{38}$ and $R^{39}$ taken together are —$(CH_2)_{n37}$— or —$(CH_2)_{n38}$—$X^{32}$—$(CH_2)_{n39}$—.

In the above preferred embodiment, preferably Y is $CR^{38}R^{39}$ and/or preferably $X^{32}$ is O.

More preferably, e.g. in all aspects and/or embodiments of the invention when Q is Q2: $R^{38}$ is hydrogen or $C_1$-$C_2$alkyl (preferably H or Me, more preferably hydrogen); and $R^{39}$ is:

$C_1$-$C_2$alkoxy (in particular methoxy);

$C_2$-$C_3$alkynyl-$CH_2$— (in particular ethynyl-$CH_2$—);

$C_1$-$C_3$alkoxy$C_1$-$C_3$alkyl;

$C_1$-$C_3$alkylthio$C_1$-$C_3$alkyl (preferably $C_1$-$C_2$alkylthio-$CH_2CH_2$— or more preferably $C_1$-$C_2$alkylthio-CH(Me)$CH_2$—);

$C_1$-$C_3$alkylsulfinyl$C_1$-$C_3$alkyl;

$C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring $CH_2$ moiety of a $C_4$-$C_6$cycloalkyl is optionally (e.g. preferably) replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a S(O), $S(O)_2$, NH, N($C_1$-$C_3$alkyl) or N($C_1$-$C_2$alkoxy) moiety; or still more preferably is replaced by an oxygen or sulfur atom);

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkylmethyl- or $C_3$-$C_6$cycloalkylmethyl- substituted by one or two ring substituents which independently are $C_1$-$C_3$alkyl (in particular $C_1$-$C_2$alkyl) or $C_1$-$C_2$fluoroalkyl, and in which one ring $CH_2$ moiety of a $C_4$-$C_6$cycloalkylmethyl- is optionally (e.g. preferably) replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a N[C(O)$C_1$-$C_3$alkyl] or N[C(O)$C_1$-$C_2$fluoroalkyl]moiety);

$C_3$-$C_6$cycloalkylmethyl- substituted by one ring substituent being $C_1$-$C_3$alkoxy (in particular $C_1$-$C_2$alkoxy) and optionally further substituted by one ring substituent being $C_1$-$C_2$alkyl (in particular methyl); or HetA or HetA-$CH_2$—, wherein Het A is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-C(O)—, $C_1$-$C_2$fluoroalkyl-C(O)—, hydroxy (including any oxo tautomer), $C_2$-$C_3$alkenyl (in particular ethenyl or prop- 1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

or $R^{38}$ and $R^{39}$ taken together are —(CH$_2$)$_{n37}$— or —(CH$_2$)$_{n38}$—X$^{32}$—(CH$_2$)$_{n39}$—.

In the above preferred embodiment, preferably Y is CR$^{38}$R$^{39}$ and/or preferably X$^{32}$ is O.

Even more preferably, e.g. in all aspects and/or embodiments of the invention when Q is Q2:

$R^{38}$ is hydrogen or $C_1$-$C_2$alkyl (preferably H or Me, more preferably hydrogen); and
$R^{39}$ is:

$C_1$-$C_3$alkylthio$C_1$-$C_3$alkyl (preferably $C_1$-$C_2$alkylthio-CH$_2$CH$_2$— or more preferably $C_1$-$C_2$alkylthio-CH(Me)CH$_2$—);

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl, and in which one ring CH$_2$ moiety of a $C_4$-$C_6$cycloalkyl is replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or preferably is replaced by an oxygen or sulfur atom or by a S(O), S(O)$_2$, NH, N($C_1$-$C_3$alkyl) or N($C_1$-$C_2$alkoxy) moiety; or more preferably is replaced by an oxygen or sulfur atom);

$C_3$-$C_6$cycloalkylmethyl- or $C_3$-$C_6$cycloalkylmethyl- substituted by one or two ring substituents which independently are $C_1$-$C_3$alkyl (in particular $C_1$-$C_2$alkyl) or $C_1$-$C_2$fluoroalkyl, and in which one ring CH$_2$ moiety of a $C_4$-$C_6$cycloalkylmethyl- is replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or preferably is replaced by an oxygen or sulfur atom or by a N[C(O)$C_1$-$C_3$alkyl] or N[C(O)$C_1$-$C_2$fluoroalkyl]moiety);

HetA or HetA-CH$_2$—, wherein Het A is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-C(O)—, $C_1$-$C_2$fluoroalkyl-C(O)—, hydroxy (including any oxo tautomer), $C_2$-$C_3$alkenyl (in particular ethenyl or prop-1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

or $R^{38}$ and $R^{39}$ taken together are —(CH$_2$)$_{n37}$— or —(CH$_2$)$_{n38}$—X$^{32}$—(CH$_2$)$_{n39}$—.

In the above even more preferred embodiment, preferably Y is CR$^{38}$R$^{39}$ and/or preferably X$^{32}$ is O.

In one most preferable embodiment (which e.g. can apply to all aspects and/or embodiments of the invention when Q is Q2), $R^{38}$ and $R^{39}$ are, independently of each other, hydrogen or $C_1$-$C_3$alkyl (preferably hydrogen or $C_1$-$C_2$alkyl, more preferably hydrogen or methyl, most preferably hydrogen). In this embodiment, preferably, Y is CR$^{38}$R$^{39}$.

In another preferable embodiment (which e.g. can apply to all aspects and/or embodiments of the invention), $R^{38}$ is hydrogen, and $R^{39}$ is $C_1$-$C_3$alkylthio$C_1$-$C_3$alkyl. In this embodiment, $R^{39}$ preferably is $C_1$-$C_2$alkylthio-CH$_2$CH$_2$— or more preferably is $C_1$-$C_2$alkylthio-CH(Me)CH$_2$—. In this embodiment, preferably, Y is CR$^{38}$R$^{39}$.

In another preferable embodiment (which e.g. can apply to all aspects and/or embodiments of the invention when Q is Q2), $R^{38}$ is hydrogen and $R^{39}$ is $C_4$-$C_6$cycloalkylmethyl- or $C_4$-$C_6$cycloalkylmethyl- substituted by one or two ring substituents which independently are $C_1$-$C_3$alkyl (in particular $C_1$-$C_2$alkyl) or $C_1$-$C_2$fluoroalkyl, and in which one ring CH$_2$ moiety is replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a N[C(O)$C_1$-$C_3$alkyl] or N[C(O)$C_1$-$C_2$fluoroalkyl]moiety). In this embodiment, preferably, Y is CR$^{38}$R$^{39}$.

Within the above preferable embodiment, then preferably $R^{38}$ is hydrogen and $R^{39}$ is heterocyclyl-methyl-, wherein the heterocyclyl is V, wherein V is one of the following sub-formulae $V_1$, $V_2$, $V_3$, $V_4$, $V_5$, $V_6$, $V_7$, $V_{33}$, $V_{34}$, $V_{37}$, $V_{38}$, $V_{41}$, $V_{42}$, $V_{43}$, $V_{44}$, $V_{47}$, $V_{87}$, $V_{89}$, $V_{90}$ or $V_{107}$:

(V$_1$)

(V$_2$)

(V$_3$)

(V$_4$)

(V$_5$)

(V$_6$)

(V$_7$)

(V$_8$)

-continued

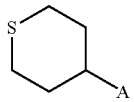 (V₉)

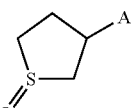 (V₁₀)

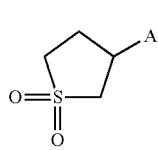 (V₃₈)

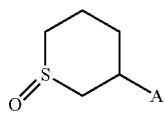 (V₄₁)

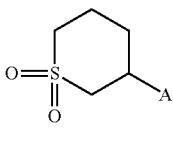 (V₄₂)

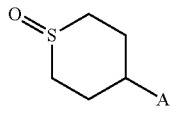 (V₄₃)

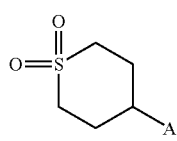 (V₄₄)

 (V₄₇)

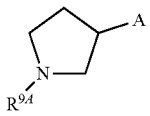 (V₈₇)

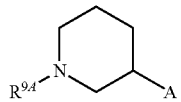 (V₈₉)

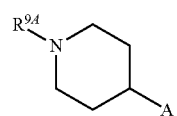 (V₉₀)

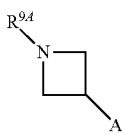 (V₁₀₇)

wherein: A is the position of attachment to the -methyl-moiety; and $R^{9A}$ is hydrogen, $C_1$-$C_2$alkyl (e.g. methyl), $C_1$-$C_2$fluoroalkyl (e.g. $C_1$fluoroalkyl), —C(O)$C_1$-$C_3$alkyl (e.g. —C(O)-methyl), —C(O)$C_1$-$C_2$fluoroalkyl (e.g. —C(O)$C_1$fluoroalkyl) or $C_1$-$C_2$alkoxy.

More preferably, V is one of the sub-formulae $V_1$, $V_2$, $V_4$, $V_6$, $V_7$, $V_{33}$, $V_{34}$, $V_{41}$, $V_{42}$, $V_{43}$, $V_{44}$, $V_{87}$, $V_{89}$ or $V_{90}$. Even more preferably, V is one of the sub-formulae $V_2$, $V_6$, $V_7$, $V_{33}$, $V_{34}$, $V_{41}$, $V_{42}$, $V_{43}$, $V_{44}$, $V_{87}$, $V_{89}$ or $V_{90}$.

Yet more preferably, V is one of the sub-formulae $V_2$, $V_7$, $V_{87}$ or $V_{90}$. Further more preferably, V is one of the sub-formulae $V_2$, $V_7$ or $V_{90}$.

Most preferably, V is sub-formula $V_7$.

Preferably, $R^{9A}$ is —C(O)$C_1$-$C_3$alkyl (e.g. —C(O)methyl) or —C(O)$C_1$-$C_2$fluoroalkyl (e.g. —C(O)$C_1$fluoroalkyl).

In one preferable embodiment of the invention (which e.g. can apply to all aspects and/or embodiments of the invention), $R^{38}$ is hydrogen, and $R^{39}$ is tetrahydro-2H-pyran-4-yl

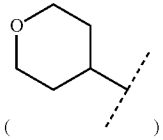

or (tetrahydro-2H-pyran-4-yl)-methyl-. In this embodiment, preferably, Y is $CR^{38}R^{39}$. When $R^{39}$ is (tetrahydro-2H-pyran-4-yl)-methyl-, then $R^{39}$ is $V_7$-methyl- wherein $V_7$ is

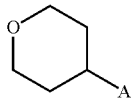

wherein A is the position of attachment to the -methyl-moiety.

In another preferable embodiment (which e.g. can apply to all aspects and/or embodiments of the invention when Q is Q2), $R^{38}$ is hydrogen and $R^{39}$ is HetA or HetA-CH$_2$— as defined herein. In this embodiment, more preferably, $R^{38}$ is hydrogen and $R^{39}$ is HetA as defined herein. In this embodiment, preferably, Y is $CR^{38}R^{39}$.

Preferably, e.g. in all aspects and/or embodiments of the invention when Q is Q2, and $R^{39}$ is HetA or HetA-CH$_2$, HetA is a heteroaryl (in particular monocyclic heteroaryl), attached at a ring-carbon, which is optionally substituted by 1, 2 or 3 (in particular 1 or 2, e.g. 1) ring-carbon substituents independently being $C_1$-$C_2$alkyl, $C_1$fluoroalkyl, $C_1$-$C_2$alkyl-C(O)—, $C_1$fluoroalkyl-C(O)—, hydroxy (including any oxo tautomer), ethynyl, prop-1-ynyl, $C_1$-$C_2$alkoxy, $C_1$fluoroalkoxy, fluorine, chlorine, bromine, cyano or nitro, provided that any chlorine, bromine, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent.

More preferably, e.g. in all aspects and/or embodiments of the invention when Q is Q2, and $R^{39}$ is HetA or HetA-CH$_2$, HetA is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), $C_1$-$C_2$alkyl-C(O)— (in particular Me-C(O)—), $C_1$fluoroalkyl-C(O)—, ethynyl, prop-1-ynyl, fluorine or cyano; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_2$alkyl (e.g. methyl), $C_1$fluoroalkyl, methyl-C(O)— or $C_1$fluoroalkyl-C(O)— substituent.

More preferably, e.g. in all aspects and/or embodiments of the invention when Q is Q2, and $R^{39}$ is HetA or HetA-$CH_2$, HetA is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), fluorine or cyano; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one methyl substituent.

Preferably, e.g. in all aspects and/or embodiments of the invention when Q is Q2, and $R^{39}$ is HetA or HetA-$CH_2$, HetA is an optionally substituted monocyclic heteroaryl, attached at a ring-carbon. Such as monocyclic heteroaryl can be 5-membered or 6-membered monocyclic heteroaryl.

More preferably, e.g. in all aspects and/or embodiments of the invention when Q is Q2, and $R^{39}$ is HetA or HetA-$CH_2$, HetA is an optionally substituted monocyclic heteroaryl, attached at a ring-carbon, which is:
pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), tetrazol-5-yl, oxazolyl, thiazolyl, isoxazolyl, isothiazolyl or oxadiazolyl; optionally present (e.g. where chemically possible) as an agrochemically acceptable salt thereof (such as an agrochemically acceptable acid addition salt thereof).

Even more preferably, e.g. in all aspects and/or embodiments of the invention when Q is Q2, and $R^{39}$ is HetA or HetA-$CH_2$, HetA is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), or tetrazol-5-yl; optionally present (e.g. where chemically possible) as an agrochemically acceptable salt thereof (such as an agrochemically acceptable acid addition salt thereof).

Still more preferably, e.g. in all aspects and/or embodiments of the invention when Q is Q2, and $R^{39}$ is HetA or HetA-$CH_2$, HetA is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), or pyridazinyl (preferably pyridazin-3-yl); optionally present (e.g. where chemically possible) as an agrochemically acceptable salt thereof (such as an agrochemically acceptable acid addition salt thereof).

Yet more preferably, e.g. in all aspects and/or embodiments of the invention when Q is Q2, and $R^{39}$ is HetA or HetA-$CH_2$, HetA is an optionally substituted monocyclic heteroaryl, attached at a ring-carbon, which is: pyridin-3-yl, pyridin-2-yl, or pyrazolyl (preferably pyrazol-5-yl or pyrazol-4-yl, or most preferably pyrazol-3-yl); optionally present (e.g. where chemically possible) as an agrochemically acceptable salt thereof (such as an agrochemically acceptable acid addition salt thereof).

Most preferably, e.g. in all aspects and/or embodiments of the invention when Q is Q2, and $R^{39}$ is HetA or HetA-$CH_2$, HetA is an optionally substituted monocyclic heteroaryl, attached at a ring-carbon, which is: pyridin-2-yl or pyrazol-3-yl; optionally present (e.g. where chemically possible) as an agrochemically acceptable salt thereof (such as an agrochemically acceptable acid addition salt thereof).

It is particularly preferred (e.g. in all aspects and/or embodiments of the invention when Q is Q2 and $R^{39}$ is HetA or HetA-$CH_2$), that, in HetA, any ring-carbon atom, which is directly bonded to the ring-carbon atom which is the point of attachment (e.g. or i.e. which is the point of attachment to the central carbon atom within the Y=$CR^{38}R^{39}$ moiety (for HetA), or which is the point of attachment to the —$CH_2$— moiety (for Het-$CH_2$—), is unsubstituted. Therefore, for example, preferably, when Het is an optionally substituted pyridin-2-yl (optionally present as an agrochemically acceptable salt thereof), then the ring-carbon atom at the 3-position of the ring (calculated with respect to the pyridine ring nitrogen atom) is unsubstituted.

Preferably, e.g. in all aspects and/or embodiments of the invention when Q is Q2, $R^{310}$, $R^{311}$, $R^{312}$ and/or $R^{313}$ are, independently of each other, hydrogen or $C_1$-$C_2$alkyl (in particular hydrogen or methyl). More preferably, two, three or all of $R^{310}$, $R^{311}$, $R^{312}$ and $R^{313}$ are hydrogen. Most preferably, $R^{310}$, $R^{311}$, $R^{312}$ and $R^{313}$ are hydrogen.

In a particularly preferable embodiment of the invention (which e.g. can apply to all aspects and/or embodiments of the invention): Y is O or $CR^{38}R^{39}$ (preferably $CR^{38}R^{39}$); and $R^{34}$ and $R^{35}$ taken together are —$(CH_2)_{n34}$— or —$(CH_2)_{n35}$—$C(R^{37a})(R^{37b})$—$(CH_2)_{n36}$—; wherein $R^{37a}$ is $C_1$-$C_2$alkyl; $R^{37b}$ is hydrogen or $C_1$-$C_2$alkyl; n34 is 2 or 3; and n35 and n36 are independently 0, 1 or 2 provided that n35+n36 is 1 or 2. In this particularly preferable embodiment, more preferably, Y is O or $CR^{38}R^{39}$ (preferably $CR^{38}R^{39}$) wherein $R^{38}$ and $R^{39}$ are, independently of each other, hydrogen or $C_1$-$C_3$alkyl (in particular, this $C_1$-$C_3$alkyl can be $C_1$-$C_2$alkyl such as methyl). In this particularly preferable embodiment, even more preferably Y is O or $CH_2$; or, most preferably, Y is $CH_2$. In this particularly preferable embodiment, more preferably, $R^{33}$ and $R^{36}$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^{33}$ and $R^{36}$ is alkoxyalkyl. In this particularly preferable embodiment, even more preferably, $R^{33}$ and $R^{36}$, independently of each other, are hydrogen or $C_1$-$C_2$alkyl (preferably hydrogen or methyl); and/or $R^{34}$ and $R^{35}$ taken together are —$(CH_2)_{n34}$— wherein n34 is 2 or 3 (preferably 2).

In a further particularly preferred embodiment, $R^1$ is fluorine, X is methyl, $R^2$ is $OR^{2A}$, wherein $R^{2A}$ is selected from methyl, ethyl, $CH_2CH_2OCH_3$, 2,2,2-trifluoroethyl and difluoromethyl (most preferably $R^{2A}$ is selected from methyl, ethyl and difluoromethyl), Q is Q2 wherein Y is $CR^{38}R^{39}$ and $R^{38}$ and $R^{39}$ are each independently hydrogen or methyl (preferably both hydrogen or both methyl, more preferably both hydrogen), $R^{34}$ and $R^{35}$ taken together are —$(CH_2)_{n34}$— or —$(CH_2)_{n35}$—$C(R^{37a})(R^{37b})$—$(CH_2)_{n36}$— wherein n34, n35, n36, $R^{37a}$ and $R^{37b}$ are as described hereinbefore. Preferably, in this particularly preferred embodiment, n34 is 2 or 3; and n35 and n36 are independently 0, 1 or 2 provided that n35+n36 is 1 or 2. Preferably, in this particularly preferred embodiment, $R^{34}$ and $R^{35}$ taken together are —$(CH_2)_{n34}$— wherein n34 is 2. Preferably, in this particularly preferred embodiment, G is hydrogen. In this particularly preferred embodiment, more preferably, $R^{33}$ and $R^{36}$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^{33}$ and $R^{36}$ is alkoxyalkyl. In this particularly preferred embodiment, even more preferably, $R^{33}$ and $R^{36}$, independently of each other, are hydrogen or $C_1$-$C_2$alkyl (preferably hydrogen or methyl); and/or $R^{34}$ and $R^{35}$ taken together are —$(CH_2)_{n34}$— wherein n34 is 2 or 3 (preferably 2).

In a specific particularly preferred embodiment, the compound of the invention (compound of formula (I)) is as described herein in the following tables (e.g. is a compound as described herein in one of Tables 1, 2, 3, 4, 5 or 6), optionally present (e.g. where chemically possible) as an agrochemically acceptable salt (e.g. agrochemically acceptable metal, sulfonium or ammonium salt) thereof.

Particularly preferably, the compound of the invention (compound of formula (I)) is compound A1, A2, A3, A4, A5, A6, A7, A8, P1, P2, P3, P4 or P5, optionally present (e.g. where chemically possible) as an agrochemically acceptable salt (e.g. agrochemically acceptable metal, sulfonium or ammonium salt) thereof. In an alternative embodiment, the compound of the invention (compound of formula (I)) is compound A9 or A10, optionally present (e.g. where chemically possible) as an agrochemically acceptable salt (e.g. agrochemically acceptable metal, sulfonium or ammonium salt) thereof.

Particularly preferably, the compound of the invention (compound of formula (I)) is compound A1, A2, A3, A4, A5, A6 or A7 (more preferably compound A1, A2, A3, A4 or A7), optionally present (e.g. where chemically possible) as an agrochemically acceptable salt (e.g. agrochemically acceptable metal, sulfonium or ammonium salt) thereof.

Alternatively, preferably, the compound of the invention (compound of formula (I)) is compound A8, optionally present (e.g. where chemically possible) as an agrochemically acceptable salt (e.g. agrochemically acceptable metal, sulfonium or ammonium salt) thereof.

Alternatively, particularly preferably, the compound of the invention (compound of formula (I)) is compound P1, P2, P3, P4 or P5, optionally present (e.g. where chemically possible) as an agrochemically acceptable salt (e.g. agrochemically acceptable metal, sulfonium or ammonium salt) thereof.

Especially particularly preferably, the compound of the invention (compound of formula (I)) is compound A1, A2, A3, A4, A7, P1, P2, P3, P4 or P5, optionally present (e.g. where chemically possible) as an agrochemically acceptable salt (e.g. agrochemically acceptable metal, sulfonium or ammonium salt) thereof.

In an further, alternative, aspect of the invention, there is provided a compound B1, of the following structure:

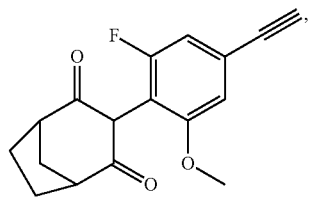 [SMILES: C#Cc1cc(F)c(C2C(=O)C3CCC(C3)C2=O)c(OC)c1]

optionally present (e.g. where chemically possible) as an agrochemically acceptable salt (e.g. agrochemically acceptable metal, sulfonium or ammonium salt) thereof.

Processes for Preparation of Compounds, e.g. Compounds of Formula (I)

Compounds of formula I, in which Q is Q2 may in general be made by the general methods described below.

A compound of formula I, wherein Q is Q2 and G is: —$C(X^a)$—$R^a$, —$C(X^b)$—$X^c$—$R^b$, —$C(X^d)$—$N(R^c)$—$R^d$, —$SO_2$—$R^e$, —$P(X^e)(R^f)$—$R^g$, —$CH_2$—$X^f$—$R^h$; or phenyl-$CH_2$— or phenyl-$CH(C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano, nitro, $SC_1$-$C_3$alkyl, $S(O)C_1$-$C_3$alkyl, or $S(O)_2C_1$-$C_3$alkyl), or heteroaryl-$CH_2$— or heteroaryl-$CH(C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano, nitro S, S(O), or $S(O)_2$), or phenyl-$C(O)$—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano, nitro, $SC_1$-$C_3$alkyl, $S(O)C_1$-$C_3$alkyl, or $S(O)_2C_1$-$C_3$alkyl); or $C_1$-$C_6$alkoxy-$C(O)$—$CH_2$—, $C_1$-$C_6$alkoxy-$C(O)$—CH=CH—, $C_2$-$C_7$alken-1-yl-$CH_2$—, $C_2$-$C_7$alken-1-yl-$CH(C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-$CH(C_1$-$C_2$alkyl)-; may be prepared by treating a compound of formula (2A), which is a compound of formula I wherein Q is Q2 and G is H, (a) with a reagent G1-Z, wherein G1-Z is an alkylating agent (wherein G1 is an organic group according to G within the compound of formula (I), wherein Q is Q2, and which is linked by a non-carbonyl, non-thiocarbonyl carbon atom) such as an organic halide (in which Z=halogen such as chlorine, bromine or iodine); wherein the organic halide (e.g. chloride) can typically be a substituted alkyl halide (e.g. chloride) such as a chloromethyl alkyl ether Cl—$CH_2$—$X^f$—$R^h$ wherein $X^f$ is oxygen, a chloromethyl alkyl sulfide Cl—$CH_2$—$X^f$—$R^h$ wherein $X^f$ is sulphur, a suitable optionally substituted benzyl halide (e.g. chloride) such as Cl—$CH_2$-[optionally substituted phenyl], [optionally substituted phenyl]-$C(O)$—$CH_2$-[halogen e.g. Cl], $C_1$-$C_6$alkoxy-$C(O)$—$CH_2$-[halogen e.g. Cl], $C_1$-$C_6$alkoxy-$C(O)$—CH=CH-[halogen e.g. Cl], a suitable alkenyl or alkynyl halide (e.g. chloride) such as $C_2$-$C_7$alken-1-yl-$CH_2$-[halogen e.g. Cl] or $C_2$-$C_7$alkyn-1-yl-$CH_2$-[halogen e.g. Cl], or another organic halide suitable for preparing a (non-carbonyl, non-thiocarbonyl carbon)-linked G (or G1) group; or (b) [e.g. to prepare carbonyl-carbon-linked or thiocarbonyl-carbon-linked G groups] with an acylating agent such as a carboxylic acid, HO—$C(X^a)R^a$, wherein $X^a$ is oxygen, an acid chloride, Cl—$C(X^a)R^a$, wherein $X^a$ is oxygen, or an acid anhydride, $[R^aC(X^a)]_2O$, wherein $X^a$ is oxygen, an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—C($X^d$)—N($R^c$)—$R^d$ (wherein $X^d$ is sulfur and with the proviso that neither $R^c$ or $R^d$ is hydrogen), or a chloroformate, Cl—C($X^b$)—$X^c$—$R^b$ (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$ (wherein $X^b$ and $X^c$ are sulfur), or an isothiocyanate, $R^c$N=C=S; or (c) by sequential treatment with carbon disulfide and an alkylating agent; or (d) with a phosphorylating agent such as a phosphoryl chloride, Cl—P($X^e$)($R^f$)—$R^g$; or (e) with a sulfonylating agent such as a sulfonyl chloride Cl—SO$_2$—$R^e$, preferably in the presence of at least one equivalent (i.e. mole equivalent) of base.

Where substituent $R^{33}$ is not equal to substituent $R^{36}$, and/or where $R^{34}$ and $R^{35}$ taken together are an asymmetric chain, these reactions may produce, in addition to a compound of formula I, a second compound of formula (IAA).

This invention covers both a compound of formula (I), wherein Q is Q2, and a compound of formula (IAA), together with mixtures of these compounds in any ratio.

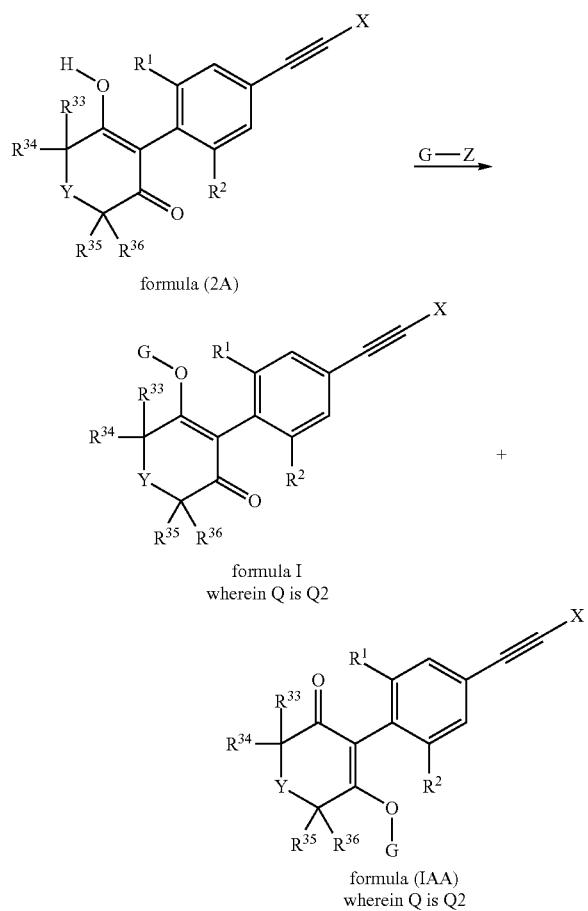

formula (2A)

formula I
wherein Q is Q2 formula (IAA)
wherein Q is Q2

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected e.g. by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (2A) may be treated with an acylating agent preferably in the presence of at least one equivalent (i.e. mole equivalent) of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected e.g. using a phosphoryl halide or thiophosphoryl halide and a base e.g. by procedures analogous to those described by L. Hodakowski, U.S. Pat. No. 4,409,153.

Sulfonylation of a compound of formula (2A) may be achieved e.g. using an alkyl or aryl sulfonyl halide, preferably in the presence of at least one equivalent (i.e. mole equivalent) of base, for example by the procedure of C. Kowalski and K. Fields, J. Org. Chem., (1981), 46, 197-201.

Compounds of formula (2A), wherein Y is S(O) or S(O)$_2$ may be prepared from compounds of formula (2A) wherein Y is S by oxidation, e.g. according to a procedure analogous to that of E. Fehnel and A. Paul, J. Am. Chem. Soc., (1955), 77, 4241-4244.

A compound of formula (2A), wherein Y is O, S, C(O) or CR$^{38}$R$^{39}$ may be prepared via the cyclisation of a compound of formula (2B), preferably in the presence of an acid or base, and optionally in the presence of a suitable solvent, e.g. by analogous methods to those described by T. Wheeler, U.S. Pat. No. 4,209,532. The compounds of the formula (2B) have been particularly designed as intermediates in the synthesis of the compounds of the formula I wherein Q is Q2, and a further aspect of the present invention provides a compound of formula (2B) (shown below). Compounds of formula (2B) wherein R is hydrogen or C$_1$-C$_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane. A compound of formula (2B) wherein R is alkyl (preferably methyl or ethyl) may also be cyclised under basic conditions in the presence of at least one equivalent (i.e. mole equivalent) of a strong base in a solvent such as tetrahydrofuran, toluene, dimethylsulfoxide or N,N-dimethylformamide. Suitable bases include potassium tert-butoxide, lithium diisopropylamide, sodium bis(trimethylsilyl)amide or sodium hydride. A compound of formula (2B), wherein R is alkyl, may be produced from a compound of formula (2B), wherein R is H, by esterification under known conditions (for example by treatment with an alcohol, R—OH, in the presence of an acid catalyst).

described by, for example, T. Wheeler, U.S. Pat. No. 4,209,532. Alternatively, a compound of formula (2B), wherein R is alkyl or H may be prepared from a compound of formula (2C), wherein R' is alkyl (preferably methyl), through a Krapcho decarboxylation procedure, e.g. under known conditions using known reagents (see for example G. Quallich, P. Morrissey, Synthesis, (1993), (1), 51-53).

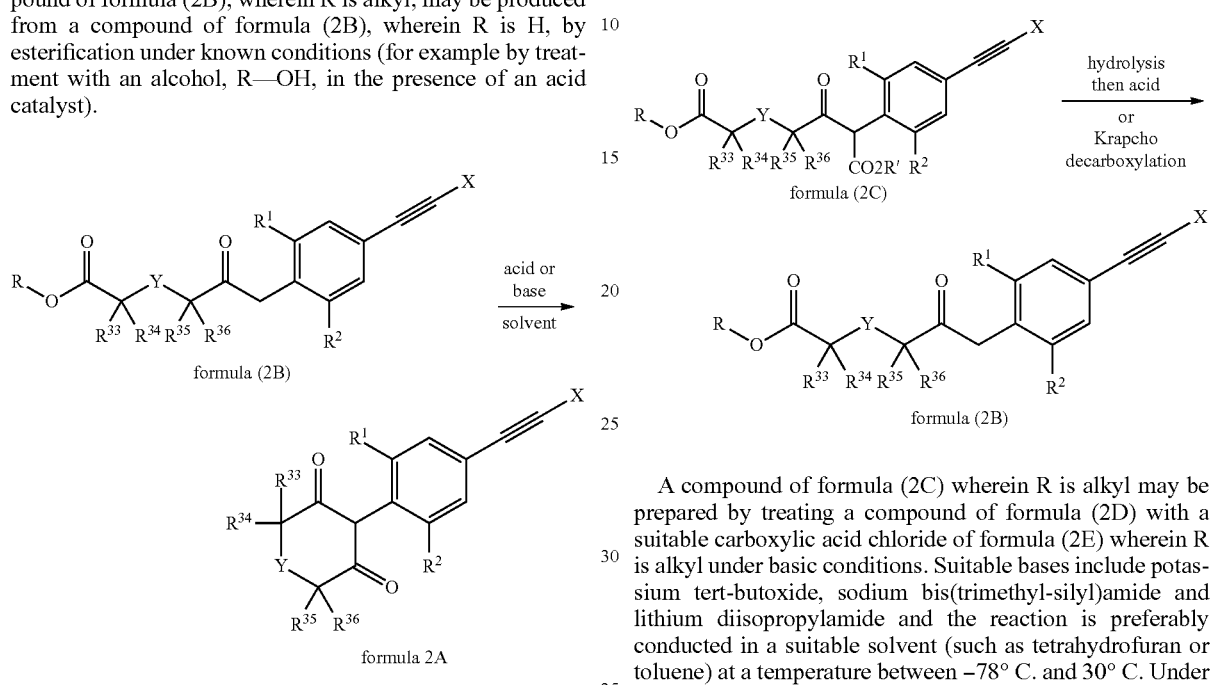

formula (2B)

formula 2A

A compound of formula (2B), wherein R is H, may be prepared by hydrolysis of a compound of formula (2C)

formula (2C)

formula (2B)

A compound of formula (2C) wherein R is alkyl may be prepared by treating a compound of formula (2D) with a suitable carboxylic acid chloride of formula (2E) wherein R is alkyl under basic conditions. Suitable bases include potassium tert-butoxide, sodium bis(trimethyl-silyl)amide and lithium diisopropylamide and the reaction is preferably conducted in a suitable solvent (such as tetrahydrofuran or toluene) at a temperature between −78° C. and 30° C. Under similar conditions a compound of formula (2C), wherein R is H, may be prepared from a suitable anhydride of formula (2F).

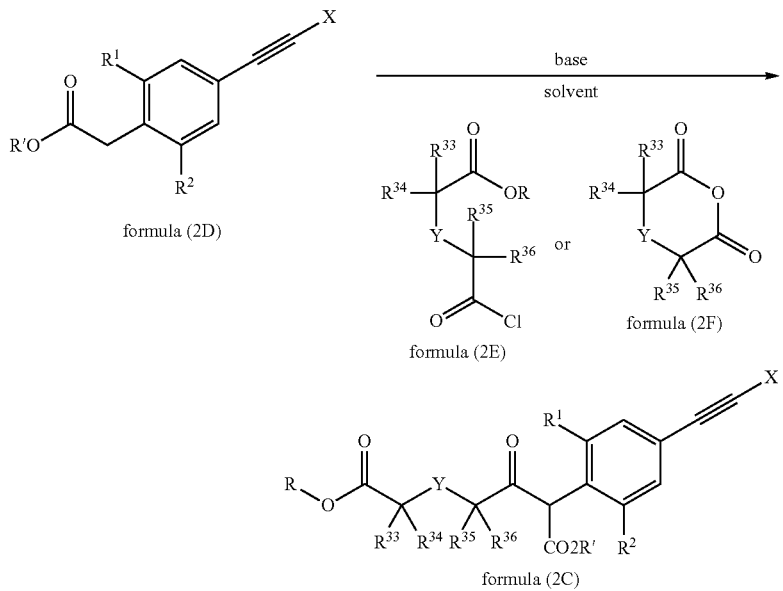

formula (2D)

formula (2E)

formula (2F)

formula (2C)

wherein R is H or alkyl and R' is alkyl (preferably methyl or ethyl), followed by acidification of the reaction mixture to effect decarboxylation, e.g. by similar processes to those Compounds of formula (2E) and formula (2F) are known (see, for example T. Terasawa and T. Okada, J. Org. Chem., (1977), 42 (7), 1163-1169; G. Bennett, W. Houlihan, R.

Mason; R. Engstrom, J. Med. Chem., (1976), 19 (5), 709-14; L. J. J. Hronowski, Lucjan W. A. Szarek, Canadian Journal of Chemistry (1988), 66(1), 61-70; S. F. Birch, V. E. Gripp, D. T. McAllan, W. S. Nathan, Journal of the Chemical Society (1952), 1363-8; S. Kitamura, T. D. Aicher, Gonzales, Steve; Y. Le Huerou, S. A. Pratt, Y. Nakada, WO 2008011130; O. Jentzer, M. Guglieri, WO 2009092795), or may be made by similar methods from commercially available starting materials.

Compounds of formula (2D), wherein X is methyl and R' is $C_1$-$C_4$alkyl, can be prepared by reacting compounds of formula (2G) with propyne in the presence of a suitable catalyst, optionally a suitable additive, optionally in a suitable solvent at a suitable temperature. Suitable catalysts include transition metal salts or complexes of transition metal salts (for example palladium acetate, bis(triphenylphosphine)palladium(II)dichloride, tetrakis(triphenyl-phosphine)palladium(0), bis(triphenylphosphine) nickel(II)dichloride and tris(acetylacetonato)iron(III)), in an amount of typically 0.001-25 mole % with respect to a compound of formula (2G). Suitable additives include copper salts, for example copper(I) iodide in an amount of typically 0.001-50 mole % with respect to a compound of formula (2G), and tetraalkyl ammonium salts. Suitable bases include diethylamine, triethylamine, piperidine and pyrrolidine, and suitable solvents include 1,4-dioxane, N,N-dimethylacetamide or N,N-dimethylformamide. Preferably the reaction is carried out using 0.05-10 mole % bis(triphenylphosphine)palladium(II)dichloride (with respect to a compound of formula (2G)), 0.05-10 mole % triphenylphosphine (with respect to a compound of formula (2G)), 0.05-25 mole % copper(I) iodide (with respect to a compound of formula (2G)), 5-200 mole % tetrabutyl ammonium iodide (with respect to a compound of formula (2G)), triethylamine and N,N-dimethylformamide at a temperature between 25° C. to 150° C. Such a reaction is an example of a Sonogashira coupling and similar reactions are known in the literature (see for example F. Labrie, S. Gauthier, J. Cloutier, J. Mailhot, S. Potvin, S. Dion, J-Y. Sanceau, WO 2008124922; M. S. Viciu, S. P. Nolan, Modern Arylation Methods (2009), 183-220; R. Chinchilla, C. Najera, Chemical Reviews (2007), 107(3), 874-922; I. P. Beletskaya, G. V. Latyshev, A. V. Tsvetkov, N. V. Lukashev, Tetrahedron Letters (2003), 44(27), 5011-5013 and J. Mao, G. Xie, M. Wu, J. Guo, S. Ji, Advanced Synthesis & Catalysis (2008), 350(16), 2477-2482). In an alternative approach a compound of formula (2D) may be prepared from a compound of formula (2G) by reaction with a propynyl transfer reagent such as 1-propynyllithium, 1-propynylmagnesium bromide, 1-propynylmagnesium chloride, 1-propynylmagnesium iodide, 1-propynylzinc chloride, 1-propynylzinc bromide, 1-propynylzinc iodide, tributylpropynylstannane, 1-propyne-1-boronic acid (or ester thereof), 2-butynoic acid or 1-(trimethylsilyl)propyne, with a transition metal catalyst system under suitable conditions (see for example P. Wessig, G. Mueller, C. Pick, A. Matthes, Synthesis (2007), (3), 464-477; J. H. Chaplin, G. S. Gill, D. W. Grobelny, B. L. Flynn, G. Kremmidiotis, WO07087684; A. Akao, T. Tsuritani, S. Kii, K. Sato, N. Nonoyama, T. Mase, N. Yasuda, Synlett (2007), (1), 31-36. A. Coelho Coton, E. Sotelo Perez, F. Guitian Rivera, A. Gil Gonzalez, WO 2011048247; C. H. Oh, S. H. Jung, Tetrahedron Letters (2000), 41(44), 8513-8516; D. Zhao, C. Gao, X. Su, Y. He, J. You, Y. Xue, Chemical Communications (2010), 46(47), 9049-9051; C. Yang, S. P. Nolan, Organometallics (2002), 21(6), 1020-1022). In another set of preferred conditions a compound of formula (2G) is reacted with 1-propynylmagnesium bromide in the presence of 0.05-10 mole % bis(triphenylphosphine) palladium(II)dichloride (with respect to a compound of formula (2G)), in tetrahydrofuran at a temperature between 25° C. and 100° C., as described by J. H. Chaplin, G. S. Gill, D. W. Grobelny, B. L. Flynn, G. Kremmidiotis, WO 07087684. Compounds of formula (2G) are known, or can be prepared by known methods using known reagents.

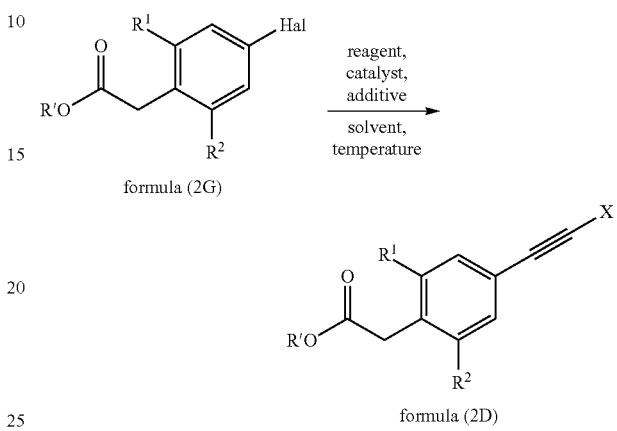

formula (2G)

formula (2D)

Compounds of formula (2D), wherein X is chlorine and R' is $C_1$-$C_4$alkyl, can be prepared from compounds of formula (2H) or compounds of formula (2I). In one approach a compound of formula (2H) is first deprotonated with a base such as butyllithium, sodium hydride, lithium diisopropylamide or ethylmagnesium bromide, then reacted with a chlorine source such as N-chloro succinimide, chlorine or carbon tetrachloride. The specific chlorine source is selected to provide the required chloro-acetylene. Similar reactions and conditions are reported in the literature (see for example M. Tajbakhsh, S. Habibzadeh, Letters in Organic Chemistry (2007), 4(7), 512-514; D. Sud, T. J. Wigglesworth, N. R. Branda, Angewandte Chemie, International Edition (2007), 46(42), 8017-8019; M. A. P. Martins, D. J. Emmerich, C. M. P. Pereira, W. Cunico, M. Rossato, N. Zanatta, H. G. Bonacorso, Tetrahedron Letters (2004), 45(25), 4935-4938; A. Poloukhtine, V. Rassadin, A. Kuzmin, V. V. Popik, Journal of Organic Chemistry (2010), 75(17), 5953-5962; C. R. Hickenboth, J. D. Rule, J. S. Moore, Tetrahedron (2008), 64(36), 8435-8448; F. H. M. Graichen, A. C. Warden, S. Kyi, M. S. O'Shea, Australian Journal of Chemistry (2010), 63(4), 719-722; and M. L. Narayana, M. L. N. Rao, M. Periasamy, Synthetic Communications (1995), 25(15), 2295-9).

In another approach a compound of formula (2D), wherein X is chlorine and R' is $C_1$-$C_4$alkyl, can be prepared from a compound of formula (2H) by treatment with a mixture of reagents that are known to promote chlorination, such as potassium carbonate, tetrabutylammonium bromide and carbon tetrachloride (see for example T. Matsuda, S. Kadowaki, Y. Yamaguchi, M. Murakami, Chemical Communications (2008), (24), 2744-2746), pyridine and chlorine (see for example R. B. Gutsulyak, V. N. Britsuk, L. A. Kostrikina, Y. Serguchev, Ukrainskii Khimicheskii Zhurnal (1993), 59(10), 1062-7), silver nitrate and N-chloro succinimide, N-chloro succinimide and hexamethylphosphoramide (see for example G. Pangon, J. L. Philippe, P. Cadiot, Comptes Rendus des Seances de l'Academie des Sciences, Serie C: Sciences Chimiques (1973), 277(18), 879-81), and/or perchloric acid and acetic acid (see for example J. P. Montheard, M. Camps, M. Chatzopoulos, M. O. A. Yahia, R. Guilluy, D. Deruaz, Journal of Chemical Research, Synopses (1983), (9), 224-5). Conditions are selected to provide the required chloro-acetylene. When X is chlorine, preferred conditions include reacting a compound of formula (2H) with 1-5 mole equivalents of N-chloro succinimide and 0.05-50 mole % silver acetate (with respect to a compound of formula (2H)) in acetone at a temperature between 25° C. and 100° C.

Compounds of formula (2I), wherein R' is $C_1$-$C_4$alkyl and R' is $C_1$-$C_4$alkyl, can also be directly converted to compounds of formula (2D), e.g. by treatment with isocyanuric chloride or N-chloro succinimide and silver nitrate (see for example M. H. Vilhelmsen, A. S. Andersson, M B. Nielsen, Synthesis (2009), (9), 1469-1472).

In a further approach, a compound of formula (2D) (wherein X is chlorine) can either be prepared from a compound of formula (2J) or a compound of formula (2K), by treatment with a suitable base, in a suitable solvent, at a suitable temperature. A compound of formula (2J) can be converted to a compound of formula (2D) under conditions similar to those described in the literature, for example treatment using potassium tert-butoxide in tert-butanol at a temperature between 25° C. and 150° C., or lithium 2,2,6,6-tetramethylpiperidine in tetrahydrofuran at a temperature between −25° C. and 50° C. (see for example E. Bartmann, R. Hittich, H. Plach, U. Finkenzeller, U.S. Pat. No. 5,188,759 and Indian Journal of Chemistry, Section B: Organic Chemistry Including Medicinal Chemistry, 1978, vol. 16, 1051-1054). A compound of formula (2K) can also be converted to a compound of formula (2D) under conditions similar to those described in the literature, for example by treatment with cesium carbonate in N,N-dimethylformamide at a temperature between 25° C. and 150° C., sodium

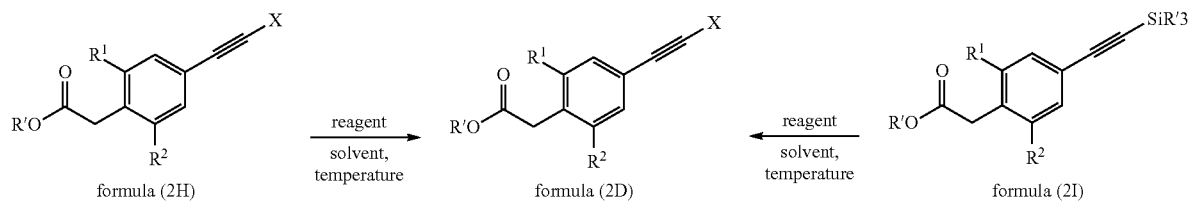

A compound of formula (2I), wherein R' is $C_1$-$C_4$alkyl and R' is $C_1$-$C_4$alkyl, can be prepared by reacting a compound of formula (2G) with a trialkylsilylacetylene, under similar conditions described previously to convert a compound of formula (2G) to a compound of formula (2D) (wherein X is methyl).

A compound of formula (2H) can either be prepared by deprotection of a compound of formula (2I) under known conditions, or by reacting a compound of formula (2G) with an ethynyl transfer reagent such as tributylstannylacetylene, lithium acetylide ethylenediamine complex, ethynylzinc bromide or ethynylmagnesium chloride in the presence of a suitable catalyst system, e.g. under conditions similar to those described previously (see for example C. Fischer, J. Methot, H. Zhou, A. J. Schell, B. Munoz, A. A. Rivkin, S. P. Ahearn, S. Chichetti, R. N. Maccoss, S. D. Kattar, M. Christopher, C. Li, A. Rosenau, W. C. Brown, WO 2010071741; M. Behler, A. Eluntlaut, C. Ferman, A. Chapuf, CN 101195641; G. Wang, G. Zhu, E. Negishi, Journal of Organometallic Chemistry (2007), 692(21), 4731-4736 and E. Negishi, M. Kotora, C. Xu, Journal of Organic Chemistry (1997), 62(25), 8957-8960).

tert-butoxide in toluene at a temperature between 25° C. and 150° C., 1,8-diazabicyclo[5.4.0]undec-7-ene in dimethylsulfoxide at a temperature between 0° C. and 50° C., or potassium tert-butoxide in tetrahydrofuran at a temperature between −78° C. and 25° C. (see for example B. C. G. Soederberg, S. P. Gorugantula, C. R. Howerton, J. L. Petersen, S. W. Dantale, Tetrahedron (2009), 65(36), 7357-7363; S-C. Lo, R. E. Harding, E. Brightman, P. L. Burn, I. D. W. Samuel, Journal of Materials Chemistry (2009). 19(20), 3213-3227; S. Wang, T. Kohn, Z. Fu, X. Y. Jiao, S. Lai, M. Schmitt, Tetrahedron Letters (2008), 49(51), 7284-7286 and M. L. G. Borst, R. E. Bulo, D. J. Gibney, Y. Alem, F. J. J. de Kanter, A. W. Ehlers, M. Schakel, M. Lutz, A. L. Spek, K. Lammertsma, Journal of the American Chemical Society (2005), 127(48), 16985-16999). Compounds of formula (2J) and (2K) (wherein X is chlorine) can be prepared from known compounds using known methods and reagents.

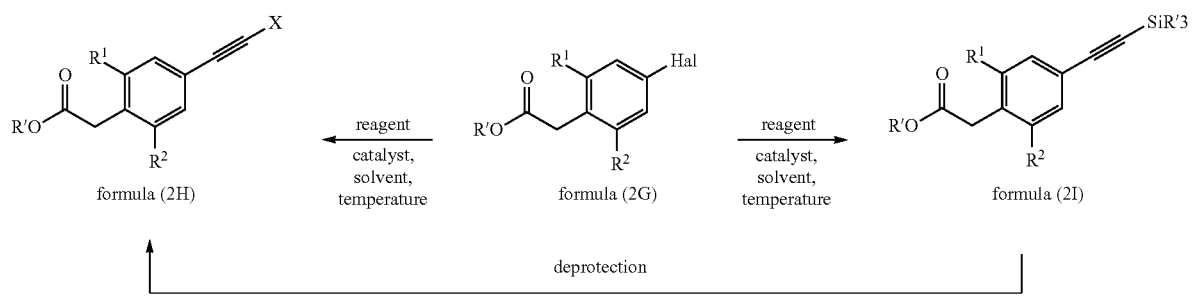

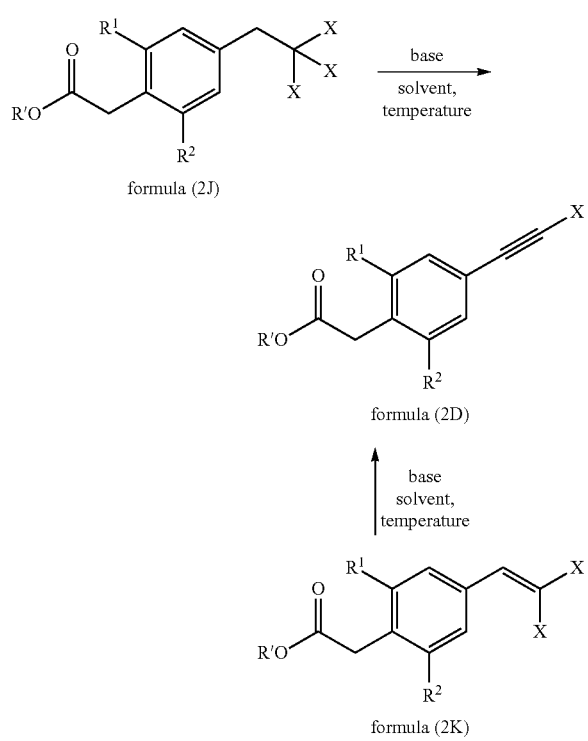
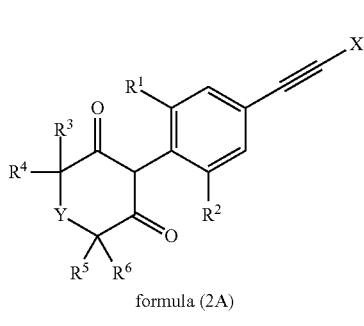
compound of formula (2L), under similar conditions described previously to convert a compound of formula (2G) to a compound of formula (2D).
In a further approach a compound of formula (2A), wherein X is methyl, can be prepared directly from a compound of formula (2G) using similar procedures to those outlined previously.
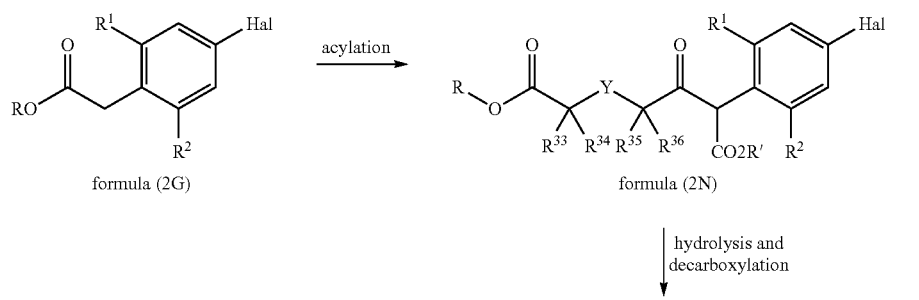
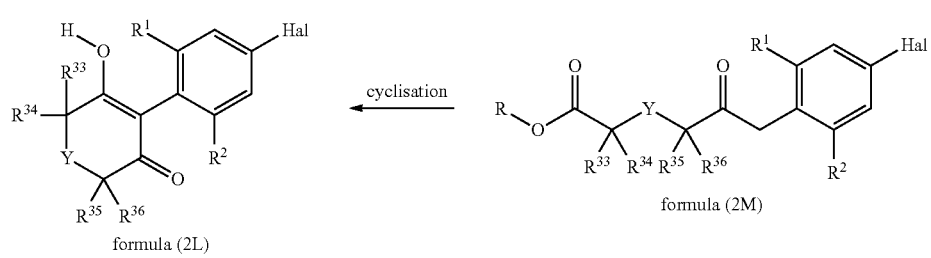

A compound of formula (2A), wherein X is chlorine, can be prepared from a compound of formula (2L), via either a compound of formula (2O) or a compound of formula (2P) (wherein R' is $C_1$-$C_4$alkyl), e.g. under similar conditions to those described previously.

can Chemical Society (2007), 129(40), 12062-12063; L. N. Michaelides, B. Darses, D. J. Dixon, Organic Letters (2011), 13(4), 664-667 and F. Gavina, S. V. Luis, P. Ferrer, A. M. Costero, J. A. Marco, Journal of Chemical Research, Synopses (1986), (9), 330-1).

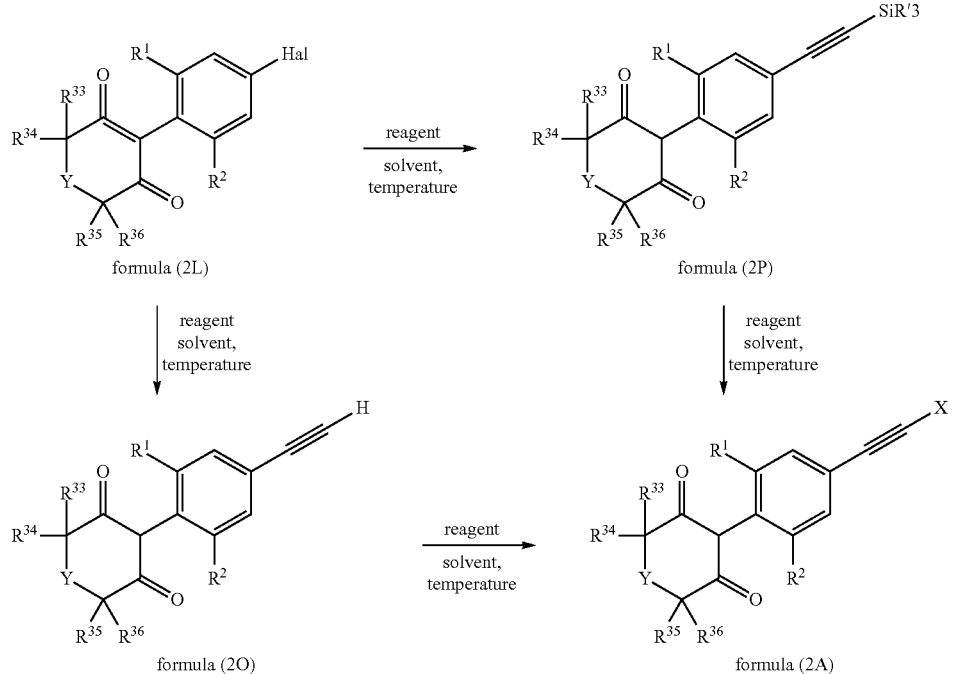

A compound of formula (2A), wherein X is chlorine, can also be prepared from a compound of formula (2Q), e.g. under conditions similar to those described for converting a compound of formula (2K) to a compound of formula (2D).

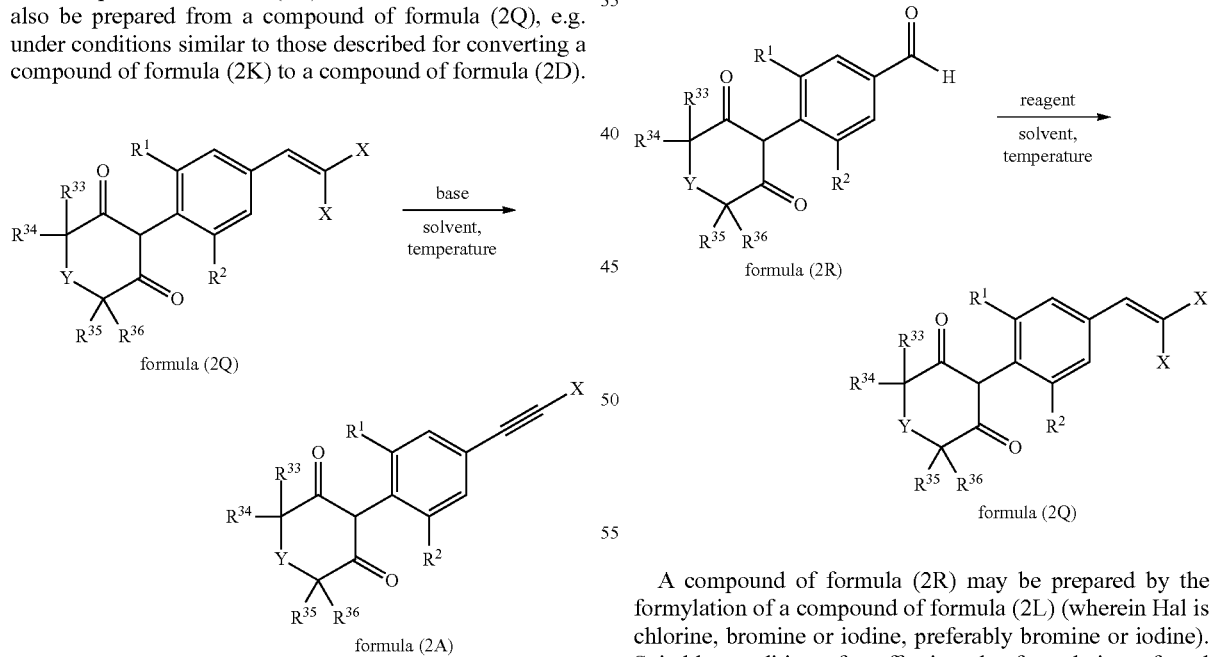

A compound of formula (2Q), wherein X is chlorine may be prepared from an aldehyde of formula (2R) by treatment with triphenylphosphine in the presence of carbon tetrachloride in a suitable solvent at a suitable temperature. Carbon tetrachloride is selected to provide the required dichloroalkene, and similar reactions are known in the literature (see for example A. Poloukhtine, V. V. Popik, Journal of the Ameri- A compound of formula (2R) may be prepared by the formylation of a compound of formula (2L) (wherein Hal is chlorine, bromine or iodine, preferably bromine or iodine). Suitable conditions for effecting the formylation of aryl halides are known, and include, for example, the treatment of an aryl halide with a suitable organometallic reagent, such as isopropyl magnesium chloride, n-butyllithium, sec-butyllithium or tert-butyllithium, or by treatment with a suitable alkali metal or alkali earth metal such as lithium or magnesium in a suitable solvent, such as diethyl ether, dimethoxyethane or tetrahydrofuran. The resulting arylmetal reagent is then reacted with a suitable formylating agent such as N,N-dimethylformamide or N-formylmorpholine. Alternatively a compound of formula (2R) may be prepared from a compound of formula (2L) (wherein Hal can also be a pseudohalogen such as triflate) by treatment with a carbonylating agent (such as carbon monoxide in the presence of a suitable catalyst system, base, and reducing agent (see for example L. Ashfield and C. Barnard, Org. Process Res. Dev., 11 (1), 39-43, 2007).

In an alternative approach, a compound of formula I, wherein Q is Q2, X is methyl, and wherein G is preferably substituted alkyl (e.g. optionally substituted phenyl-$CH_2$— or heteroaryl-$CH_2$—), or hydrogen, or methyl or ethyl (the latter two are not within formula I but can be converted to G=H later), may be prepared from a boronic acid or boronic ester of formula (2S) by treatment with either 1-bromo-1-propyne or 1-iodo-1-propyne, preferably in the presence of a suitable catalyst system, a suitable base and/or a suitable solvent and/or at a suitable temperature. Similar reactions are known in the literature, and preferred conditions involve reacting a compound of formula (2S) with 1-iodo-propyne in the presence of 0.005-25 mole % palladium(II) chloride (with respect to a compound of formula (2S)) and 1-10 equivalents (i.e. mole equivalents) of potassium carbonate, preferably in a mixture of toluene, water and methanol at a temperature between 50° C.-150° C., as described by Y. Shi, X. Li, J. Liu, W. Jiang, L. Sun, Tetrahedron Letters (2010), 51(28), 3626-3628. A compound of formula (2T), wherein G is preferably methyl or ethyl and R″ is $C_1$-$C_4$alkyl, may be prepared under similar conditions using either 1-bromo-2-(trimethylsilyl)acetylene or 1-iodo-2-(trimethylsilyl)acetylene as the coupling partner. Compounds of formula (2A) and (2P) may be prepared from compounds of formula I, wherein Q is Q2, and (2T) respectively, by hydrolysis of the enol ether.

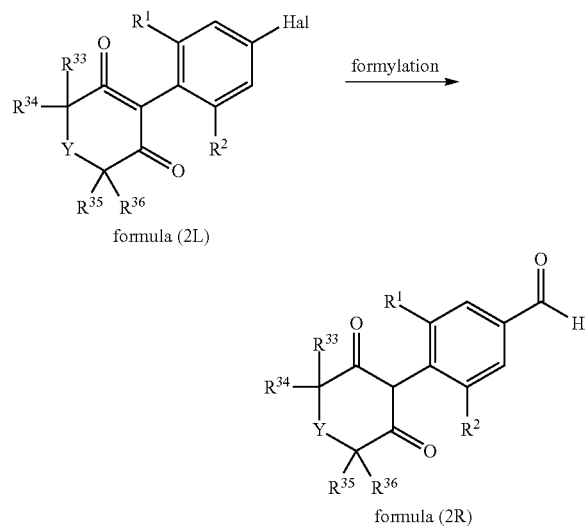

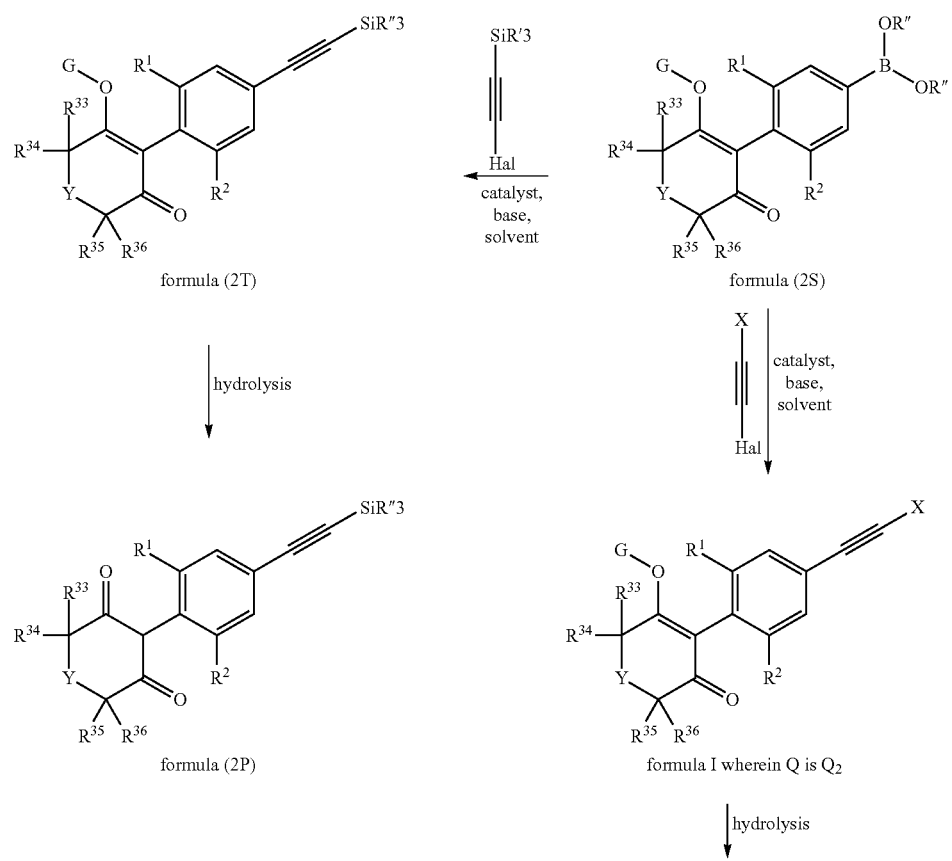

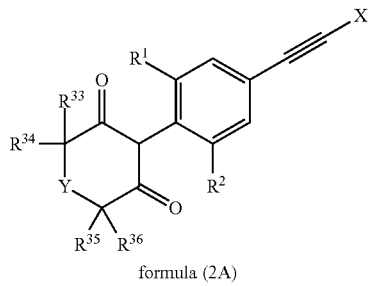

formula (2A)

In one approach, a compound of formula (2S) may be prepared from a compound of formula (2L) (wherein Hal is preferably iodine or bromine), preferably by treatment with a suitable base, such as sodium hydride, potassium hydride or isopropylmagnesium chloride, in a suitable solvent, such as tetrahydrofuran or diethyl ether, followed by a metal-halogen exchange reaction, preferably by treatment with an alkyllithium reagent such as n-butyllithium, sec-butyl-lithium or tert-butyllithium, or an organomagnesium reagent such as isopropyl magnesium chloride, and subsequent treatment with a trialkylborate, B(OR")$_3$, preferably trimethylborate, to give the corresponding boronate ester of formula (2S).

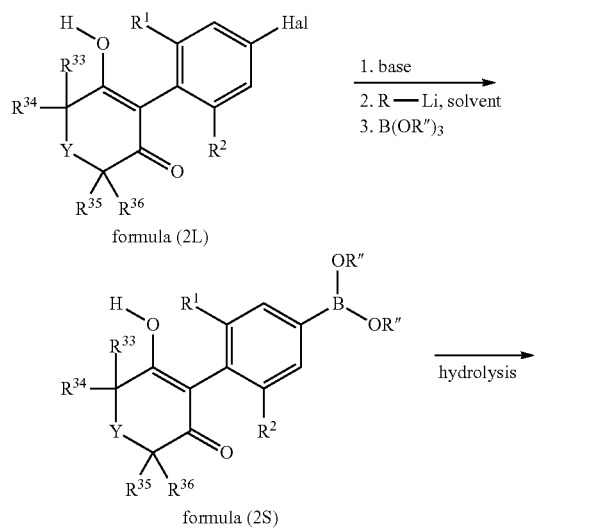

formula (2L)

formula (2S)

In an alternative approach, a compound of formula (2U) may be prepared from a compound of formula (2V), wherein G is preferably substituted alkyl (e.g. optionally substituted phenyl-CH$_2$— or heteroaryl-CH$_2$—), or methyl or ethyl (the latter two are not within the G definition in formula I but can be converted to G=H later), by C—H borylation with a suitable borylating agent, a suitable catalyst system, in a suitable solvent at a suitable temperature. Suitable catalysts include 1,5-cyclooctadiene)(methoxy)iridium(I) dimer in combination with 4,4'-di-tert-butyl-2,2'-dipyridyl, suitable borylating agents include bis(pinacolato)diboron or pinacol borane, and suitable solvents include hexane, octane, tetrahydrofuran and methyl tert-butyl ether. Similar examples are known in the literature (see for example J. F. Hartwig, Chemical Society Reviews (2011), 40(4), 1992-2002 and T. Ishiyama, N. Miyaura, Pure and Applied Chemistry (2006), 78(7), 1369-1375). Preferred conditions include treating a compound of formula (2V) with 0.05-10 mole % 1,5-cyclooctadiene)(methoxy)iridium(I) dimer (with respect to a compound of formula (2V)), 0.05-10 mole % 4,4'-di-tert-butyl-2,2'-dipyridyl (with respect to a compound of formula (2V)), and 1-2 equivalents (i.e. mole equivalents) of bis(pinacolato)diboron (with respect to a compound of formula (2V)) in methyl tert-butyl ether at a temperature between 50° C.-150° C., optionally under microwave irradiation, as described by P. Harrisson, J. Morris, T. B. Marder, P. G. Steel, Organic Letters (2009), 11(16), 3586-3589.

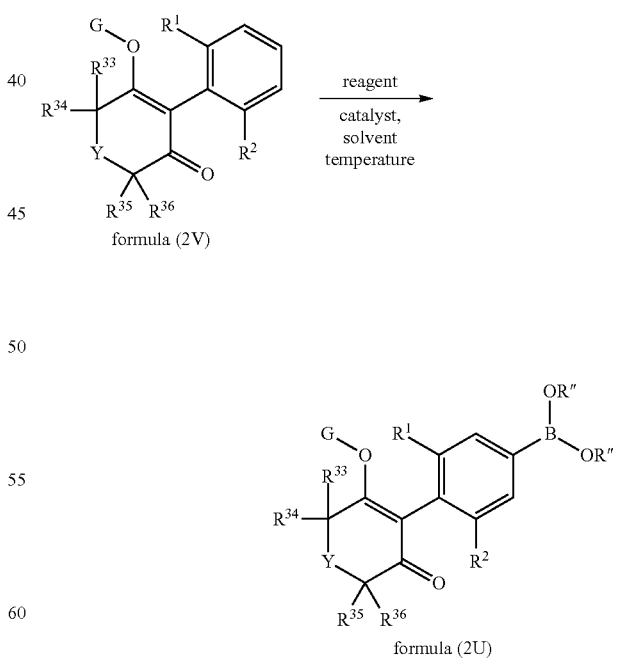

formula (2V)

formula (2U)

Compounds of formula (2W) can be prepared from compounds of formula (2X) using similar procedures described previously, starting from compounds of formula (2Z) which are known compounds.

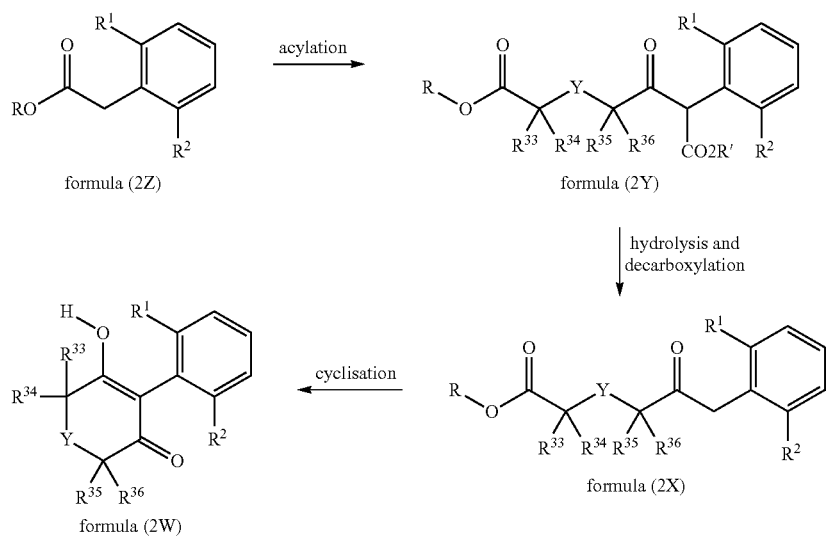

In a further approach to the compounds of the invention, a compound of formula (2A), wherein X is methyl, may be prepared via the rearrangement of a compound of formula (2AA), in the presence of a reagent which promotes rearrangement. Preferably, the reagent which promotes rearrangement is (i) a metal alkoxide (e.g. sodium or potassium methoxide), preferably in an amount equal to or greater than 100 mole % with respect to compound of formula (2AA), or is (ii) a cyanide anion, for example 0.001-25 mole % potassium cyanide or 0.001-25 mole % sodium cyanide with respect to a compound of formula (2AA), or is (iii) a cyanohydrin, preferably 0.001-25 mole % acetone cyanohydrin with respect to a compound of formula (2AA). This reaction is preferably performed in a suitable solvent (e.g. organic solvent, e.g. N, N-dimethylformamide) and/or at a suitable temperature (typically 25-150° C.). More preferably, a compound of formula (2A) wherein X is methyl is prepared by treating a compound of formula (2AA) with 1-3 equivalents (i.e. mole equivalents) of sodium methoxide in N, N-dimethylformamide at a temperature between 50° C. and 100° C.

In one approach to a compound of formula (2AA), the compound of formula (2AA), wherein X is methyl, may be prepared from a compound of formula (2AB) by treatment with a catalyst system which promotes lactonisation, such as palladium(II)dichloride, gold(I) chloride or silver carbonate, preferably 0.001-50 mole % silver carbonate with respect to a compound of formula (2AB), in the presence of a suitable solvent, for example acetonitrile, at a suitable temperature (typically 25° C. to 150° C.), and optionally under microwave irradiation. Similar lactonisations are known in the literature (see for example WO 2008/071405, P. Huang and W. Zhou, Tetrahedron Asymmetry (1991), 2 (9), 875-878; and H. Harkat, J-M. Weibel, P. Pale, Tetrahedron Letters (2006), 47(35), 6273-6276).

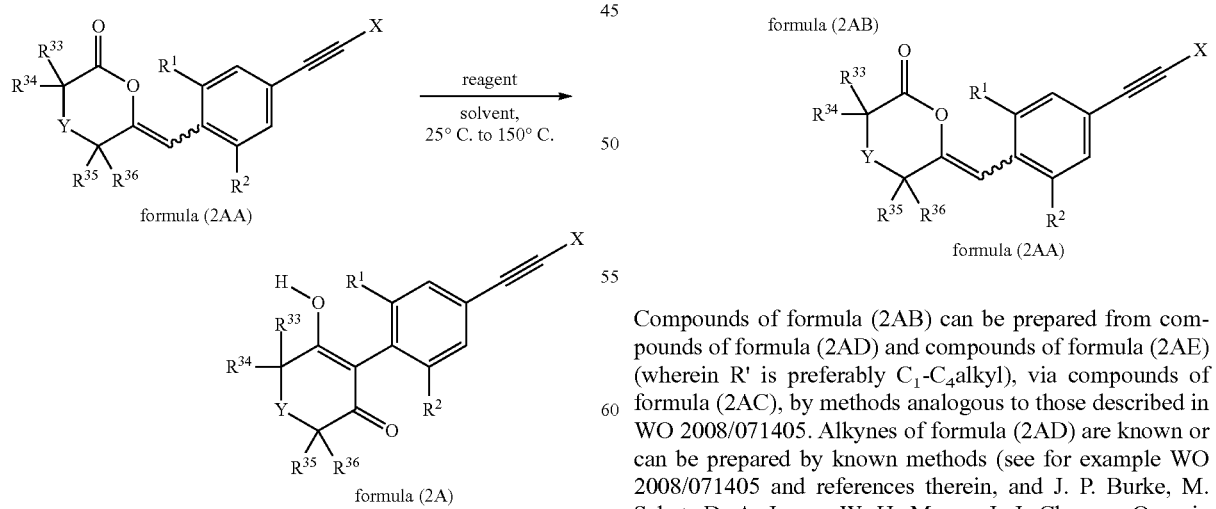

Compounds of formula (2AB) can be prepared from compounds of formula (2AD) and compounds of formula (2AE) (wherein R' is preferably $C_1$-$C_4$alkyl), via compounds of formula (2AC), by methods analogous to those described in WO 2008/071405. Alkynes of formula (2AD) are known or can be prepared by known methods (see for example WO 2008/071405 and references therein, and J. P. Burke, M. Sabat, D. A. Iovan, W. H. Myers, J. J. Chruma, Organic Letters (2010), 12(14), 3192-3195). Compounds of formula (2AE) are either known compounds or can be prepared from known reagents using known methods.

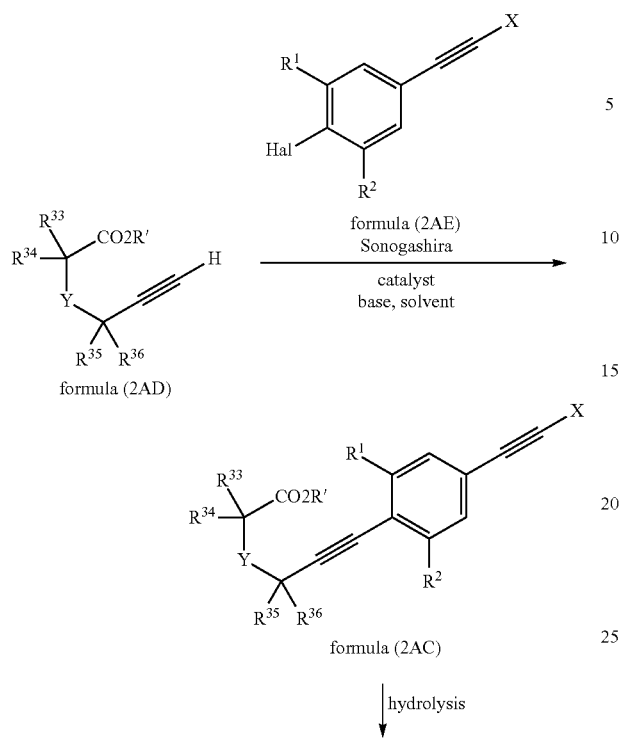
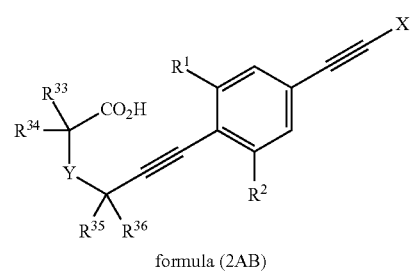
formula (2AB)
A compound of formula (2P), wherein R' is $C_1$-$C_4$alkyl, can also be prepared using similar chemistry to that described previously, starting with a compound of formula (2AD) and a compound of formula (2AI) which are both known in the literature or can be prepared using known methods and known reagents.
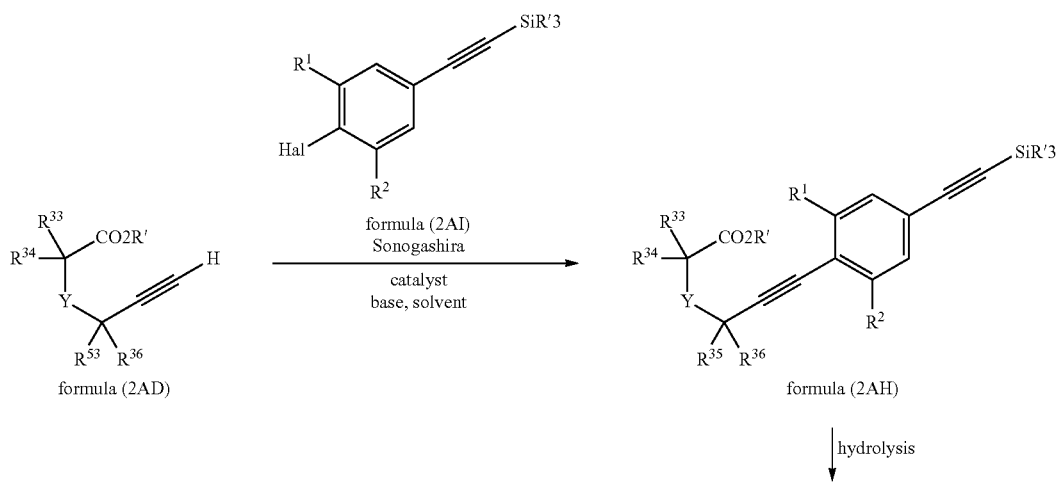
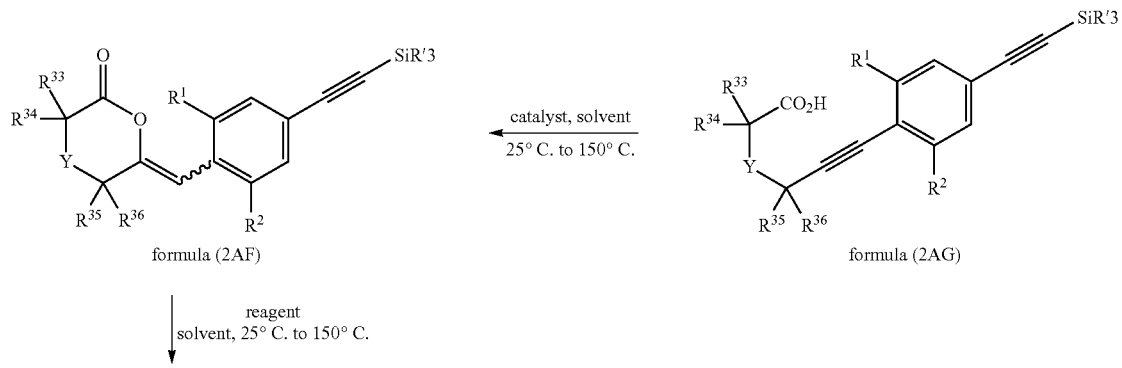

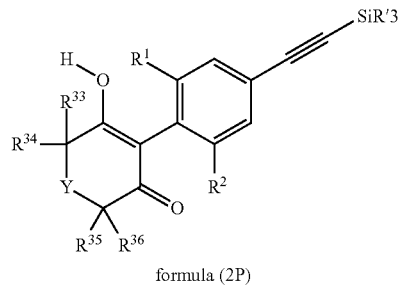
formula (2P)
Similarly, a compound of formula (2L) can be prepared from a compound of formula (2AJ) using similar chemistry to that described previously.
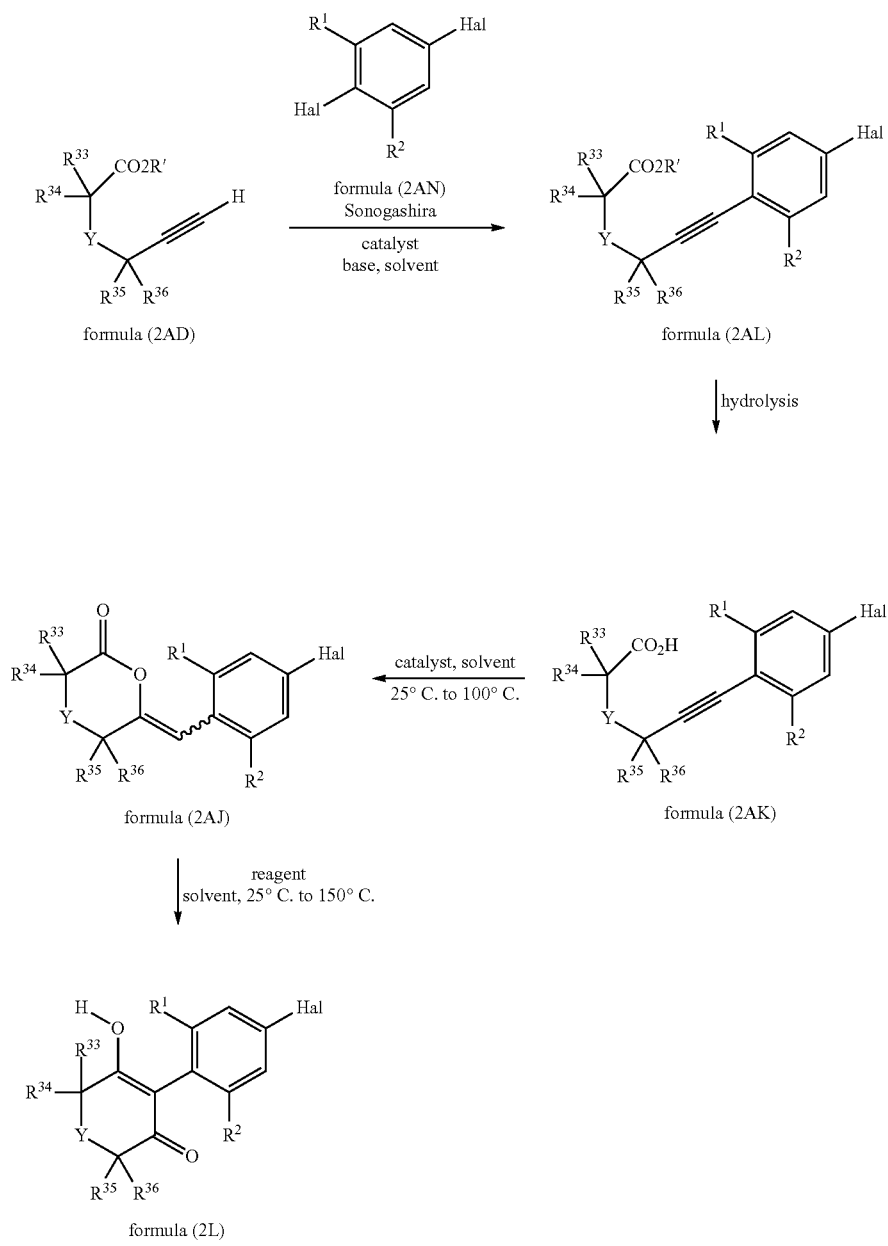

Similarly, a compound of formula (2W) can be prepared from a compound of formula (2AO) using similar chemistry to that described previously.
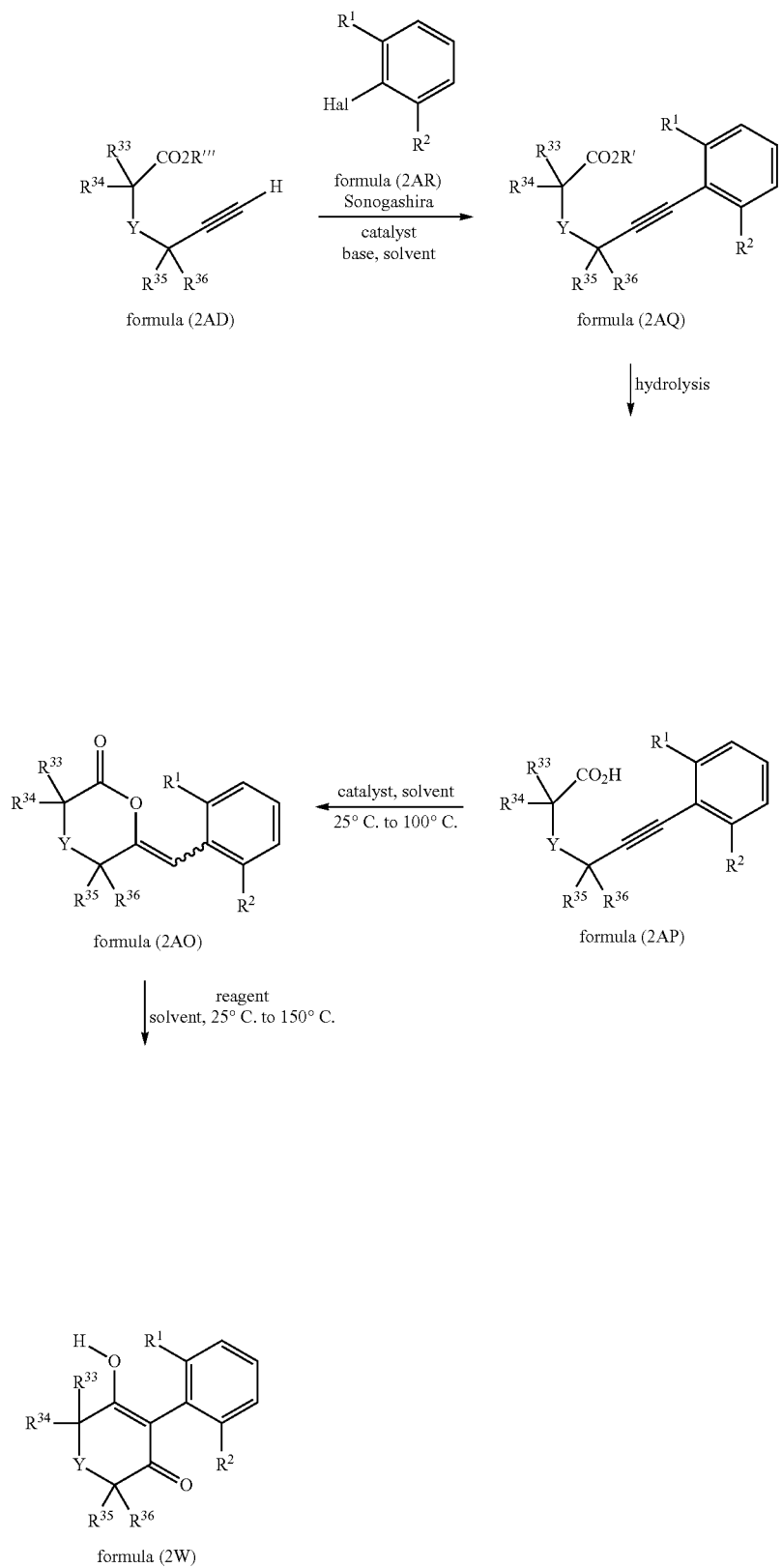

In a second approach, a compound of formula (2AA), wherein X is methyl, may be prepared via the Baeyer-Villiger oxidation of a compound of formula (2AS), preferably in a suitable solvent and/or at a suitable temperature (in particular from 0° C. to 100° C.), and optionally in the presence of a suitable catalyst system (such as selenium dioxide). Suitably, an oxidant comprising peracetic acid or hydrogen peroxide is used. Preferred conditions are hydrogen peroxide and catalytic selenium dioxide (0.001-25 mole %) in tert-butanol at a temperature of from 0° C. to 100° C., as described by J. A. Guzman, V. Mendoza, E. Garcia, C. F. Garibay, L. Z. Olivares, L. A. Maldonado, Synthetic Communications (1995), 25(14), 2121-33.

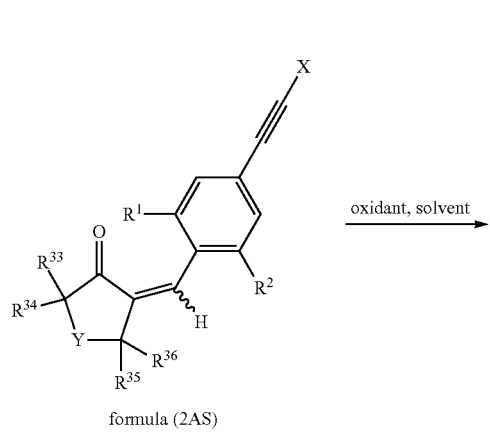

formula (2AS)

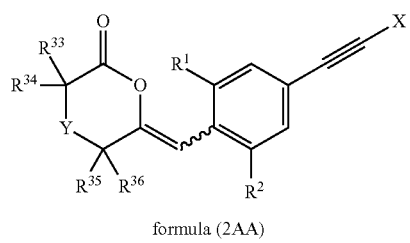

formula (2AA)

A compound of formula (2AS), wherein X is methyl, may be prepared from a compound of formula (2AU) by condensation with a benzaldehyde of formula (2AT), in the presence of a suitable base and optionally in the presence of a suitable solvent (for similar examples see WO 2010/136431; A. Lagrange, S. Forestier, G. Lang and B. Luppi, EP368717 A1; D. C. Rowlands, U.S. Pat. No. 2,776,239; E. Tamate, Journal of the Chemical Society of Japan, (1957), 78, 1293-7; R. Hernandez, D. Melian, T. Prange, E. Suarez, Heterocycles (1995), 41(3), 439-54; and J. Sotiropoulos, N. El Batouti, A. M. Lamazouere, Journal of Heterocyclic Chemistry (1987), 24(4), 907-12).

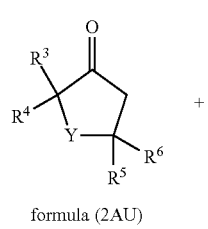

formula (2AU)

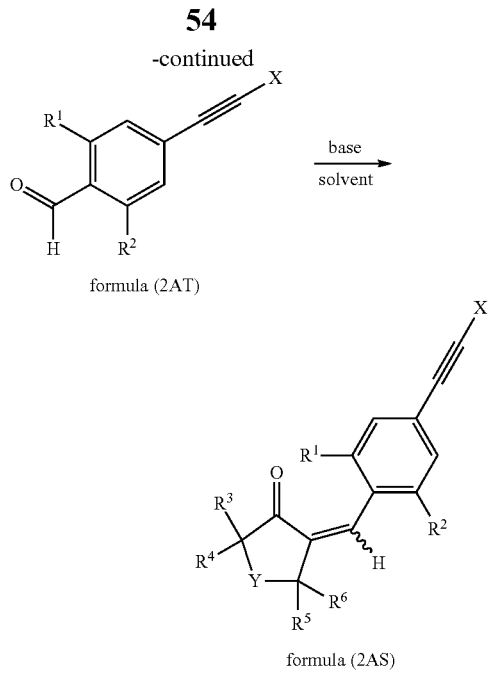

formula (2AT)

formula (2AS)

Preferably the base is a metal hydroxide, such as sodium hydroxide or potassium hydroxide, metal alkoxide such as sodium methoxide, sodium ethoxide or potassium tert-butoxide, or metal amide such as sodium amide. Preferably the solvent is dimethoxyethane, dioxane, tetrahydrofuran, diethyl ether or an alkyl alcohol, such as methanol, ethanol, isopropanol or tert-butanol.

Compounds of formula (2AU), wherein Y is O and or $CR^{38}R^{39}$, are known compounds (see for example X. Ye, M. D. Johnson, T. Diao, M. H. Yates, S. S. Stahl, Green Chemistry (2010), 12(7), 1180-1186; M. Newman and W. Reichle, Org. Synth. Coll. Vol. V., (1973), 1024; Y. Zal'kind, E. Venus-Danilova and V. Ryabtseva, Russian Journal of General Chemistry, (1950), 20, 2222-9; M. Bertrand, J. Dulcere, G. Gil, J. Grimaldi and P. Sylvestre-Panthet, Tetrahedron Letters (1976), (18), 1507-8), or may be prepared from known compounds by known methods.

Compounds of formula (2AU), wherein Y is C(O), are known compounds (see for example N. J. Turro, D. R. Morton, E. Hedaya, M. E. Kent, P. D'Angelo, P. Schissel, Tetrahedron Letters (1971), (27), 2535-8; P. A. Krapcho, D. R. Rao, M. P. Silvon, B. Abegaz, Journal of Organic Chemistry (1971), 36(25), 3885-90; S. N. Crane, T. J. Jenkins, D. J. Burnell, Journal of Organic Chemistry (1997), 62(25), 8722-8729; S. N. Crane, D. J. Burnell, Journal of Organic Chemistry (1998), 63(4), 1352-1355; S. N. Crane, D. J. Burnell, Journal of Organic Chemistry (1998), 63(16), 5708-5710; C. E. Elliott, D. O. Miller, D. J. Burnell, Journal of the Chemical Society, Perkin Transactions 1 (2002), (2), 217-226), or may be prepared from known compounds by known methods.

Compounds of formula (2AU), wherein Y is S, S(O) or $S(O)_2$ are known compounds (see for example E. R. Buchman, H. Cohen, Journal of the American Chemical Society (1944), 66, 847-8; A. W. D. Avison, F. Bergel, J. W. Haworth, U.S. Pat. No. 2,408,519: K. G. Mason, M. A. Smith, E. S. Stern, E J. A. Elvidge, Journal of the Chemical Society [Section] C: Organic (1967), (21), 2171-6; T. A. Magee, Thomas A. DE 2033454; I. Tabushi, Y. Tamaru, Z. Yoshida, T. Sugimoto, Journal of the American Chemical Society (1975), 97(10), 2886-91; P. E. Aldrich, G. H. Berezin, B. I. Dittmar, I. Bruce, DE 2516554; I. Tabushi, Y. Tamaru, Z. Yoshida, Bulletin of the Chemical Society of Japan (1978), 51(4), 1178-82; D. N. Reinhoudt, J. Geevers, W. P. Trompenaars, S. Harkema, G. J. Van Hummel, Journal of Organic Chemistry (1981), 46(2), 424-34; F. Duus, Synthesis (1985), (6-7), 672-4; J. Schatz, Science of Synthesis (2002), 9, 287-422), or may be prepared from known compounds by known methods.

A compound of formula (2AT), wherein X is methyl, can be prepared from known compounds by known methods.

A compound of formula (2P), wherein R' is $C_1$-$C_4$alkyl, can also be prepared from a compound of formula (2AF), by rearrangement under conditions similar to those described for the conversion of a compound of formula (2AA) to a compound of formula (2A). A compound of formula (2AW) is known, or can be prepared by known methods using known reagents.

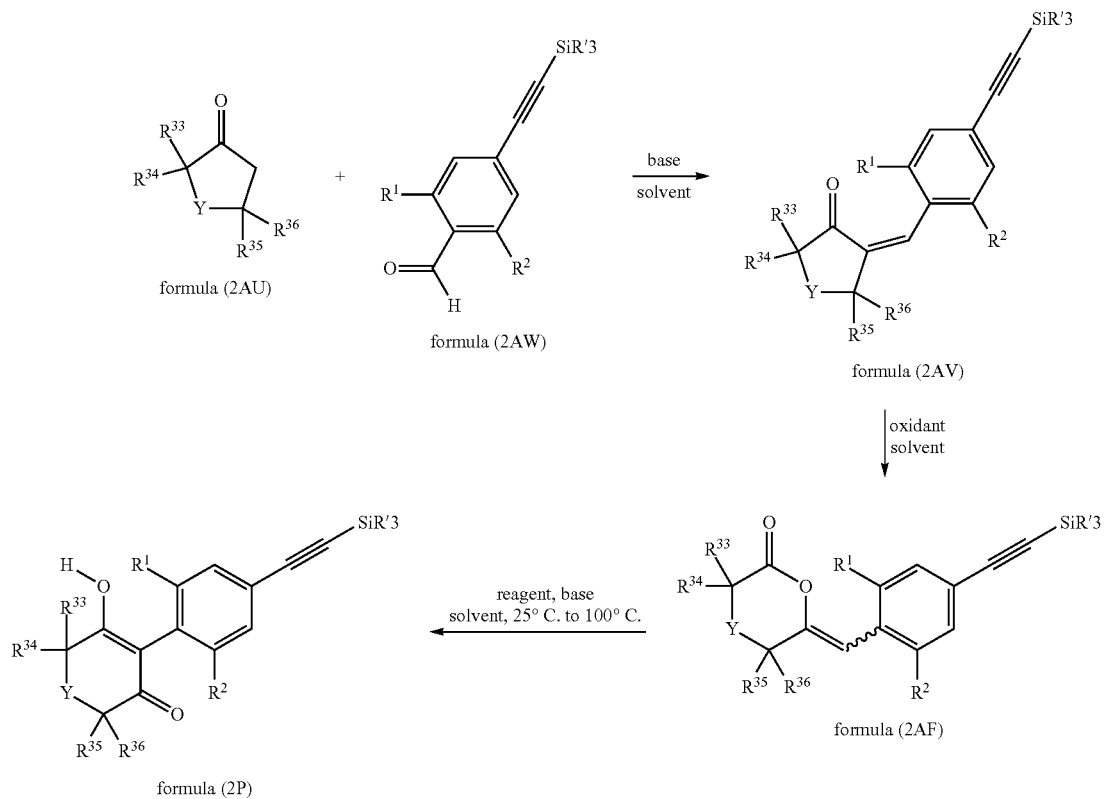

Similarly, a compound of formula (2L) can also be prepared from a compound of formula (2AJ) by rearrangement under similar conditions. Compounds of formula (2AY) are known compounds, or can be prepared from known reagents using known methods.

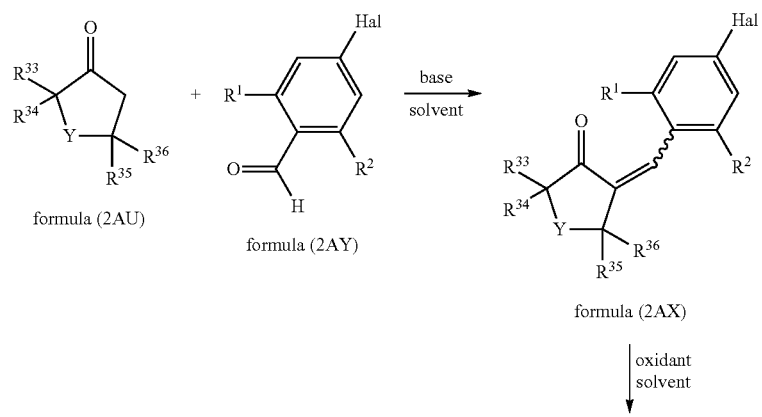

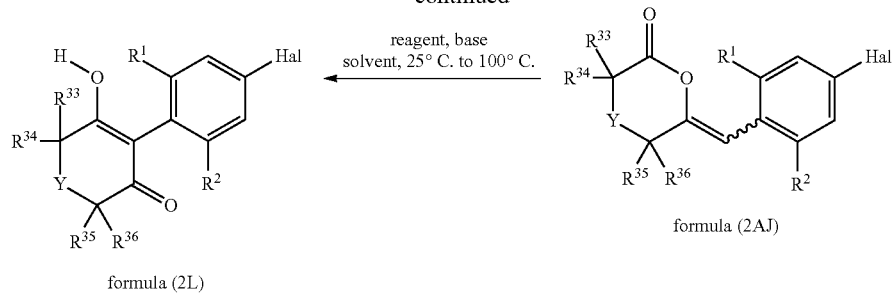
Similarly, a compound of formula (2W) can also be prepared from a compound of formula (2AO) by rearrangement under similar conditions. Compounds of formula (2AAA) are known compounds, or can be prepared from known reagents using known methods.
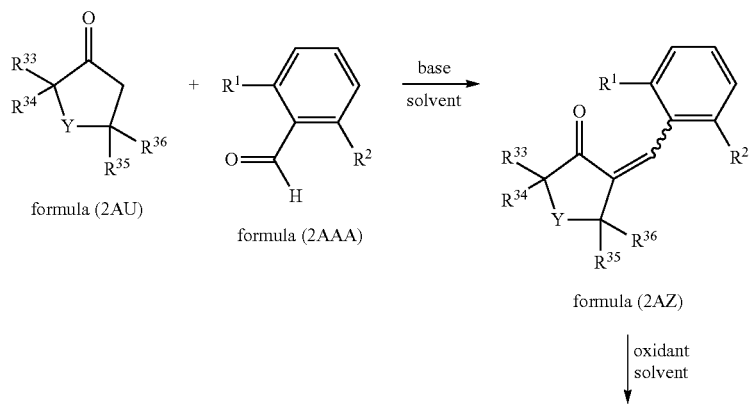
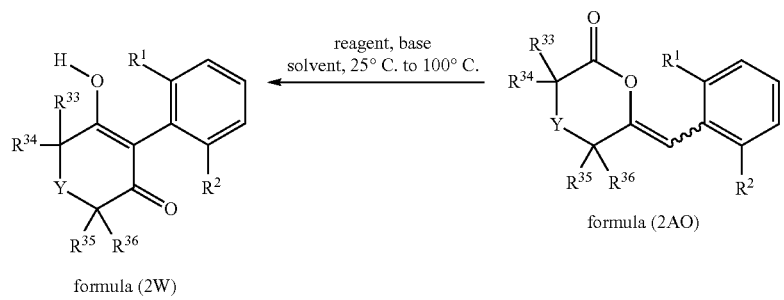

In a further approach, a compound of formula (2A), wherein X is methyl, can be prepared by a rearrangement of an epoxide of formula (2AAB) catalysed by the presence of an acid, in the presence of a suitable solvent (e.g. organic solvent).

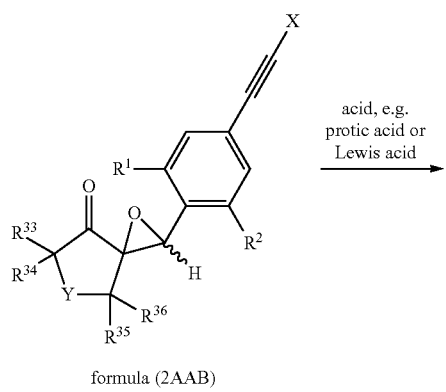

formula (2AAB)

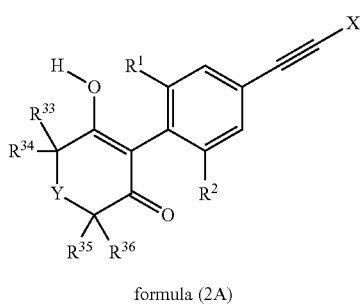

formula (2A)

For the rearrangement of (2AAB) to (2A), suitable acids include a Brönsted acid (protic acid), such as a mineral acid or an organic acid, for example sulfuric acid, hydrochloric acid, hydrogen chloride, p-toluenesulfonic acid, methanesulfonic acid, acetic acid or formic acid, or a Lewis acid, such as a metal halide, for example boron trifluoride, aluminium chloride, iron chloride, tin(IV) chloride, zinc chloride, zinc bromide, or lithium perchlorate, or a metal triflate such as scandium triflate or ytterbium triflate. Mixtures of such acids can also be used. The conversion of a compound of formula (2AAB) into a compound of formula (2A) may be considered to be an example of a semi-Pinacol rearrangement (see for example WO 2010/136431 A1 (Syngenta Limited); M. Paulson, M. Daliya and C. Asokan, Synth. Commun. (2007), 37(5), 661-665; S. Sankararaman and J. Nesakumar, J. Chem. Soc, Perkin Trans. 1, (1999), (21), 3173-3175; K. Rehse and R. Bienfait, Archiv der Pharmazie, (1984), 317(5), 385-93; H. Kamath, A. Sahasrabudhe, B. Bapat and S. Kulkarni, Indian J. Chem., Section B: (1981), 20B(12), 1094-6; G. Buchanan and D. Jhaveri, J. Org. Chem. (1961), 26 4295-9; and H. House, Richard L. Wasson, J. Am. Chem. Soc., (1956), 78, 4394-400). For the rearrangement of (2AAB) to (2A), a suitable solvent (e.g. organic solvent) is preferably chosen to be compatible with the acid used, and can include a chlorinated hydrocarbon, an alcohol, an ether, an aromatic solvent or an organic acid, for example dichloromethane, dichloroethane, diethyl ether, acetic acid, formic acid, toluene, benzene, methanol, ethanol, isopropanol or tetrahydrofuran. Preferably the reaction, i.e. the rearrangement of (2AAB) to (2A), is performed using methanesulfonic acid in toluene at a temperature between 25° C. and 150° C.

A compound of formula (2AAB) can be prepared by the epoxidation of a compound of formula (2AS). Epoxidation may be effected by treatment of a compound of formula (2AS) with a suitable oxidising agent such as an organic peroxide or metal hyperchlorite, for example dimethyldioxirane, sodium hypochlorite, hydrogen peroxide, tert-butyl peroxide or trifluoroperacetic acid, optionally in combination with a suitable base, such as an alkali metal hydroxide or carbonate, alkaline earth metal hydroxide or carbonate, or an amine base such as 1,8-diazabicyclo[5.4.0]-undec-7-ene, optionally in a suitable solvent, such as an alcohol or halogenated hydrocarbon, for example methanol, ethanol or dichloromethane, and at a suitable temperature. The reaction can also be performed under biphasic conditions, in which a phase-transfer reagent is also typically used in 0.001-50 mole %. The phase transfer reagent is preferably a quaternary ammonium salt, a crown ether, a polyethylene glycol, or phosphonium salt. Similar reactions are known in the literature (see for example WO 2010/136431 A1 (Syngenta Limited); I. K. Korobitsyna, 0. P. Studzinskii, The Russian Journal of Organic Chemistry (1969), 5(8), 1493-5; A. Halasz, Z. Jambor, A. Levai, C. Nemes, T. Patonay and G. Toth, J. Chem. Soc, Perkin Trans. 1, (1996), (4), 395-400; N. Yousif, F. Gad, A. Fahmy, M. Amine and H. Sayed, Phosphorus, Sulfur and Silicon and the Related Elements (1996), 117, 11-19; T. Ooi, D. Ohara, M. Tamura and K. Maruoka, J. Am. Chem. Soc., (2004), 126(22), 6844-6845; A. Amr, H. Hayam and M. Abdulla, Archiv der Pharmazie, (2005), 338(9), 433-440; K. Drauz, S. M. Roberts, T. Geller and A. Dhanda, U.S. Pat. No. 6,538,105 B1; and L. S. Chagonda and B. A. Marples, J. Chem. Soc. Perkin 1, 1988, 875-879). Preferably, epoxidation is carried out using hydrogen peroxide and a metal hydroxide (especially lithium hydroxide or sodium hydroxide), in methanol at a temperature of between −10° C. and 60° C.

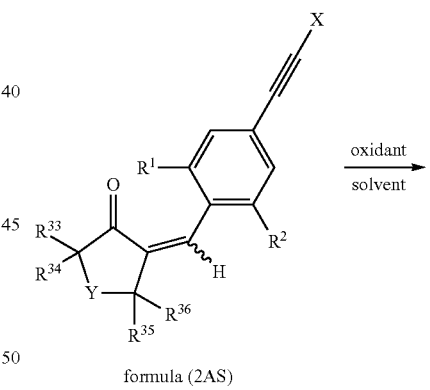

formula (2AS)

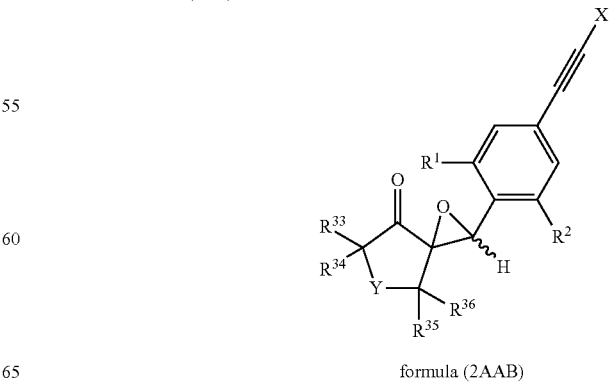

formula (2AAB)

Alternatively a compound of formula (2AAB), wherein X is methyl, may be prepared by reacting a compound of formula (2AAC) (wherein halogen is chlorine, bromine or iodine, preferably chlorine or bromine) with a compound of formula (2AT), in the presence of a suitable base, optionally in a suitable solvent, at a suitable temperature.

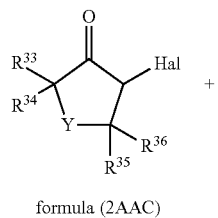

formula (2AAC)

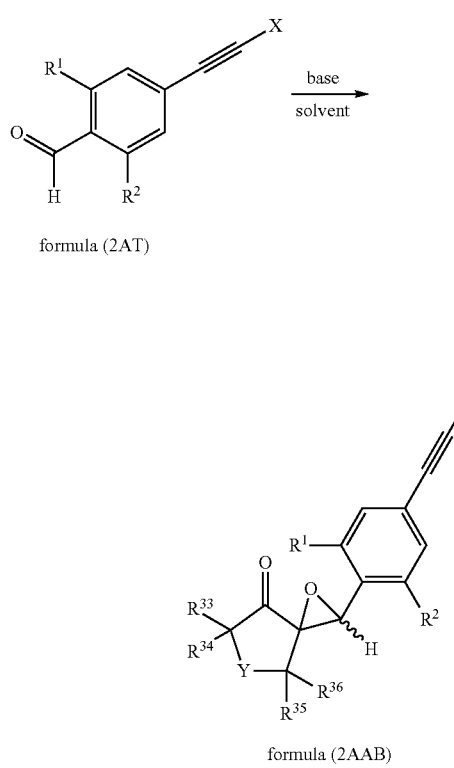

Suitable bases include alkali or alkali earth metal hydroxides, such as sodium hydroxide, lithium hydroxide or potassium hydroxide, alkali or alkali earth metal alkoxides, such as sodium methoxide, sodium ethoxide, potassium tert-butoxide or sodium tert-butoxide, alkali or alkali earth metal carbonates such as potassium carbonate or sodium carbonate, or sodium bicarbonate, metal amides such as lithium diisopropylamide, lithium hexamethyldisilazide or lithium 2,2,6,6-tetramethylpiperidide, organometallics such as butyl lithium or ethylmagnesium bromide, or metal hydrides such as sodium hydride or potassium hydride. Suitable solvents include chlorinated hydrocarbons, ethers, alcohols, aromatics and various polar aprotic solvents, for example 1,2-dimethoxyethane, tetrahydrofuran, 1,4-dioxane, diethyl ether, dibutyl ether, dichloromethane, dichloroethane, acetonitrile, dimethyl sulfoxide, N,N-dimethylformamide, benzene, toluene, methanol, ethanol, isopropanol or tert-butanol, and is chosen to be compatible with the base under the reaction conditions. The reaction can also be performed under biphasic conditions, in which a phase-transfer reagent is also typically used in 0.001-50 mole %. The phase transfer reagent is preferably a quaternary ammonium salt, a crown ether, a polyethylene glycol, or phosphonium salt. Most preferably the reaction is performed using lithium diisopropylamide in tetrahydrofuran at a temperature range of −100° C. to 60° C. The conversion of a compound of formula (2AAC) into a compound of formula (2AAB) may be considered to be an example of a Darzens condensation (see for example WO 2010/136431 A1 (Syngenta Limited); W. N. Wassef, M. M. El-Barky, Journal of Chemical Research, Synopses (1990), (12), 402-3; J. Li, X. Liu, X. Li, Youji Huaxue (2007), 27(11), 1428-1431; Y. Tong, Y. Cheng, X. Guo, S. Wu, Hecheng Huaxue (2007), 15(1), 102-104; C. Parmenon, J. Guillard, D. Caignard, N. Hennuyer, B. Staels, V. Audinot-Bouchez, J. Boutin, C. Dacquet, A. Ktorza, M. Viaud-Massuard, Bioorganic & Medicinal Chemistry Letters (2008), 18(5), 1617-1622; H. Xiao, X. Han, J. Xiong, Faming Zhuanli Shenqing Gongkai Shuomingshu (2007), p11; J. M. Concellon, E. Bardales, R. Llavona, Journal of Organic Chemistry (2003), 68(4), 1585-1588).

Compounds of formula (2AAC), wherein Y is O or $CR^{38}R^{39}$ are either known compounds (see for example WO 2010136431; B. Sreedhar, P. S. Reddy, M. Madhavi, Synthetic Communications (2007), 37(23), 4149-4156; R. R. Agarwal, S. S. Deshapande, Journal of the Indian Chemical Society (1949), 26, 483-6; H. Richet, R. Dulou, R., G. Dupont, Bulletin de la Societe Chimique de France (1947), 693-9; H. Richet, Ann. Chim. [12] (1948), 3 317-54; I. K. Korobitsyna, Yu. K. Yur'ev, Yu. A. Cheburkov, E. M. Lukina, Russian Journal of General Chemistry (1955), 25, 734-8; I. K. Korobitsyna, Yu. K. Yur'ev, Yu. A. Cheburkov, E. M. Lukina, Russian Journal of General Chemistry (1955), 25, 690-702; F. Leonard, A. Wajngurt, H. Horn, Journal of Organic Chemistry (1956), 21, 1400-4; I. K. Korobitsyna, I. G. Zhukova, V. A. Kuvshinova, N. N. Gaidamovich, Yu. K. Yur'ev, Doklady Akademii Nauk SSSR (1957), 114, 327-30; I. K. Korobitsyna, I. G. Zhukova, I. G, Yu. K. Yur'ev, Russian Journal of General Chemistry (1959), 29, 2190-6; I. K. Korobitsyna, L. L. Rodina, L. M. Stashkova, Chemistry of Heterocyclic Compounds (1966), (6), 843-7; G. Hoehne, F. Marschner, K. Praefcke, P. Weyerstahl, Chem. Ber. (1975), 108(2), 673-82; H. Saimoto, T. Hiyama, H. Nozaki, Bull. Chem. Soc. Jpn., (1983), 56(10), 3078-87; A. M. Zvonok, N. M. Kuz'menok, I. G. Tishchenko, L. S. Stanishevskii, Russian Journal of General Chemistry (1985), 21(6), 1330-4) or can be prepared from compounds of formula (2AU) under known conditions.

Compounds of formula (2AAC), wherein Y is S, S(O) and $S(O)_2$, are either known compounds (see for example M. Polievka, L. Uhlar, V. Patek, Petrochemia (1973), 13(5-6), 156-60; N. N. Novitskaya, B. V. Flekhter, G. M. Prokhorov, A. S. Lukmanova, G. A. Tolstikov, G. V. Leplyanin, S. A. Lange, M. V. Strashnov, SU 468920 A1; P. H. McCabe, W. Routledge, Tetrahedron Letters (1976), (1), 85-6; T. S. Chou, C. Y. Tsai, Tetrahedron Letters (1992), 33(29), 4201-4), or can be prepared from compounds of formula (2AU) under known conditions. Compounds of formula (2AAC), wherein Y is C(O), can be prepared from compounds of formula (2AU) under similar halogenation conditions.

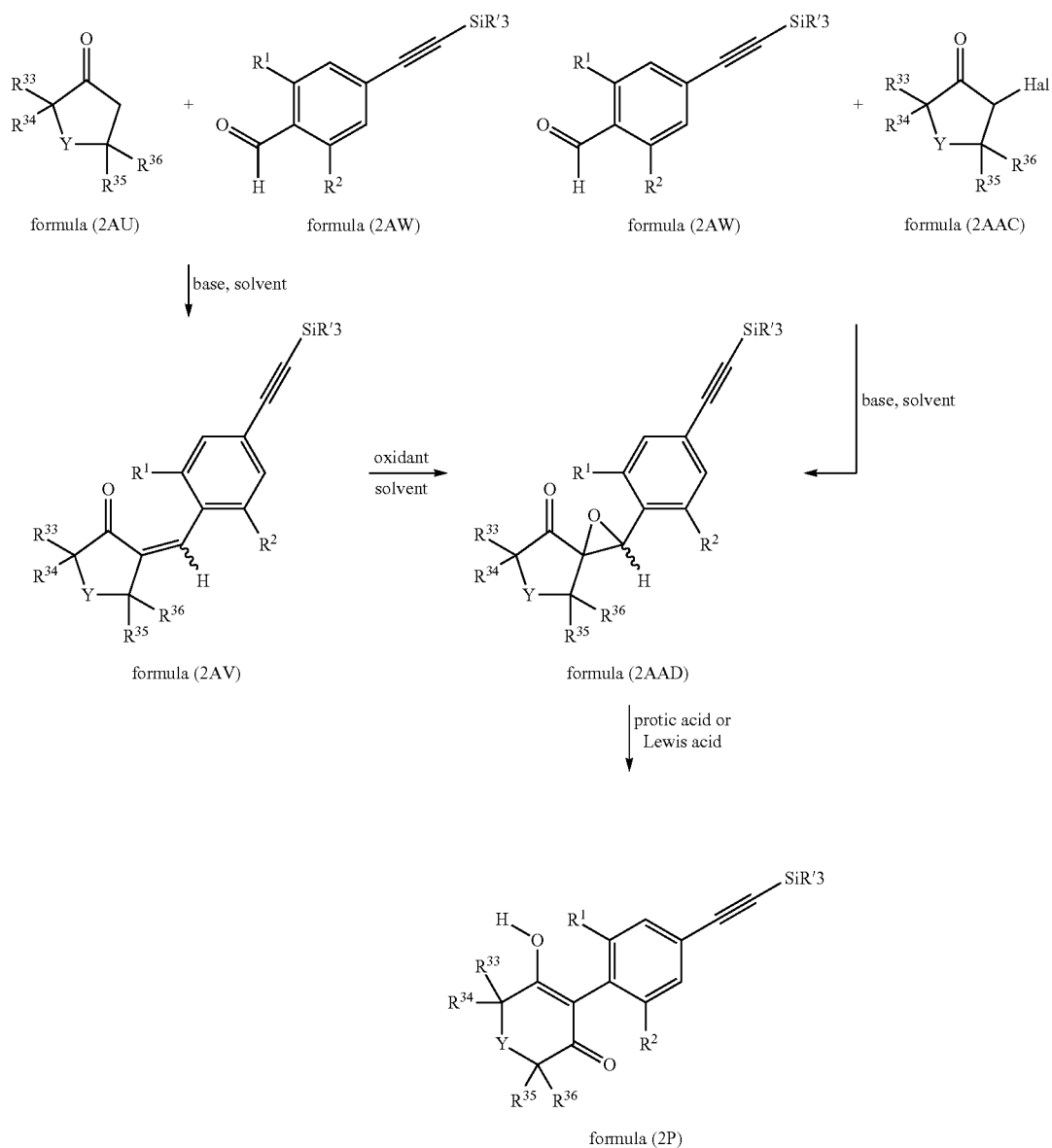

Compounds of formula (2P), wherein R' is $C_1$-$C_4$alkyl, can also be prepared from compounds of formula (2AAD), using similar procedures and conditions described previously. Compounds of formula (2AAD) can either be prepared from compounds of formula (2AU) and (2AW), via compounds of formula (2AV), or from compounds of formula (2AAC) and (2AW).

Similarly, a compound of formula (2L) can also be prepared from a compound of formula (2AAE). A compound of formula (2AY) is known in the literature or can be prepared from known reagents using known methods.

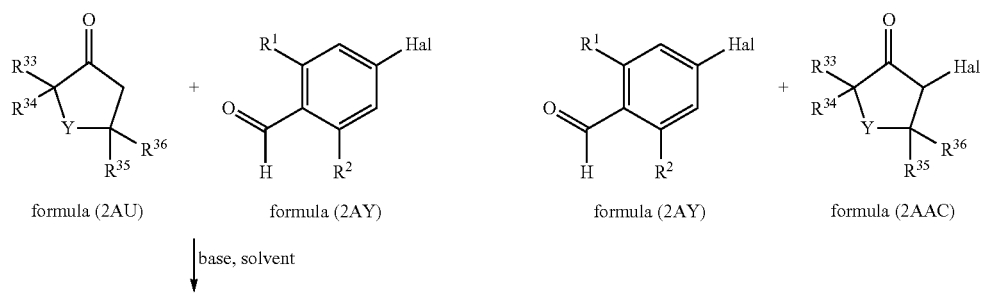

-continued
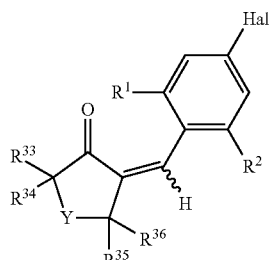
formula (2AX)
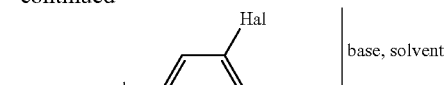
formula (2AAE)
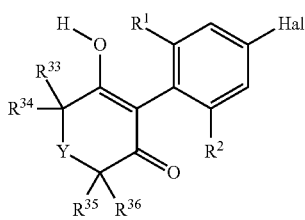
formula (2L)
Similarly, a compound of formula (2W) can also be prepared from a compound of formula (2AAF), which can be prepared using similar chemistry to that described previously.
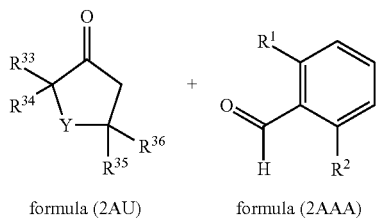
formula (2AU)    formula (2AAA)
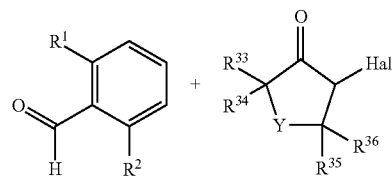
formula (2AAA)    formula (2AAC)
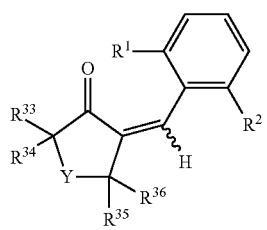
formula (2AZ)
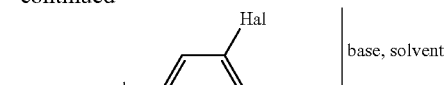
formula (2AAF)

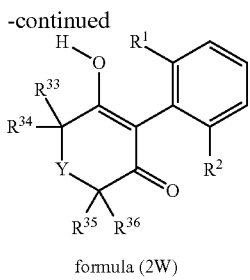

formula (2W)

In a further approach, a compound of formula (2A), wherein X is methyl, may be prepared by reacting a compound of formula (2AAH) with a with an aryllead tricarboxylate, in the presence of a suitable ligand and in a suitable solvent. Similar reactions are described in the literature (see for example M. Muehlebach et al., WO08/071405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (2AAG). Preferably the ligand is a nitrogen containing heterocycle such as N,N-dimethylaminopyridine, 1,10-phenanthroline pyridine, bipyridine, or imidazole, and one to ten equivalents (i.e. mole equivalents) of ligand with respect to a compound of formula (2AAG) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.

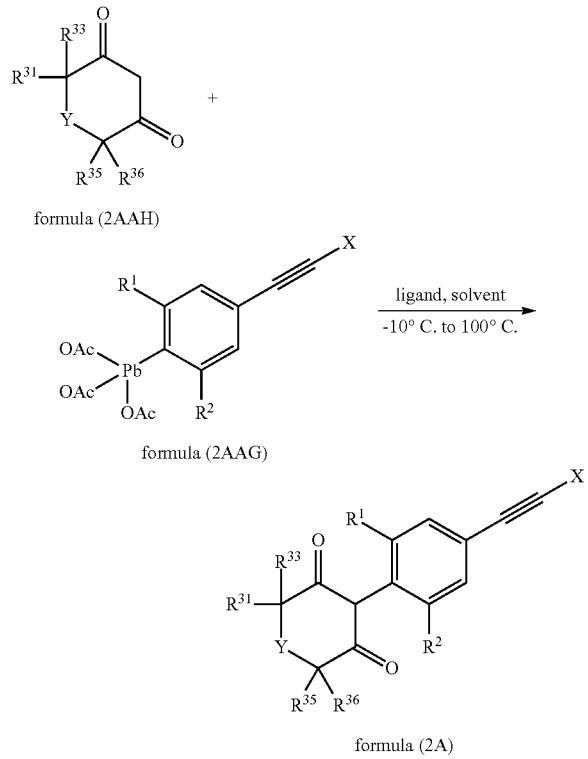

formula (2AAH)

formula (2AAG)

formula (2A)

Compounds of formula (2AAH), wherein Y is O, are known compounds or may be prepared by routes analogous to those described in the literature (see, for example, M. Muehlebach et al., WO08/071405; M. Morgan and E. Heyningen, J. Am. Chem Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089,046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem, (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854).

Compounds of formula (2AAH), wherein Y is S, are known compounds or may be prepared by routes analogous to those described in the literature (see, for example, E. Fehnel and A. Paul, J. Am. Chem Soc., (1955), 77, 4241-4244; E. Er and P. Margaretha, Helvetica Chimica Acta (1992), 75(7), 2265-69; H. Gayer et al., DE 3318648 A1).

Compounds of formula (2AAH), wherein Y is C(O), are known compounds or may be prepared by routes analogous to those described in the literature (see, for example, R. Götz and N. Götz, WO2001/060776 R. Götz et al. WO 2000/075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et al., Chem. Ber., (1986), 119, 3394-3404 and references therein).

Compounds of formula (2AAH), wherein Y is $CR^{38}R^{39}$ are known compounds of may be prepared by routes analogous to those described in the literature (see for example, M. Muehlebach et al., WO08/110307; M. Muehlebach et al., WO08/110308; S. Spessard and B. Stoltz, Organic Letters, (2002), Vol. 4, No. 11, 1943-1946; F. Effenberger et al., Chem. Ber., (1984), 117, 3280-3296; W. Childers et al., Tetrahedron Lett., (2006), 2217-2218; W. Childers et al., US2006/0004108; H. Schneider and C. Luethy, EP1352890; D. Jackson, A. Edmunds, M. Bowden and B. Brockbank, WO2005/105745 and WO2005/105717; R. Beaudegnies, C. Luethy, A. Edmunds, J. Schaetzer and S. Wendeborn, WO2005/123667; J-C. Beloeil, J-Y. Lallemand, T. Prange, Tetrahedron, (1986), Vol. 42. No. 13, 3491-3502; G. Stork and R. Danheiser, J. Org. Chem., (1973), 38 (9), 1775-1776; H. Favre et al., Can. J. Chem. (1956), 34 1329-39; R. Shriner and H. Todd, Org. Synth. Coll. Vol. II, (1943), 200-202).

A compound of formula (2AAI), wherein X is methyl, may be prepared from a compound of formula (2AAJ) by treatment with lead tetraacetate in a suitable solvent (for example chloroform) at 25° C. to 100° C. (preferably 25-50°

C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

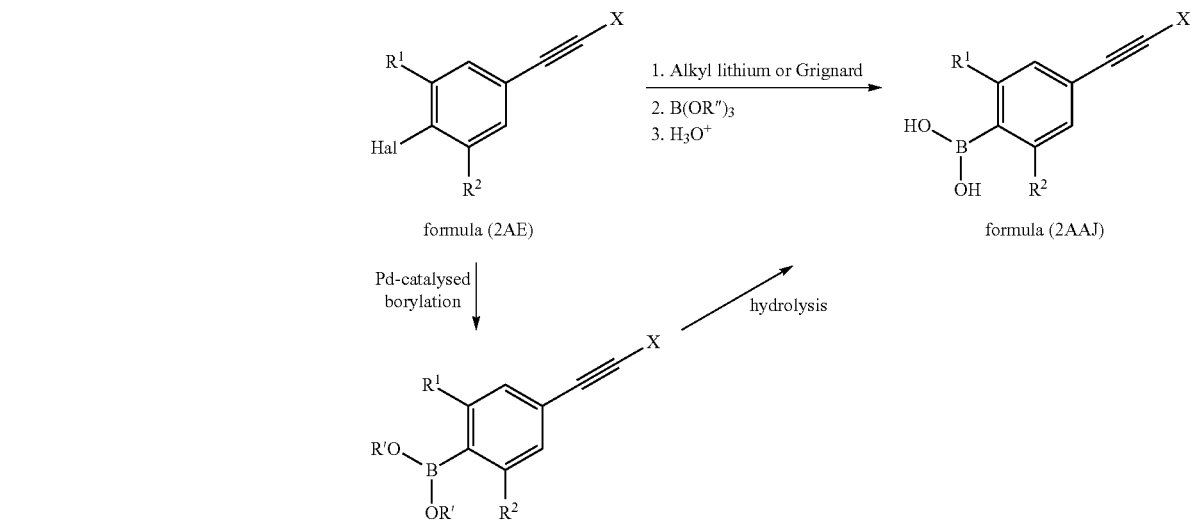

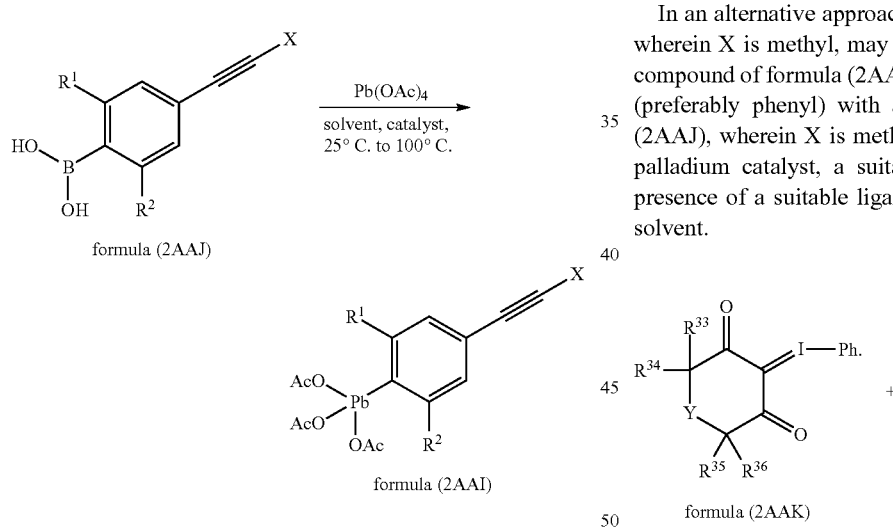

An aryl boronic acid of formula (2AAJ), wherein X is methyl, may be prepared from an aryl halide of formula (2AE), wherein Hal is bromine or iodine by known methods (see, for example, W. Thompson and J. Gaudino, J. Org. Chem, (1984), 49, 5237-5243 and R. Hawkins et al., J. Am. Chem. Soc., (1960), 82, 3053-3059). Thus an aryl halide of formula (2AE) may be treated with an alkyl lithium or alkyl magnesium halide at low temperature, and the aryl magnesium or aryl lithium reagent obtained is allowed to react with a trialkyl borate, $B(OR'')_3$, preferably trimethylborate, to give an aryl dialkylboronate which may be hydrolysed to the desired boronic acid of formula (2AAJ), where X is methyl, under acidic conditions. Alternatively the same overall transformation of compound (2AE) to compound (2AAJ), wherein X is methyl, may be achieved through a palladium-catalysed borylation reaction under known conditions using In an alternative approach, a compound of formula (2A), wherein X is methyl, may be prepared by the reaction of a compound of formula (2AAK), wherein Ar is an aryl moiety (preferably phenyl) with an arylboronic acid of formula (2AAJ), wherein X is methyl, in the presence of a suitable palladium catalyst, a suitable base, an optionally in the presence of a suitable ligand or additive, and in a suitable solvent.

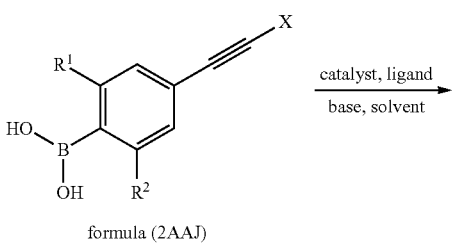

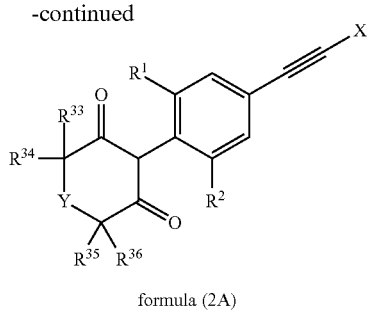

formula (2A)

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclohexylphosphino-2',6'-dimethoxybiphenyl, 2-dicyclohexylphosphino-2',4',6'-triisopropylbiphenyl, 1,1'-bis(diphenylphosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of formula (2AAK) may be prepared from a compound of formula (2AAH) by treatment with a hypervalent iodine reagent such as a (diacetoxy)iodobenzene or iodosylbenzene, and a base such as aqueous sodium carbonate, lithium hydroxide or sodium hydroxide, in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

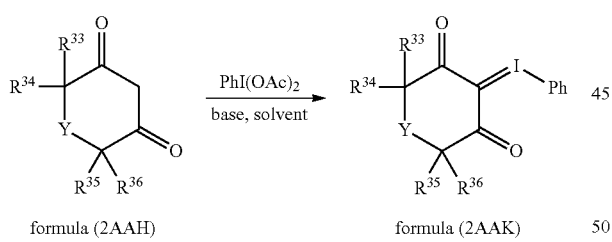

formula (2AAH)     formula (2AAK)

In a further approach, a compound of formula I, wherein Q is Q2 and X is methyl, may be prepared by reacting a compound of formula (2AAL) (wherein G is preferably $C_{1-4}$ alkyl, and Hal is a halogen, preferably bromine or iodine), with an arylboronic acid of formula (2AAJ) in the presence of a suitable palladium catalyst, for example 0.001-50 mole % palladium(II) acetate with respect to compound (2AAL), and a base, for example 1 to 10 equivalents (i.e. mole equivalents) of potassium phosphate with respect to compound (2AAL), and preferably in the presence of a suitable ligand for example 0.001-50 mole % (2-dicyclohexylphosphino)-2',6'-dimethoxybiphenyl with respect to compound (2AAL), and in a suitable solvent, for example toluene, preferably between 25° C. and 200° C. Similar couplings are known in the literature (see for example, Y. Song, B. Kim and J.-N. Heo, Tetrahedron Letters (2005), 46 (36), 5987-5990). A compound of formula I, wherein Q is Q2 and X is preferably methyl, can be converted to a compound of formula (2A) by hydrolysis of the enol ether under known conditions.

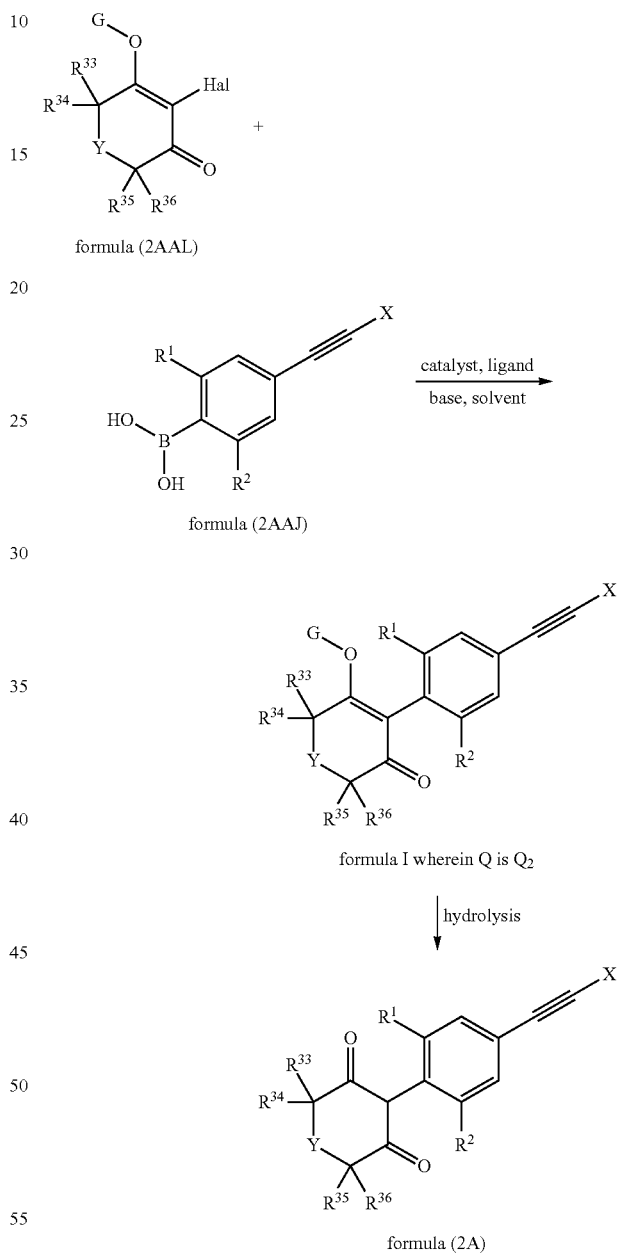

A compound of formula (2AAL) may be prepared by halogenating a compound of formula (2AAH), followed by reaction of the resulting halide of formula (2AAN) with a $C_1$-$C_4$alkyl halide or tri-$C_1$-$C_4$alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690).

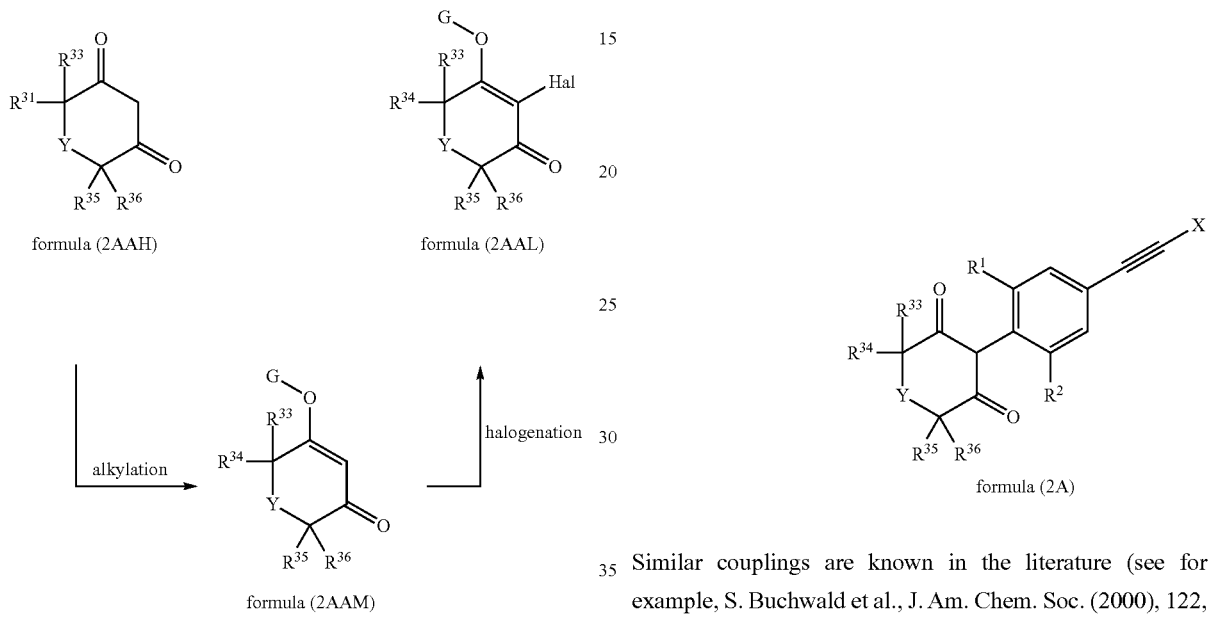

formula (2AAN)

formula (2AAH)  formula (2AAL)

formula (2AAM)

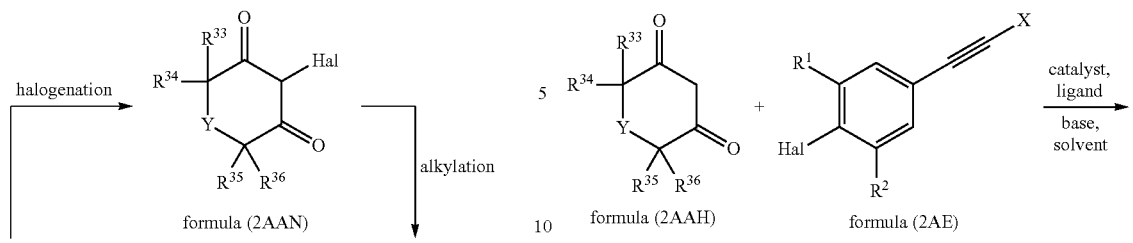

formula (2AAH)  formula (2AE)

formula (2A)

Alternatively, a compound of formula (2AAL) may be prepared by reacting a compound of formula (2AAH) with a $C_1$-$C_4$alkyl halide or a tri-$C_1$-$C_4$alkylorthoformate, and halogenating the resulting enol ether of formula (2AAM) under known conditions (see for example Y. Song, B. Kim and J.-N. Heo, Tetrahedron Letters (2005), 46(36), 5987-5990).

In a further approach, a compound of formula (2A), wherein X is methyl, may be prepared by reacting a compound of formula (2AAH) with a compound of formula (2AE) in the presence of a suitable palladium catalyst, for example 0.001-50 mole % palladium(II) acetate with respect to compound (2AAH), and a base, for example 1 to 10 equivalents (i.e. mole equivalents) of potassium phosphate with respect to compound (2AAH), and preferably in the presence of a suitable ligand for example 0.001-50 mole % (2-dicyclohexylphosphino)-2',4',6'-triisopropylbiphenyl with respect to compound (2AAH), and in a suitable solvent, for example dioxane, preferably between 25° C. and 200° C. and optionally under microwave heating.

Similar couplings are known in the literature (see for example, S. Buchwald et al., J. Am. Chem. Soc. (2000), 122, 1360-1370; B. Hong et al. WO 2005/000233). Alternatively, a compound of formula (2A) may be prepared by reacting a compound of formula (2AAH) with a compound of formula (2AE) in the presence of a suitable copper catalyst, for example 0.001-50 mole % copper(I) iodide with respect to compound (2AAH), and a base, for example 1 to 10 equivalents (i.e. mole equivalents) of cesium carbonate with respect to compound (2AAH), and preferably in the presence of a suitable ligand, for example 0.001-50 mole % L-proline with respect to compound (2AAH), and in a suitable solvent, for example dimethylsulfoxide, preferably between 25° C. and 200° C. Similar couplings are known in the literature (see for example, Y. Jiang et al., Synlett, (2005), 18, 2731-2734, and X. Xie et al., Organic Letters (2005), 7(21), 4693-4695).

A compound of formula (2P), wherein R" is $C_1$-$C_4$alkyl, can also be prepared using using similar methods described previously, starting from silylated precursors (2AAO), (2AAP) and (2AAI). Compounds (2AAO), (2AAP) and (2AAI) are known compounds, or can be prepared using similar methods to those described previously.

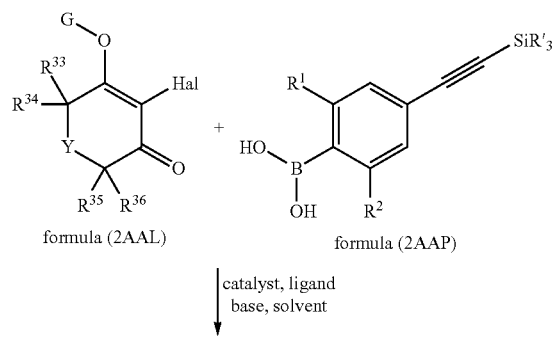
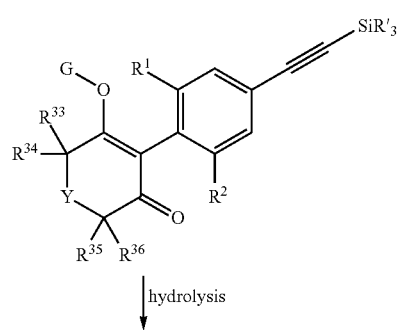
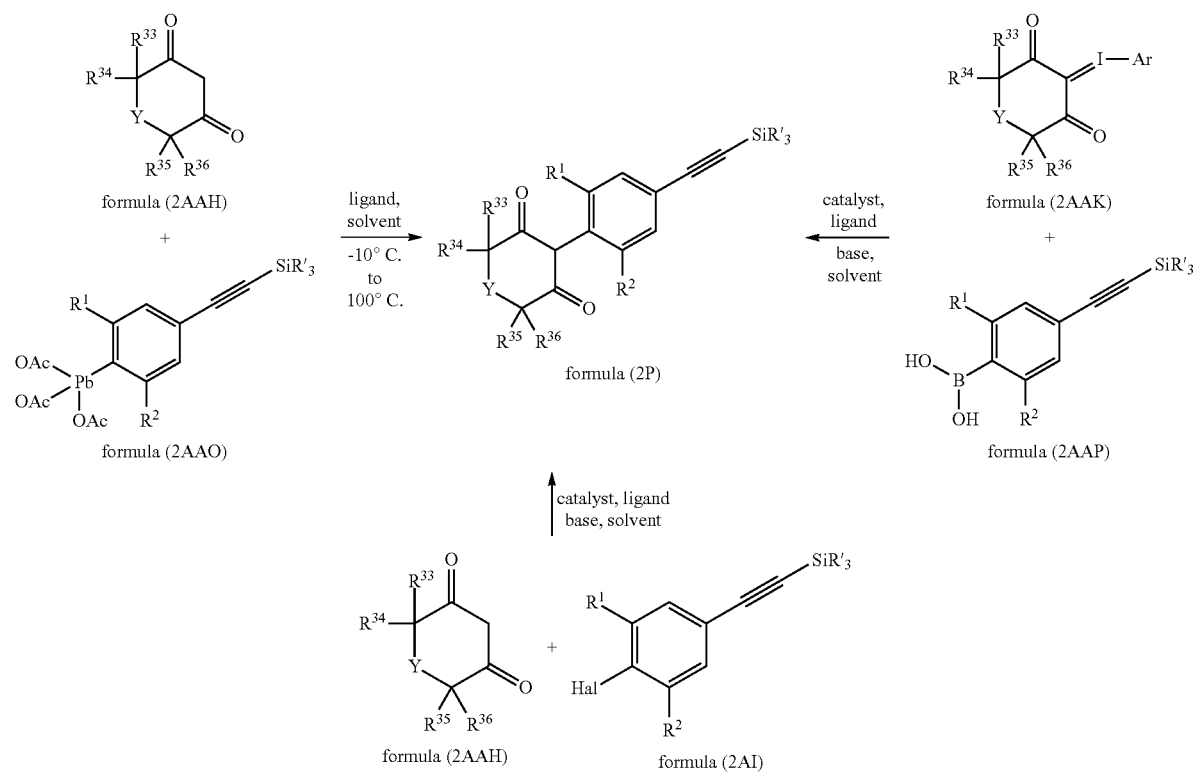

Similiarly, a compound of formula (2L) can also be prepared from suitable halogenated precursors, using similar methods to those described previously.
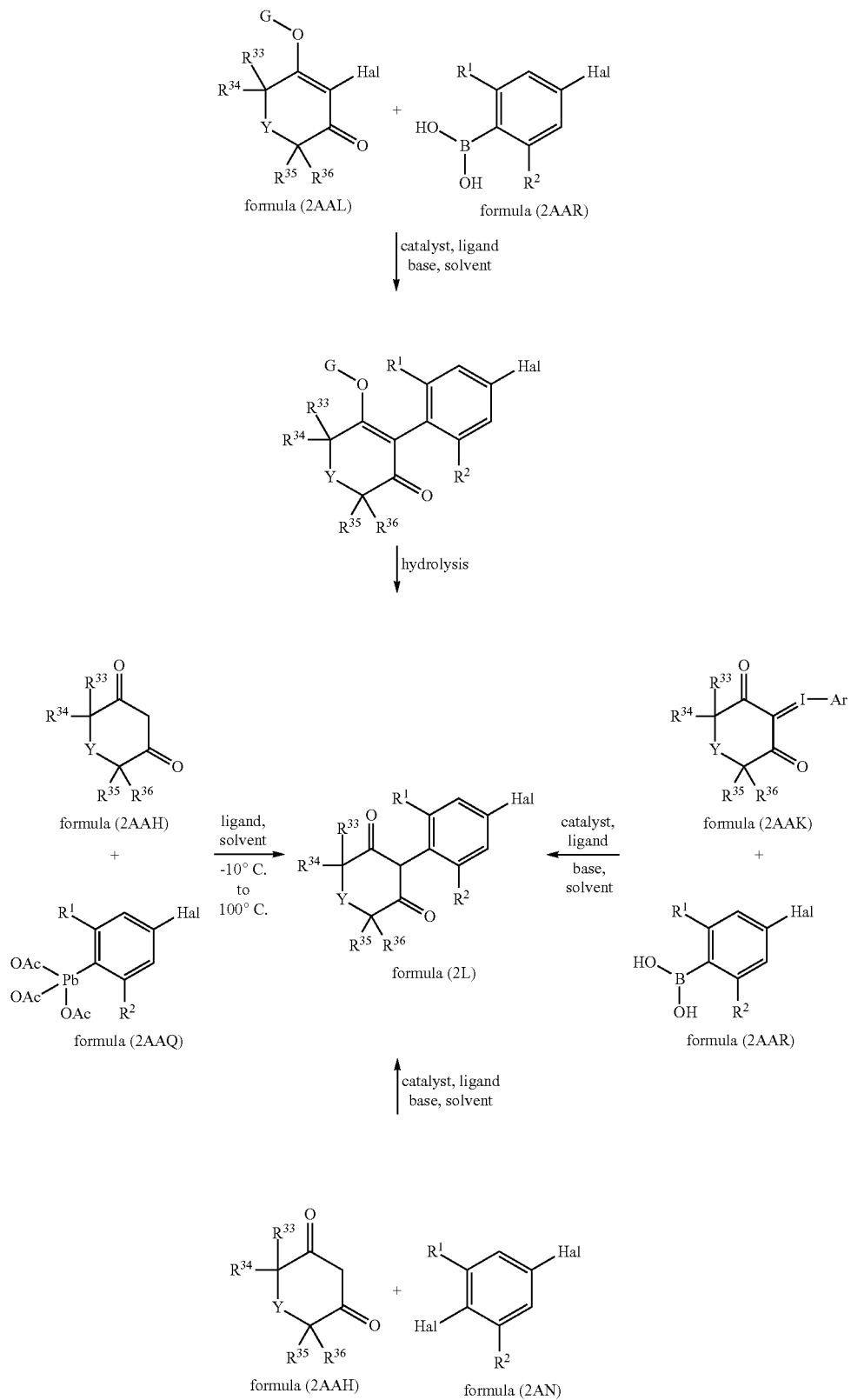

Similarly, a compound of formula (2W) can also be prepared from suitable precursors, using similar methods to those described previously.

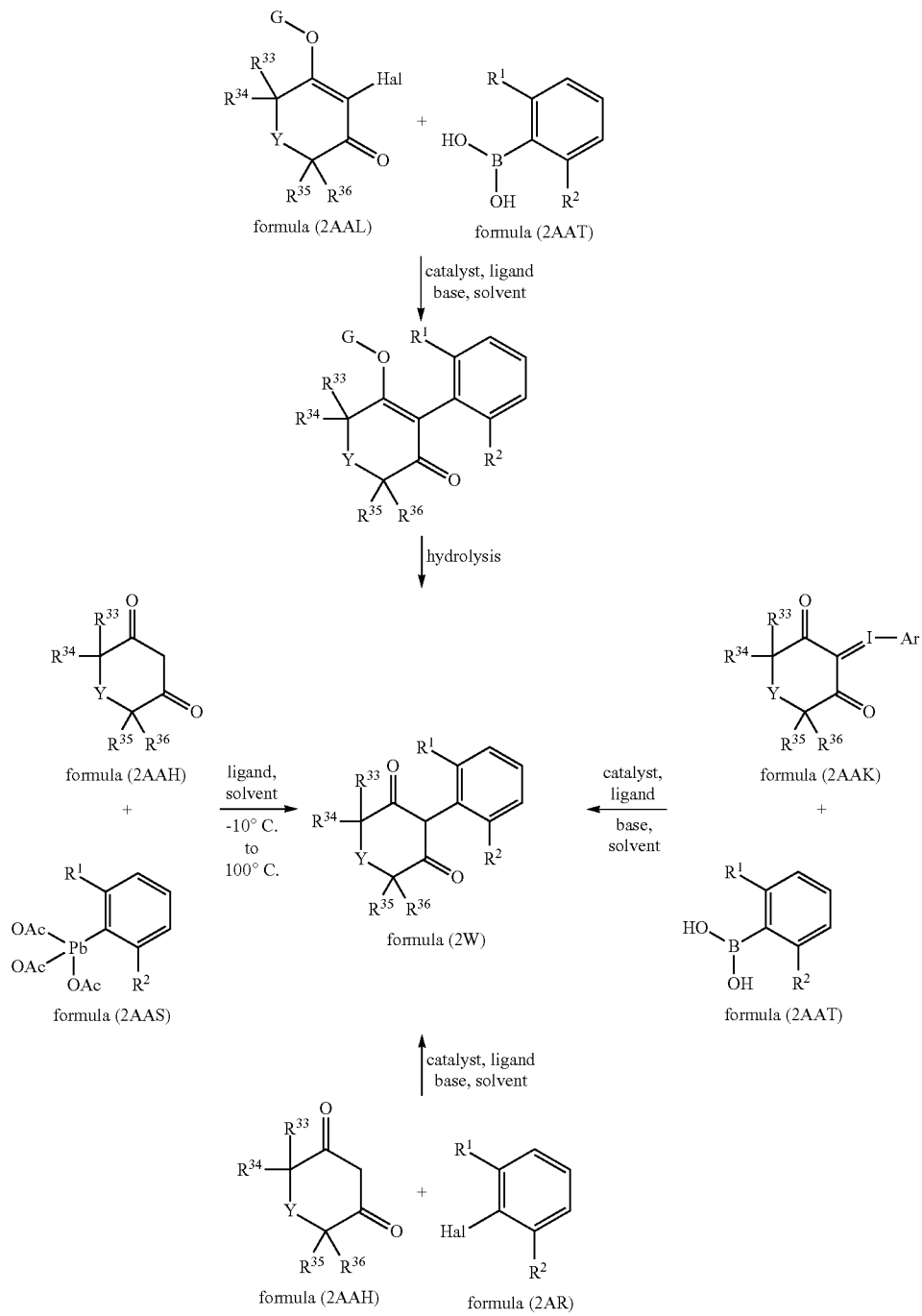

Furthermore, a compound of formula (2L) can be prepared by reacting a compound of formula (2AAH) with a halonitrobenzene of formula (2AAX) (under conditions similar to those described for coupling a compound of formula (2AAH) and a compound of formula (2AE) to produce a compound of formula (2A)), to produce a compound of formula (2AAW) which is then reduced under standard conditions (for a similar example see T. N. Wheeler, CA1113959). The aniline (2AAV) is then converted to the aryl halide (2L) under Sandmeyer conditions (for a similar example see T. N. Wheeler, CA1113959). Alternatively, a compound of formula (2AAU), wherein X is chlorine, can be prepared by reacting the aniline of formula (2AAV) with 1,1-dichloroethylene, a suitable metal salt such as copper(II) chloride, a suitable metal or alkyl nitrite in a suitable solvent at a suitable temperature. Such a reaction is an example of a Meerwein arylation, and examples are known in the literature (see for example T. Himmler, US 20100234651 and J-P. A. M. Bongartz, J. T. M. Linders, L. Meerpoel, G. S. E. Van Lommen, E. Coesemans, M. Braeken, C. F. R. N. Buyck, M. J. M. Berwaer, K. A. G. J.

M. De Waepenaert, P. W. M. Roevens, G. M. Boeckx, P. V. Davidenko, WO 2008148868).

A compound of formula (2A) can be prepared from a compound of formula (2AAU) under similar conditions to those described previously to convert a compound of formula (2J) to a compound of formula (2D).

(I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt thereof.

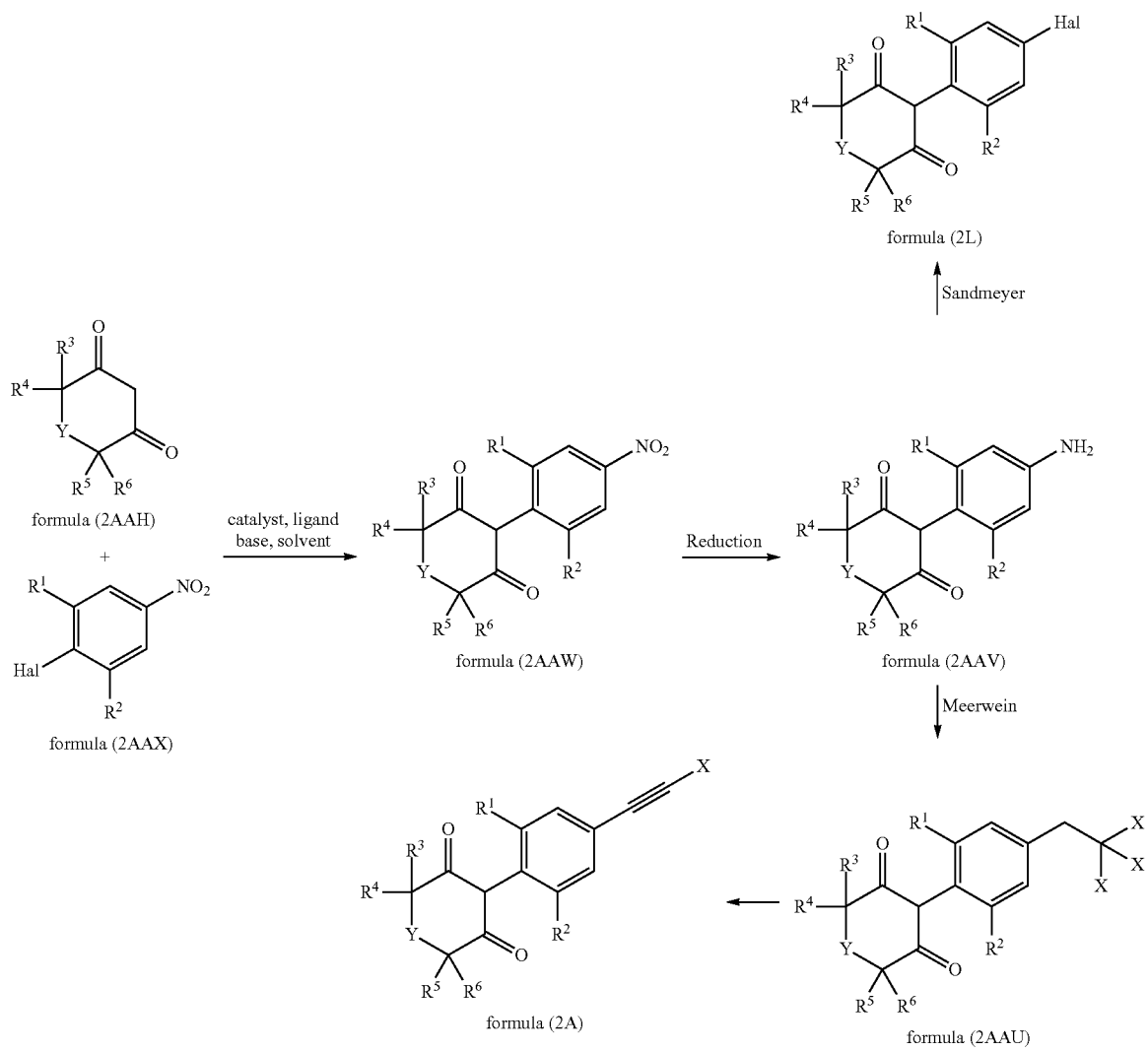

Herbicidal Compositions

In another aspect, the present invention provides a herbicidal composition, e.g. for use in a method of controlling weeds (e.g. monocotyledonous such as grassy weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

In a further aspect, the present invention provides a herbicidal composition, e.g. for use in a method of controlling weeds (e.g. monocotyledonous such as grassy weeds) in crops of useful plants, comprising a compound of formula The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g. known for instance under the trademark Exxsol®), a non-dearomatized hydrocarbon solvent with a boiling range between 100 and 320° C. (e.g. known under the tradename Varsol®), an isoparaffinic solvent with a boiling range between 100 and 320° C. (e.g. known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethylhexyl acetate, a $C_6$-$C_{18}$ alkyl ester of acetic acid (e.g. known under the tradename Exxate®), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate; an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2,4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropylenglycol with a molecular mass of 400-4000, or glycerol; glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-tris-alkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations (herbicidal compositions), especially in those formulations (herbicidal compositions) which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further formulation ingredients (e.g. inert ingredients) which can typically be used in formulations (herbicidal compositions) include crystallisation inhibitors, viscosity-modifying substances, suspending agents, dyes, anti-oxidants, foaming agents, light absorbers, mixing aids, anti-foams, complexing agents, neutralising or pH-modifying substances and/or buffers, corrosion-inhibitors, fragrances, wetting agents, absorption improvers, micronutrients, plasticisers, glidants, lubricants, dispersants, thickeners, antifreezes, microbiocides, compatibility agents and/or solubilisers; and/or also liquid and solid fertilisers.

The compositions (formulations) may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives/oil esters. The amount of oil additive (oil adjuvant) used in the composition according to the invention is generally from 0.01 to 10%, based on the spray mixture. For example, the oil additive (oil adjuvant) can be added to the spray tank in the desired concentration after the spray mixture has been prepared. Preferred oil additives (oil adjuvants) comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive (oil adjuvant) contains methylated rapeseed oil (rapeseed oil methyl ester). Another preferred oil additive (oil adjuvant) contains, for example, as active components essentially 80% by weight alkyl esters of fish oils and 15% by weight methylated rapeseed oil (rapeseed oil methyl ester), and also 5% by weight of customary emulsifiers and pH modifiers. Especially preferred oil additives (oil adjuvants) comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis). Those and other oil derivatives are also known from the Compendium of Herbicide Adjuvants, 5th Edition, Southern Illinois University, 2000.

The application and action of the above-mentioned oil additives (oil adjuvants) can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. As non-ionic surfactants, special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total oil additive (oil adjuvant) is generally from 1 to 50% by weight of the oil additive (oil adjuvant). Examples of oil additives (oil adjuvants) that consist of mixtures of oils and/or mineral oils and/or derivatives thereof with surfactants are TURBO-CHARGE®, ADIGOR® (both (Syngenta Crop Protection AG), ACTIPRON® (BP Oil UK Limited), AGRI-DEX® (Helena Chemical Company).

The above-mentioned surface-active substances may also be used in the formulations alone, that is to say without oil additives (oil adjuvants).

Furthermore, the addition of an organic solvent to the oil additive (oil adjuvant)/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further such oil additives (oil adjuvants) that are preferred according to the invention are SCORE® and ADIGOR® (both Syngenta Crop Protection AG).

In addition to the oil additives (oil adjuvants) listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

A particularly preferred oil adjuvant (oil additive), e.g. for use in the herbicidal compositions of the invention, is an emulsifiable concentrate which consists of:

(i) ethoxylated alcohols, which preferably includes ethoxylated $C_{12}$-$C_{22}$ fatty alcohols (preferably having a degree of ethoxylation of from 5 to 40); and
(ii) a mixture of heavy aromatic hydrocarbons, which preferably includes (or more preferably includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and
(iii) methylated rapeseed oil (rapeseed oil methyl ester) (e.g. Agnique ME 18 RD-F™), as an adjuvant; preferably present at about 47% w/w and/or about 45% w/v of the oil adjuvant/oil additive/emulsifiable concentrate. One example of such a emulsifiable concentrate oil adjuvant (oil additive) is ADIGOR™, currently available in many countries from Syngenta.

When the above emulsifiable concentrate oil adjuvant is used, it is preferably added to the herbicidal composition after dilution (e.g. with water and/or in a spray tank), typically before application to weeds and/or to crops of useful plants and/or to the locus thereof. In one particular embodiment, the herbicidal composition, e.g. after dilution (e.g. with water and/or in a spray tank), contains the above emulsifiable concentrate oil adjuvant, and additionally ammonium sulphate and/or isopropyl alcohol.

Such adjuvant oils as described in the preceding paragraphs may be employed as a or the carrier liquid in which an active compound is dissolved, emulsified or dispersed as appropriate to the physical form of the active compound.

In an alternative particular embodiment, the herbicidal composition of the invention comprises an agrochemically acceptable adjuvant comprising 1,2-cyclohexane dicarboxylic acid di-isononyl ester (e.g. CAS Registry no. 166412-78-8), e.g. as available from BASF as Hexamoll™ DINCH™. "Isononyl" in this context is thought to mean one or more, preferably a mixture of two or more, branched isomers of $C_9H_{19}$. In one particular embodiment, the herbicidal composition, e.g. after dilution (e.g. with water and/or in a spray tank), contains 1,2-cyclohexane dicarboxylic acid di-isononyl ester, and additionally ammonium sulphate and/or isopropyl alcohol.

In an alternative particular embodiment, the herbicidal composition of the invention comprises an agrochemically acceptable adjuvant comprising an organic phosphate and/or organic phosphonate adjuvant. Preferably, the phosphate adjuvant is a tris-[$C_4$-$C_{12}$alkyl or 2-($C_2$-$C_6$alkoxy)ethyl-] ester of phosphoric acid, or more preferably is tris-(2-ethylhexyl)phosphate, tris-n-octyl phosphate and/or tris-[2-(n-butoxy)ethyl]phosphate, or most preferably is tris-(2-ethylhexyl)phosphate. Preferably, the phosphonate adjuvant is a bis-($C_3$-$C_{12}$alkyl) ester of a $C_3$-$C_{12}$alkyl-phosphonic acid, or more preferably is bis-(2-ethylhexyl) (2-ethylhexyl) phosphonate, bis-(2-ethylhexyl) (n-octyl)phosphonate and/or di-n-butyl(n-butyl)phosphonate.

The formulations (herbicidal compositions) generally contain from 0.1 to 99% by weight, especially from 0.1 to 95% by weight, of a compound of formula I and from 1 to 99.9% by weight of a substantially-inert agrochemically acceptable substance, which preferably includes a formulation adjuvant and/or from 0 to 30% or from 0 to 25% (e.g. from 0.5 to 30% or from 0.5 to 25%) by weight of a surface-active substance. Whereas herbicidal compositions (especially commercial products) will preferably be formulated as concentrates, the end user will normally employ dilute formulations (compositions), e.g. formulations (compositions) diluted with water, in particular when applying the herbicidal composition to weeds and/or to crops of useful plants and/or to the locus thereof.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied (preferably post-emergence) at a rate of from 1 to 2000 g/ha, preferably from 1 to 1000 g/ha and most preferably at from 1 to 500 g/ha or from 5 to 500 g/ha.

Preferred formulations/compositions have especially the following representative compositions:
(%=percent by weight of the composition):

Emulsifiable Concentrates:
active ingredient: 0.3 to 95%, preferably 0.5 to 60% such as 1 to 40%
surface-active agents: 1 to 30%, preferably 3 to 20% such as 5 to 15%
solvents as liquid carrier: 1 to 80%, preferably 1 to 60% such as 1 to 40%

Dusts:
active ingredient: 0.1 to 10%, preferably 0.1 to 5%
solid carriers: 99.9 to 90%, preferably 99.9 to 99%

Suspension Concentrates:
active ingredient: 1 to 75%, preferably 3 to 50% or 10 to 50%
water: 98 to 24%, preferably 95 to 30% or 88 to 30%
surface-active agents: 1 to 40%, preferably 2 to 30%

Wettable Powders:
active ingredient: 0.5 to 90%, preferably 1 to 80%
surface-active agents: 0.5 to 20%, preferably 1 to 15%
solid carriers: 5 to 95%, preferably 15 to 90%

Granules:
active ingredient: 0.1 to 30%, preferably 0.1 to 15%
solid carriers: 99.5 to 70%, preferably 97 to 85%

Water Dispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | | | | |
|---|---|---|---|---|
| | a) | b) | c) | d) |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by dilution with water.

| F2. Solutions | | | | |
|---|---|---|---|---|
| | a) | b) | c) | d) |
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP (N-methyl-2-pyrrolidone) | — | — | 50% | 10% |
| aromatic hydrocarbon mixture $C_9$-$C_{12}$ | 35% | 30% | — | — |

The solutions are suitable for application undiluted or after dilution with water.

| F3. Wettable powders | | | | |
|---|---|---|---|---|
| | a) | b) | c) | d) |
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | | | |
|---|---|---|---|
| | a) | b) | c) |
| active ingredient | 0.1% | 5% | 15% |
| highly dispersed silica | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | | | |
|---|---|---|---|
| | a) | b) | c) |
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | | | | |
|---|---|---|---|---|
| | a) | b) | c) | d) |
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | | | | |
|---|---|---|---|---|
| | a) | b) | c) | d) |
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

| F8. Dusts | | | |
|---|---|---|---|
| | a) | b) | c) |
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F9. Suspension concentrates | | | | |
|---|---|---|---|---|
| | a) | b) | c) | d) |
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates, et al.

In a further aspect, the present invention provides a method of controlling weeds (preferably monocotyledonous weeds such as more preferably grassy monocotyledonous weeds) in crops of useful plants, which comprises applying a compound of the formula (I), or a herbicidal composition comprising such a compound, to the weeds and/or to the plants and/or to the locus thereof. (Preferably, in this further aspect, the herbicidal composition can be as described hereinabove or hereinbelow, e.g. as described in the "Herbicidal compositions", "Herbicidal uses", "Combinations and mixtures" and/or Claims sections hereinabove or hereinbelow.)

In a further aspect, the present invention provides a herbicidal composition, in particular for use in a method of controlling weeds (preferably monocotyledonous weeds such as more preferably grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular: cereals (e.g. non-oat cereals, in particular non-oat non-*sorghum* non-millet cereals, more particularly wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry); and/or turf and/or pastureland grass.

Preferably, in all aspects of the invention, the crops of useful plants, e.g. on or in which or at the locus of which the compounds or compositions according to the invention can be used, comprise (e.g. are) cereals (in particular non-oat cereals, more particularly non-oat non-*sorghum* non-millet cereals, even more particularly wheat, barley, rye and/or triticale), rice, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

More preferably, in all aspects of the invention, the crops of useful plants, e.g. on or in which or at the locus of which the compounds or compositions according to the invention can be used, comprise (e.g. are): wheat (e.g. winter wheat, spring wheat, or durum wheat), barley (e.g. winter or spring barley), rye, triticale, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

Even more preferably, in all aspects of the invention, the crops of useful plants, e.g. on or in which or at the locus of which the compounds or compositions according to the invention can be used, comprise (e.g. are): leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, sugarbeet, fodder beet, potato, and/or vegetables (preferably dicotyledonous vegetables).

Certain compounds of formula (I) according to the present invention are particularly efficacious vs grassy monocotyledonous weeds and appear to be selective for grassy (e.g. warm-climate grassy) monocotyledonous weed control in crops of soybean or sugarbeet (e.g. see Biological Examples 2 and 3 herein).

The term "crops" is to be understood as also including crops that have been rendered tolerant to herbicides or classes of herbicides (for example ALS, GS, EPSPS, PPO and HPPD inhibitors, and/or 2,4-D or dicamba) as a result of conventional methods of breeding or genetic engineering. Examples of crops that have been rendered tolerant e.g. to imid-azolinones (which are ALS inhibitors), such as imazamox, by conventional methods of breeding include Clearfield® summer rape (canola) and/or Clearfield® wheat and/or Clearfield® rice (all from BASF). Examples of crops that have been rendered tolerant to herbicides by genetic engineering methods include e.g. glyphosate-resistant or glufosinate-resistant maize or soybean varieties, in particular those commercially available under the trade name RoundupReady® or RoundupReady® 2 (both from Monsanto, both glyphosate-resistant) or LibertyLink® (from Bayer, glufosinate-resistant). Glufosinate-resistant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy) weeds, e.g. to be controlled and/or growth-inhibited, comprise (e.g. are) weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"); and/or in particular: *Brachiaria platyphylla* (BRAPP), *Panicum dichotomiflorum* (PANDI), and/or *Sorghum vulgare*. Alternatively or additionally, the monocotyledonous (preferably grassy) weeds, e.g. to be controlled and/or growth-inhibited, comprise volunteer corn (volunteer maize) weeds.

In one preferred embodiment of all aspects of the invention, the monocotyledonous weeds, e.g. to be controlled and/or growth-inhibited, are grassy monocotyledonous weeds; in which case they typically comprise (e.g. are): weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*; in particular: weeds from the genus *Agrostis, Alopecurus, Apera, Avena, Brachiaria, Bromus, Digitaria, Echinochloa, Eriochloa, Leptochloa, Lolium, Panicum, Phalaris, Poa, Rottboellia, Setaria* and/or *Sorghum*. Alternatively or additionally, the monocotyledonous (preferably grassy) weeds, e.g. to be controlled and/or growth-inhibited, comprise volunteer corn (volunteer maize) weeds.

In one particularly preferred embodiment of all aspects of the invention, the grassy monocotyledonous weeds, e.g. to be controlled and/or growth-inhibited, are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*; more particularly: weeds from the genus *Brachiaria, Digitaria, Echinochloa, Eriochloa, Leptochloa, Panicum, Setaria* and/or *Sorghum*. Alternatively or additionally, the grassy monocotyledonous weeds, e.g. to be controlled and/or growth-inhibited, comprise volunteer corn (volunteer maize) weeds. More preferably, the grassy monocotyledonous weeds, e.g. to be controlled and/or growth-inhibited, are "warm-season" (warm climate) grassy weeds comprising (e.g. being) weeds from the genus *Brachiaria, Cenchrus, Digitaria, Echinochloa, Eleusine, Eriochloa, Panicum, Setaria* and/or *Sorghum*; and/or the grassy monocotyledonous weeds, e.g. to be controlled and/or growth-inhibited, comprise volunteer corn (volunteer maize) weeds.

In a particular embodiment of all aspects of the invention, the grassy monocotyledonous weeds, e.g. to be controlled and/or growth-inhibited, are "cool-season" (cool climate) grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (in particular: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds; more particularly *Alopecurus, Apera, Avena, Brachiaria, Bromus, Digitaria, Echinochloa, Eriochloa, Lolium, Panicum, Phalaris, Poa, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition (2009) or 16th Edition (2012), ed. C. D. S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylamino-carbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca,* and/or *Sorghum halepense*; or can more particularly comprise *Alopecurus myosuroides, Apera spica-venti, Avena fatua, Avena sterilis, Digitaria sanguinalis, Echinochloa colona, Echinochloa crus-galli, Lolium multiflorum, Lolium rigidum, Lolium perenne, Phalaris minor, Phalaris paradoxa, Setaria viridis, Setaria faberi* and/or *Sorghum halepense.*

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.,* 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.,* 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.,* 2010, 61, pp. 317-347, e.g. see Table 4 on page 328 therein, incorporated herein by reference, for examples of such resistant weeds).

Typically, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola, Veronica* and/or *Xanthium.*

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agrochemically acceptable salt thereof) is generally from 1 to 2000 g of the compound of formula (I) per hectare (ha) (measured as the salt-free compound, i.e. excluding the weight of any associated salt counterion(s)), in particular from 5 to 1000 g/ha or from 5 to 500 g/ha or from 10 to 500 g/ha, preferably from 10 to 400 g/ha or from 20 to 300 g/ha, of the compound of formula (I) (measured as the salt-free compound, i.e. excluding the weight of any associated salt counterion(s)). In a preferred embodiment, the above rates of application are for post-emergence application of the compound of formula (I) (which optionally may be an agrochemically acceptable salt thereof).

In all aspects of the invention, the compound of formula (I) can be applied (typically to the weeds and/or to the crops of useful plants and/or to the locus thereof) pre- and/or post-emergence, but preferably is applied post-emergence.
Other Possible Uses—e.g. Possible Insecticidal and/or Acaricidal Uses The main use and purpose of the compounds of formula (I) according to the invention is their herbicidal use. However, at least some of the compounds of formula (I) may have activity against one or more types of pest (in particular pests associated with agriculture and/or food storage). For example, at least some of the compounds of formula (I) may have at least some insecticidal, acaricidal, molluscicidal and/or nematicidal activity.

At least some of the compounds of formula (I) may have activity against (and/or may help to control and/or combat) insect pests, such as one or more of: Coleoptera, Dictyoptera, Diptera, Hemiptera (including Homoptera), Hymenoptera, Isoptera, Lepidoptera, Orthoptera, Siphonaptera and/or Thysanoptera.

At least some of the compounds of formula (I) may have activity against (and/or may help to control and/or combat) acarine pests and/or pests from the order Acarina, such as one or more of: *Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and/or *Tetranychus* spp.

At least some of the compounds of formula (I) may have activity against (and/or may help to control and/or combat) other (i.e. non-insect, non-acarine) invertebrate pests, for example, nematode and/or mollusc pests.

Insects, acarines, nematodes and/or molluscs are hereinafter collectively referred to as pests.

Examples of pest species, on and/or to which the compounds of formula (I) can be tried and/or applied, include one or more of: *Myzus* spp. such as *Myzus persicae* (aphid), *Aphis* spp. such as *Aphis gossypii* (aphid) or *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. *(thrips), Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus* spp. such as *Tetranychus urticae* (two-spotted spider mite) or *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), of the Kalotermitidae (for example *Neotermes* spp.), of the Rhinotermitidae (for example *Coptotermes formosanus, Reticulitermes flavipes, R. speratu, R. virginicus, R. hesperus*, or *R. santonensis*) or of the Termitidae (for example *Globitermes sulphureus*), *Solenopsis geminata* (fire ant), *Monomorium pharaonis* (pharaoh's ant), *Damalinia* spp. or *Linognathus* spp. (biting lice or sucking lice), *Meloidogyne* spp. (root knot nematodes), *Globodera* spp. or *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*(vinegar eelworm), *Trichostrongylus* spp. (gastro intestinal nematodes) and/or *Deroceras reticulatum* (slug).

Combinations and Mixtures

In a further aspect, the present invention provides a herbicidal composition, e.g. for use in a method of controlling weeds (e.g. monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I). Preferably, in these mixtures (in particular in the specific mixtures disclosed hereinbelow), the compound of the formula (I) is one of those compounds listed in Tables 1, 2, 3, 4, 5 or 6, and/or one of the exemplified compounds (in particular one of compounds A1 to A7, A8, or P1 to P5), as disclosed herein e.g. hereinbelow, optionally present (e.g. where chemically possible) as an agrochemically acceptable salt thereof.

In particular, the following mixtures of the compound of formula (I) with one or more further herbicides are particularly disclosed:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate (see e.g. US2012/0184434A1), compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl [(1RS)-1-(2,4-dichlorophenoxyacetoxy)ethyl]phosphonate, also named Ivxiancaolin or Iüxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixture partners for the compound of formula (I) are optionally in the form of an ester (in particular an agrochemically acceptable ester) or a salt (in particular an agrochemically acceptable salt) thereof (e.g. where chemically possible). The above-mentioned mixture partners for the compound of formula (I), are generally mentioned e.g. in The Pesticide Manual, 15th Edition (2009) or 16th Edition (2012), ed. C. D. S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl] methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula 1+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+triallate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+diquat, compound of formula (I)+diquat dibromide, compound of formula (I)+esprocarb, compound of formula (I)+ethoxysulfuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6); wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, more preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5 (4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-di methoxy-1,3,5-triazin-2-yl)carbonyl]-6-fluorophenyl]-N-methyl-1,1-difluoromethanesulfonamide, CAS Reg. No. 874195-61-6);
wherein the mixture partners for the compound of formula (I) may optionally be in the form of an ester (in particular an agrochemically acceptable ester) or a salt (in particular an agrochemically acceptable salt) thereof (e.g. where chemically possible).

For applications in soybean, the following mixtures are preferred:
compound of formula (I)+acifluorfen, compound of formula (I)+acifluorfen-sodium, compound of formula (I)+ametryn, compound of formula (I)+atrazine, compound of formula (I)+bentazone, compound of formula (I)+bicyclopyrone, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chloransulam, compound of formula (I)+chloransulam-methyl, compound of formula (I)+chlorimuron, compound of formula (I)+chlorimuron-ethyl, compound of formula (I)+clethodim, compound of formula (I)+clomazone, compound of formula (I)+cyanazine, compound of formula (I)+2,4-D (especially for applications to 2,4-D-tolerant soybean, e.g. genetically-modified), compound of formula (I)+2,4-D-dimethylammonium (especially for applications to 2,4-D-tolerant soybean, e.g. genetically-modified), compound of formula (I)+2,4-D-2-ethylhexyl (especially for applications to 2,4-D-tolerant soybean, e.g. genetically-modified), compound of formula (I)+a choline salt of 2,4-D (see e.g. Examples 2 and 3 of WO2010/123871A1) (especially for applications to 2,4-D-tolerant soybean, e.g. genetically-modified), compound of formula (I)+2,4-D+glyphosate (especially for applications to 2,4-D-tolerant and/or glyphosate-tolerant soybean, e.g. genetically-modified), compound of formula (I)+2,4-D-dimethylammonium+glyphosate (especially for applications to 2,4-D-tolerant and/or glyphosate-tolerant soybean, e.g. genetically-modified), compound of formula (I)+2,4-D-2-ethylhexyl+glyphosate (especially for applications to 2,4-D-tolerant and/or glyphosate-tolerant soybean, e.g. genetically-modified), compound of formula I+a choline salt of 2,4-D+glyphosate (see e.g. Examples 2 and 3 of WO2010/123871A1) (especially for applications to dicamba-tolerant and/or glyphosate-tolerant soybean, e.g. genetically-modified), compound of formula (I)+dicamba (especially for applications to dicamba-tolerant soybean, e.g. genetically-modified), compound of formula (I)+dicamba-dimethylammonium (especially for applications to dicamba-tolerant soybean, e.g. genetically-modified), compound of formula (I)+dicamba-potassium (especially for applications to dicamba-tolerant soybean, e.g. genetically-modified), compound of formula (I)+dicamba-sodium (especially for applications to dicamba-tolerant soybean, e.g. genetically-modified), compound of formula (I)+dicamba-diglycolamine (especially for applications to dicamba-tolerant soybean, e.g. genetically-modified), compound of formula (I)+a N,N-bis-[aminopropyl]methylamine salt of dicamba (see e.g. US2012/0184434A1) (especially for applications to dicamba-tolerant soybean, e.g. genetically-modified), compound of formula (I)+dicamba+glyphosate (especially for applications to dicamba-tolerant and/or glyphosate-tolerant soybean, e.g. genetically-modified), compound of formula (I)+dicamba-dimethylammonium+glyphosate (especially for applications to dicamba-tolerant and/or glyphosate-tolerant soybean, e.g. genetically-modified), compound of formula (I)+dicamba-potassium+glyphosate (especially for applications to dicamba-tolerant and/or glyphosate-tolerant soybean, e.g. genetically-modified), compound of formula (I)+dicamba-sodium+glyphosate (especially for applications to dicamba-tolerant and/or glyphosate-tolerant soybean, e.g. genetically-modified), compound of formula (I)+dicamba-diglycolamine+glyphosate (especially for applications to dicamba-tolerant and/or glyphosate-tolerant soybean, e.g. genetically-modified), compound of formula (I)+a N,N-bis-[aminopropyl]methylamine salt of dicamba+glyphosate (especially for applications to dicamba-tolerant and/or glyphosate-tolerant soybean, e.g. genetically-modified), compound of formula (I)+diclosulam, compound of formula (I)+dimethenamid, compound of formula (I)+dimethenamid-P, compound of formula (I)+diquat, compound of formula (I)+diquat dibromide, compound of formula (I)+diuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula (I)+fluazifop, compound of formula (I)+fluazifop-butyl, compound of formula (I)+fluazifop-P, compound of formula (I)+fluazifop-P-butyl, compound of formula (I)+flufenacet, compound of formula (I)+flumetsulam, compound of formula (I)+flumioxazin, compound of formula (I)+fluthiacet, compound of formula (I)+fluthiacet-methyl, compound of formula (I)+fomesafen, compound of formula (I)+glufosinate, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+imazethapyr, compound of formula (I)+lactofen, compound of formula (I)+mesotrione, compound of formula (I)+metolachlor, compound of formula (I)+S-metolachlor, compound of formula (I)+metribuzin, compound of formula (I)+oxyfluorfen, compound of formula (I)+paraquat, compound of formula (I)+paraquat dichloride, compound of formula (I)+pendimethalin, compound of formula (I)+pyroxasulfone, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula (I)+saflufenacil, compound of formula (I)+sethoxydim, compound of formula (I)+sulfentrazone, compound of formula (I)+thifensulfuron, compound of formula (I)+thifensulfuron-methyl, compound of formula (I)+tribenuron, compound of formula (I)+tribenuron-methyl, compound of formula (I)+trifluralin, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), or compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference);

wherein the mixture partners for the compound of formula (I) may optionally be in the form of an ester (in particular an agrochemically acceptable ester) or a salt (in particular an agrochemically acceptable salt) thereof (e.g. where chemically possible).

In the above-mentioned compositions or mixtures comprising a compound of formula (I) (in particular a compound from Tables 1, 2, 3, 4, 5 or 6, and/or one of Compounds A1 to A7, A8, or P1 to P5 herein, optionally present (e.g. where chemically possible) as an agrochemically acceptable salt thereof) and one or more further herbicides, the weight ratio of the compound of formula (I) to each further herbicide can vary over a large range and is, typically, from 500:1 to 1:500 or from 300:1 to 1:500 or from 500:1 to 1:200, especially from 200:1 to 1:200 or from 150:1 to 1:200 or from 200:1 to 1:100, more especially from 100:1 to 1:100 or from 100:1 to 1:50, even more especially from 30:1 to 1:30. Typically, these weight ratios are measured as the free compound(s), i.e. excluding the weight of any associated salt counterion(s).

The compounds of formula I according to the invention can be used in combination with a safener. Preferably, in these mixtures, the compound of the formula I is one of those compounds listed (disclosed) in Tables 1, 2, 3, 4, 5 or 6, and/or one of the exemplified compounds (in particular one of compounds A1 to A7, A8, or P1 to P5) herein e.g. hereinbelow, optionally present (e.g. where chemically possible) as an agrochemically acceptable salt thereof. The following mixtures with safeners, especially, come into consideration:

compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

Preferably, in a composition or mixture comprising a compound of formula (I) (in particular, a compound from Tables 1, 2, 3, 4, 5 or 6, and/or one of Compounds A1 to A7, A8, or P1 to P5 herein, optionally present (e.g. where chemically possible) as an agrochemically acceptable salt thereof) and a safener, the safener comprises (e.g. is) benoxacor, cloquintocet acid or an agrochemically acceptable salt thereof, cloquintocet-mexyl, cyprosulfamide, mefenpyr-diethyl, isoxadifen-ethyl and/or N-(2-methoxybenzoyl)-4-[(methylaminocarbonyl)amino]benzenesulfonamide. In one particular embodiment, the safener comprises (e.g. is) cloquintocet acid or an agrochemically acceptable salt thereof, cloquintocet-mexyl, mefenpyr-diethyl and/or isoxadifen-ethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

The ratio of safener relative to the herbicide is largely dependent upon the mode of application. However, typically, the weight ratio of the compound of formula (I) to the safener can vary over a large range and is, typically, from 200:1 to 1:200, especially from 50:1 to 1:50 such as from 50:1 to 1:20, more especially from 20:1 to 1:20, even more especially from 20:1 to 1:10. As stated above, preferably, the safener comprises (e.g. is) benoxacor, cloquintocet-mexyl, cloquintocet acid or an agrochemically acceptable salt thereof, cyprosulfamide, mefenpyr-diethyl, isoxadifen-ethyl and/or N-(2-methoxybenzoyl)-4-[(methylaminocarbonyl) amino]benzenesulfonamide; in which case, more preferably, the weight ratio of the compound of formula (I) to the safener is from 50:1 to 1:20 or from 20:1 to 1:10, even more preferably from 15:1 to 1:2. Typically, these weight ratios are measured as the free compound(s), i.e. excluding the weight of any associated salt counterion(s). In the above typical or preferred embodiments, preferably, the compound of formula (I) is a compound from Tables 1, 2, 3, 4, 5 or 6, and/or one of Compounds A1 to A7, A8, or P1 to P5 herein, optionally present (e.g. where chemically possible) as an agrochemically acceptable salt thereof.

Application rates of herbicide (in particular compound of formula (I)) and/or safener: The rate of application of safener relative to the herbicide (in particular compound of formula (I)) is largely dependent upon the mode of application. In the case of field and/or soil and/or plant treatment (e.g. in a field or glasshouse): for example from 0.001 to 5.0 kg (e.g. from 1 to 1000 g) of safener per ha, preferably from 0.001 to 0.5 kg (in particular from 1 to 250 g or from 2 to 200 g or from 5 to 200 g) of safener per ha, are applied; and/or generally from 0.001 to 2 kg of herbicide (e.g. compound of formula (I)) per ha, but preferably from 0.005 to 1 kg (more preferably from 5 to 500 g or from 10 to 400 g or from 10 to 300 g or from 20 to 200 g) of herbicide (in particular compound of formula (I)) per ha, are applied. ha=hectare. Typically, these application rates are measured as the free compound, i.e. excluding the weight of any associated salt counterion(s). In field and/or plant treatment, the application of the herbicide (in particular compound of formula (I)) is preferably post-emergence.

The above-mentioned safeners and herbicides are described, for example, in the Pesticide Manual, Twelfth Edition, British Crop Protection Council, 2000; or The Pesticide Manual, 15th edition (2009) or 16th edition (2012), ed. C. D. S. Tomlin, British Crop Production Council. R-29148 is described, for example by P. B. Goldsbrough et al., Plant Physiology, (2002), Vol. 130 pp. 1497-1505 and references therein. PPG-1292 is known from WO 2009/211761. N-(2-methoxybenzoyl)-4-[(methylaminocarbonyl) amino]-benzenesulfonamide is known e.g. from EP365484.

In one particular embodiment, the composition or mixture comprising the compound of formula (I) and one or more further herbicides (e.g. as mentioned hereinabove) can be applied together with one of the safeners mentioned herein, e.g. hereinabove.

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

The following examples illustrate further but do not limit the invention.

PREPARATION EXAMPLES

Those skilled in the art will appreciate that certain compounds described herein, e.g. hereinbelow, are β-ketoenols, and as such may exist as a single tautomer or as a mixture of keto-enol and diketone tautomers as described, for example, by J. March, Advanced Organic Chemistry, third edition, John Wiley and Sons. The compounds shown hereinbelow, and in Tables T1, T2 and P1 hereinbelow, as well as those compounds shown hereinbefore in Tables 1, 2, 3, 4, 5 or 6, are drawn as an arbitrary single enol tautomer, but it should be inferred that this description covers both the diketone form and any possible enols which could arise through tautomerism. Where more than one tautomer is observed in proton ($^1$H) NMR, the data shown are for the mixture of tautomers. Furthermore, some of the compounds shown below may be drawn as single enantiomers for the purposes of simplicity, but unless specified as single enantiomers, these structures should be construed as representing a mixture of enantiomers (e.g. a racemic mixture). Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer (or the drawn structure) is the enol form.

Abbreviations Used Herein:

s=singlet; brs=broad singlet; d=doublet; m=multiplet.

| NMR | nuclear magnetic resonance |
|---|---|
| LC-MS | liquid chromatography - mass spectrometry |
| RT | room temperature (in the context of experimentals and/or temperatures) |
| RT | retention time (in the context of LCMS) |

LC-MS Analysis

Note: Compounds characterised by HPLC-MS were analysed using an Agilent 1100 Series HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.6 | 90.0 | 10.0 | 2.00 |
| 3.0 | 90.0 | 10.0 | 2.00 |

Solvent A: H$_2$O with 0.1% HCOOH
Solvent B: 0.1% HCOOH in CH$_3$CN

The characteristic values obtained for each compound were the retention time (RT, recorded in minutes) and the molecular ion, typically the cation MH+.

Example 1

Preparation of
4-Bromo-2-fluoro-6-methoxy-benzaldehyde

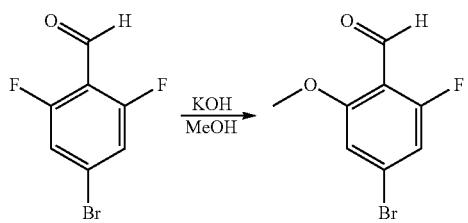

Flaked potassium hydroxide (59.575 g) was added portionwise to stirred and cooled (ice-bath) methanol (600 mL) keeping the temperature below 20° C. This solution was transferred to a dropping funnel. The starting material, 4-Bromo-2,6-difluoro-benzaldehyde (commercially available, CAS 537013-51-7, 200 g), was dissolved in methanol (1210 mL) at 25° C. The mixture was warmed to 40° C. and the potassium methoxide solution added from the dropping funnel over 20 minutes with stirring. An initial exotherm was observed which was controlled by external cooling. The reaction temperature was increased to 55° C. and heating was continued for 1 hour.

The reaction mixture was cooled to room temperature and the methanol was removed under vacuum. The resultant residue was partitioned between water (1.6 L) and ethyl acetate (1.6 L). The phases were separated and the aqueous layer extracted with further ethyl acetate (2×0.5 L). The combined organic phases were washed with water (0.5 L) and concentrated under vacuum leaving a yellow solid.

This solid was triturated with cold iso-hexane, filtered and dried in vacuo to give a yellow solid as a 4:1 mixture of the desired compound 4-bromo-2-fluoro-6-methoxy-benzaldehyde[1H-NMR (400 MHz, CDCl$_3$) 10.36 (s, 1H), 6.94-6.97 (m, 2H), 3.94 (s, 3H)] and 4-bromo-2,6-dimethoxy-benzaldehyde.

The following compounds may be made using the same method:

4-Bromo-2-fluoro-6-(2-methoxy-ethoxy)-benzaldehyde was made using 2-methoxyethanol. $^1$H-NMR (400 MHz, CDCl$_3$) 10.39 (d, 1H), 6.93-6.99 (m, 2H), 4.18-4.26 (m, 2H), 3.73-3.84 (m, 2H), 3.45 (s, 3H).

4-Bromo-2-fluoro-6-(2,2,2-trifluoro-ethoxy)-benzaldehyde. $^1$H-NMR (400 MHz, CDCl$_3$) 10.37 (d, 1H), 7.09 (dd, 1H), 6.95 (s, 1H), 4.47 (q, 2H).

2,4-dibromo-6-methoxy-benzaldehyde. $^1$H-NMR (400 MHz, CDCl$_3$) 10.34 (s, 1H), 7.44 (s, 1H), 7.11 (s, 1H), 3.92 (s, 3H).

Example 2

Preparation of
4-Bromo-2-fluoro-6-methoxy-benzaldehyde

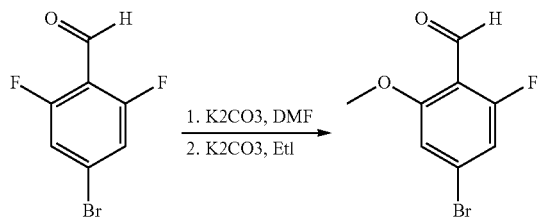

To a stirred solution of 4-bromo-2,6-difluoro-benzaldehyde (commercially available, CAS 537013-51-7, 1.00 g) in N,N-dimethylformamide (5 mL) at ambient temperature was added potassium carbonate (1.10 g) followed by water (0.408 g). The resulting suspension was heated at 90° C. After 1 hour further water (0.08 mL) was added and heating continued for another 1 hour.

The reaction mixture was cooled to ambient temperature and potassium carbonate (0.595 g) added with stirring followed by iodomethane (1.4 mL). This mixture was stirred at ambient temperature overnight.

Partitioned the reaction mixture between water and diethyl ether and extracted the aqueous layer with further diethyl ether (2×). The combined organics were washed with water, brine and dried with anhydrous magnesium sulfate.

This mixture was filtered and concentrated under vacuum to give a red-orange solid. This solid was dissolved in dichloromethane, passed through a plug of silica and concentrated to give 4-bromo-2-fluoro-6-methoxy-benzaldehyde as a cream solid.

$^1$H-NMR (400 MHz, CDCl$_3$) δ (delta) 10.37 (s, 1H), 6.94-6.97 (m, 2H), 3.94 (s, 3H).

The following compounds may be made using the same method: 4-Bromo-2-ethoxy-6-fluoro-benzaldehyde was made using ethyl iodide. $^1$H-NMR (400 MHz, CDCl$_3$) δ (delta) 10.38 (d, 1H), 6.85-6.96 (m, 2H), 4.15 (q, 2H), 1.49 (t, 3H).

Example 3

Preparation of 4-Bromo-2-fluoro-6-hydroxy-benzaldehyde

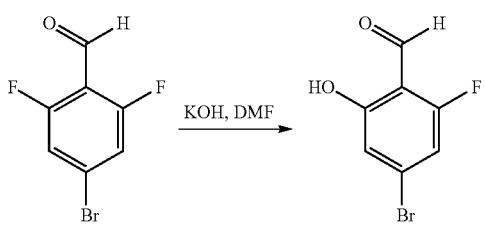 [SMILES: O=Cc1c(F)cc(Br)cc1F ; O=Cc1c(O)cc(Br)cc1F]

To a stirred solution of 4-bromo-2,6-difluoro-benzaldehyde (commercially available, CAS 537013-51-7, 2.000 g) in N,N-dimethylformamide (10 mL) was added a solution of potassium hydroxide (1.015 g) in water (4 mL) at ambient temperature. The yellow solution was heated at 60° C. for 2 hours. The reaction mixture was cooled and poured onto iced water and extracted with diethylether. The aqueous layer was separated and taken to pH 2 by addition of concentrated hydrochloric acid. Unexpectedly no solid crashed out of aqueous even when cooled.

It was noted that upon standing a yellow solid had crashed out of the organic phase. This solid was collected by filtration and dissolved in water. The aqueous filtrate was taken to pH 2 by addition of concentrated hydrochloric acid and the resulting pale yellow solid was filtered and dried to give 4-bromo-2-fluoro-6-hydroxy-benzaldehyde. $^1$H-NMR (400 MHz, CDCl$_3$) δ (delta) 11.57 (s, 1H), 10.20 (s, 1H), 6.99 (s, 1H), 6.86 (dd, 1H).

Example 4

Preparation of 4-Bromo-2-difluoromethoxy-6-fluoro-benzaldehyde

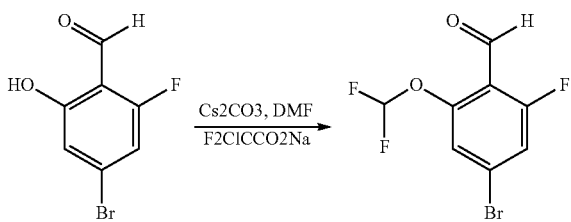

To a solution of 4-bromo-2-fluoro-6-hydroxy-benzaldehyde (see e.g. Example 3, 1.451 g) in N,N-dimethylformamide (4.7 mL) at ambient temperature was added cesium carbonate (3.022 g) giving a yellow suspension which was stirred for 5 minutes. Sodium 2-chloro-2,2-difluoro-acetic acid (2.339 g) was added to the suspension followed by water (0.86 mL). This mixture was heated at 85° C. for 2.5 hours. The reaction mixture was cooled, poured into ice-water and extracted with diethyl ether (×2). The combined organic layers were washed with water, dried with magnesium sulfate and concentrated in vacuo to leave a brown oil. The brown oil was purified by column chromatography on silica eluting with 0-15% ethyl acetate in iso-hexane to give 4-bromo-2-(difluoromethoxy)-6-fluoro-benzaldehyde as a yellow oil. $^1$H-NMR δ (delta) (400 MHz, CDCl$_3$) 10.31 (s, 1H), 7.27-7.33 (m, 1H), 6.44-6.83 (m, 1H).

Example 5

Preparation of 3-(4-Bromo-2-fluoro-6-methoxy-benzylidene)-bicyclo[2.2.1]heptan-2-one

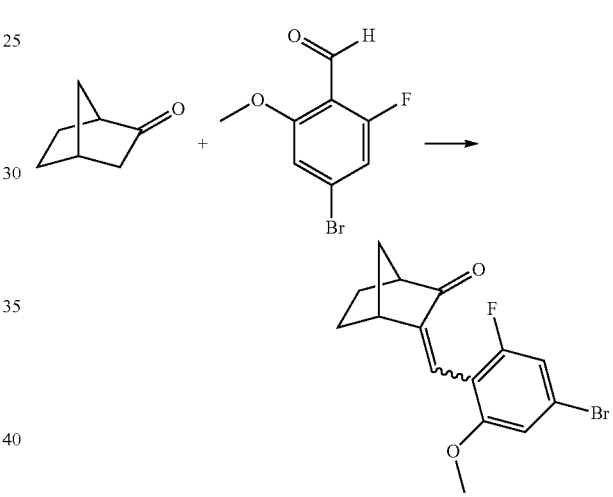

Under an atmosphere of nitrogen 4-bromo-2-fluoro-6-methoxy-benzaldehyde (see e.g. Example 1, 126.924 g) and norbornan-2-one (commercially available, CAS 497-38-1, 44.996 g) were dissolved in tert-butyl alcohol (1634 mL) and the mixture was stirred and warmed to 40° C. To this solution was added portionwise potassium tert-butoxide (61.118 g) maintaining the temperature below 43° C. On completion of the addition the mixture was heated to 80° C. for 1 hour.

The reaction mixture was cooled to room temperature and the solvent was removed under vacuum. The resulting residue was partitioned between water (1 L) and ethyl acetate (1 L) and the aqueous layer extracted with further ethyl acetate (2×0.5 L). The combined organic phases were washed with water (0.5 L). The organic phase was concentrated under vacuum to leave a yellow solid which was purified by colHumn chromatography on silica eluting with 0-25% ethyl acetate in iso-hexane to give 3-(4-bromo-2-fluoro-6-methoxy-benzylidene)-bicyclo[2.2.1]heptan-2-one as a light yellow solid.

$^1$H-NMR (400 MHz, CDCl$_3$) δ (delta) 7.00 (s, 1H), 6.91-6.94 (m, 1H), 6.84 (m, 1H), 3.84 (s, 3H), 3.11 (brs, 1H), 2.78 (brs, 1H), 1.91-1.94 (m, 2H), 1.61-1.75 (m, 4H).

Example 6

Preparation of 4-(4-Bromo-2-fluoro-6-methoxy-benzylidene)-3-oxa-bicyclo[3.2.1]octan-2-one

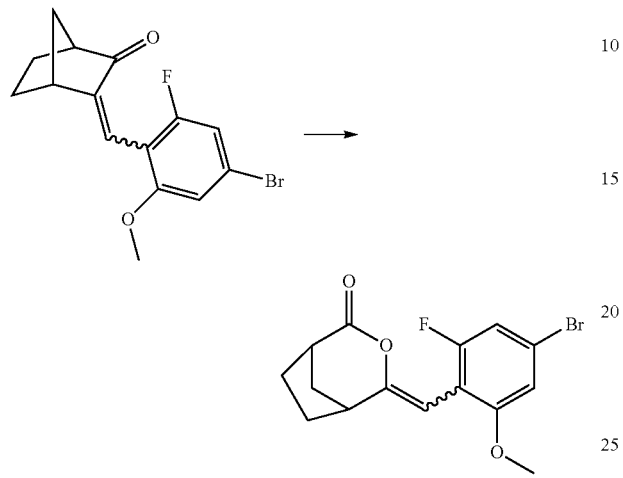

To a stirred solution of 3-(4-bromo-2-fluoro-6-methoxy-benzylidene)-bicyclo[2.2.1]heptan-2-one (see e.g. Example 5, 5.658 g) in tert-butyl alcohol (18.80 mL) was added selenium dioxide (0.0696 g) followed by hydrogen peroxide (5 mL) in one portion. The resultant yellow solution was stirred at room temperature for 3 days.

The reaction mixture was diluted with ethyl acetate (20 mL) and water (10 mL) and cooled in an ice bath. Sodium metabisulfite (2% aqueous solution, 50 mL) was added in 10 mL portions with stirring. Further sodium metabisulfite (10% aqueous solution) was added portionwise, maintaining the internal temperature at <20° C., until the mixture tested negative for peroxides. In total 60 mL of 10% sodium metabisulfite solution was added. Further ethyl acetate (20 mL) was added and the phases were separated. The aqueous layer was further extracted with ethyl acetate (1×20 mL). The combined organic layers were washed with a 50% water/brine mixture, followed by a brine wash and dried with magnesium sulfate. Concentration of the dried organic layer gave a yellow gum which was purified by column chromatography on silica eluting with 0-15% ethyl acetate in iso-hexane to give 4-(4-bromo-2-fluoro-6-methoxy-benzylidene)-3-oxa-bicyclo[3.2.1]octan-2-one as a yellow gum. $^1$H-NMR (400 MHz, CDCl$_3$) 6.90-6.93 (m, 1H), 6.83 (s, 1H), 5.66 (s, 1H), 3.83 (s, 3H), 3.07-3.10 (m, 1H), 3.02 (m, 1H), 1.97-2.07 (m, 5H), 1.62-1.67 (m, 1H).

LC-MS RT 1.06 min MH+341

On prolonged standing at room temperature (2 weeks) the material gave a yellow solid.

Example 7

Preparation of 3-(4-Bromo-2-fluoro-6-methoxy-phenyl)-bicyclo[3.2.1]octane-2,4-dione

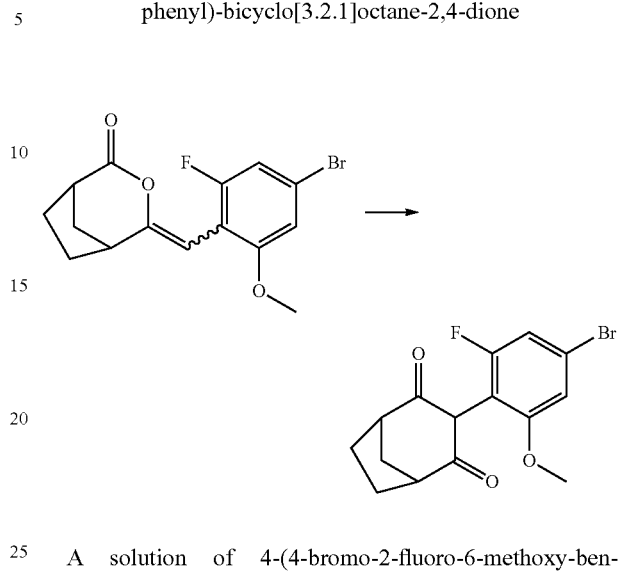

A solution of 4-(4-bromo-2-fluoro-6-methoxy-benzylidene)-3-oxa-bicyclo[3.2.1]octan-2-one (see e.g. Example 6, 38.956 g) in toluene (320 mL) was purged with nitrogen. To this stirring solution at 21° C. was added dropwise, over 13 minutes, Eaton's reagent (commercially available, CAS 39394-84-8, 7.7 wt. % phosphorus pentoxide in methanesulfonic acid, 150 mL). The mixture was heated with stirring to 70° C. and heated at this temperature for 80 minutes.

The reaction mixture was cooled to 10° C. and water (50 mL) was added dropwise maintaining an internal temperature between 10 and 16° C. To this mixture, again maintaining an internal temperature between 10 and 16° C., was added 1.5 M aqueous sodium hydroxide (100 mL) followed by 3M aqueous sodium hydroxide (1.5 L) to get the pH to 14. Once at pH 14, the mixture was warmed to 24° C. and stirred for 30 minutes.

Water (750 mL) and ethyl acetate (400 mL) were added and the mixture was separated. The aqueous phase was washed with further ethyl acetate (400 mL). The aqueous phase was acidified to pH 1 by addition of concentrated hydrochloric acid (about 100 mL) with stirring. The resulting precipitated solid was filtered off under vacuum, washed with water and dried in vacuo to give 3-(4-bromo-2-fluoro-6-methoxy-phenyl)-bicyclo[3.2.1]octane-2,4-dione as a white solid.

$^1$H-NMR (400 MHz, CDCl$_3$) (atropisomers present) δ (delta) 6.93-6.98 (m, 1H), 6.88 (s, 1H), 6.18 (brs, 0.5H), 5.93 (brs, 0.5H), 3.79 (m, 3H), 3.00-3.02 (m, 2H), 2.07-2.27 (m, 3H), 1.91-2.00 (m, 1H), 1.72-1.83 (m, 1H), 1.61-1.69 (m, 1H).

LC-MS RT 0.65 min MH+341.

Example 8

Preparation of 3'-[4-bromo-2-fluoro-6-(2-methoxyethoxy)-phenyl]spiro[norbornane-3,2'-oxirane]-2-one

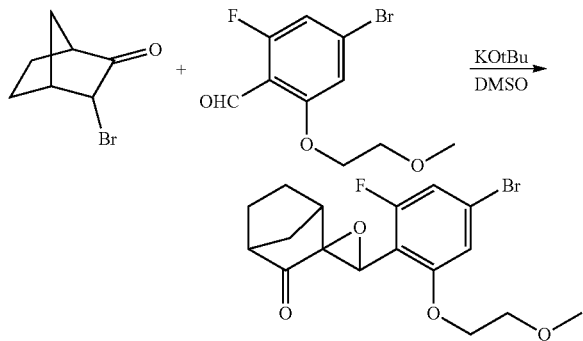

Potassium tert-butoxide (1M solution in tetrahydrofuran, 4.57 ml) was added drop wise to a stirred solution of 4-bromo-2-fluoro-6-(2-methoxyethoxy)benzaldehyde (see e.g. Example 1, 1.055 g) and 3-bromonorbornan-2-one (0.864 g) in anhydrous dimethylsulfoxide (19 ml) at ambient temperature. The reaction was stirred for 1 hour. The reaction was quenched with saturated aqueous ammonium chloride and extracted twice with ethyl acetate. The combined organic layers were dried with magnesium sulfate, filtered and concentrated under vacuum.

The 3'-[4-bromo-2-fluoro-6-(2-methoxyethoxy)phenyl]spiro[norbornane-3,2'-oxirane]-2-one was used crude in the next step without purification.

The following compounds may be made using the same method:
3'-[4-bromo-2-(difluoromethoxy)-6-fluoro-phenyl]spiro[norbornane-3,2'-oxirane]-2-one
3'-(4-bromo-2-ethoxy-6-fluoro-phenyl)spiro[norbornane-3,2'-oxirane]-2-one
3'-(2,4-dibromo-6-methoxy-phenyl)spiro[norbornane-3,2'-oxirane]-2-one
3'-(4-bromo-2-fluoro-6-methoxy-phenyl)-1,7,7-trimethyl-spiro[norbornane-3,2'-oxirane]-2-one
3'-[4-bromo-2-fluoro-6-(2,2,2-trifluoroethoxy)phenyl]spiro[norbornane-3,2'-oxirane]-2-one.

Example 9

Preparation of 3-[4-bromo-2-fluoro-6-(2-methoxyethoxy)phenyl]-bicyclo[3.2.1]octane-2,4-dione

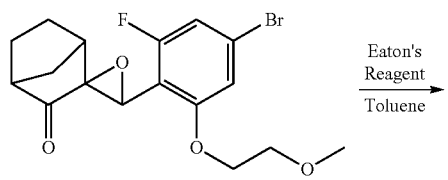

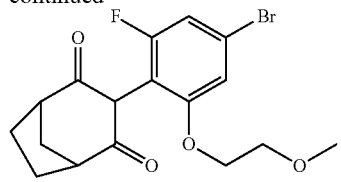

The crude 3'-[4-bromo-2-fluoro-6-(2-methoxyethoxy) phenyl]spiro[norbornane-3,2'-oxirane]-2-one (see e.g. Example 8) was stirred in toluene (19 mL) and Eaton's reagent (2.665 mL) was added. The reaction was heated to 70° C. for 2 hours.

The reaction mixture was cooled and made basic to pH 14 using 2M potassium hydroxide and washed twice with dichloromethane. The aqueous layer was acidified to pH 1 with concentrated hydrochloric acid and extracted twice with dichloromethane. The combined organic layers were dried with magnesium sulfate, filtered and concentrated under vacuum to afford an off-white solid. The majority of this material was used in subsequent cross-coupling reactions and a portion of the material (70 mg) was purified by column chromatography on silica eluting with 0-80% ethyl acetate in iso-hexane to give 3-[4-bromo-2-fluoro-6-(2-methoxyethoxy)phenyl]bicyclo[3.2.1]octane-2,4-dione as a white solid.

$^1$H-NMR (400 MHz, CD$_3$OD) δ (delta) 6.90-7.00 (m, 2H), 4.00-4.10 (m, 2H), 3.60-3.69 (m, 2H), 3.35-3.41 (m, 3H), 2.95-3.02 (m, 2H), 2.14-2.23 (m, 3H), 1.86-1.92 (m, 1H), 1.78-1.85 (m, 1H), 1.65-1.73 (m, 1H).

The following compounds could be made using the same method:
3-[4-bromo-2-(difluoromethoxy)-6-fluoro-phenyl]bicyclo[3.2.1]octane-2,4-dione. $^1$H-NMR (400 MHz, CDCl$_3$) δ (delta) 7.16-7.21 (m, 2H), 6.12-6.54 (m, 1H), 3.02-3.04 (m, 2H), 2.09-2.29 (m, 4H), 1.79-2.02 (m, 2H), 1.63-1.68 (m, 1H).
3-(4-bromo-2-ethoxy-6-fluoro-phenyl)bicyclo[3.2.1]octane-2,4-dione $^1$H-NMR (400 MHz, CD$_3$OD) δ (delta) 6.93-6.99 (m, 1H), 6.87 (d, 1H), 6.04 (s, 1H), 3.90-4.07 (m, 2H), 3.02 (d, 2H), 2.08-2.24 (m, 3H), 1.92 (s, 1H), 1.59-1.77 (m, 2H), 1.29-1.37 (m, 3H).
3-(2,4-dibromo-6-methoxy-phenyl)bicyclo[3.2.1]octane-2,4-dione $^1$H-NMR (400 MHz, CD$_3$OD) δ (delta) 7.34-7.35 (m, 1H), 7.07-7.10 (m, 1H), 3.69-3.73 (m, 3H), 2.94-2.97 (m, 2H), 2.15-2.25 (m, 3H), 1.80-1.92 (m, 2H), 1.64-1.70 (m, 1H).
3-(4-bromo-2-fluoro-6-methoxy-phenyl)-5,8,8-trimethyl-bicyclo[3.2.1]octane-2,4-dione $^1$H-NMR (400 MHz, CD$_3$OD) δ (delta) 6.90-6.97 (m, 2H), 3.74-3.76 (m, 3H), 2.53-2.55 (m, 1H), 2.30-2.37 (m, 1H), 1.93-2.01 (m, 1H), 1.70-1.84 (m, 2H), 1.09-1.15 (m, 6H), 1.02 (s, 3H).
3-[4-bromo-2-fluoro-6-(2,2,2-trifluoroethoxy)phenyl]bicyclo[3.2.1]octane-2,4-dione $^1$H-NMR (400 MHz, CD$_3$OD) δ (delta) 7.03-7.24 (m, 2H), 4.42-4.53 (m, 2H), 3.00 (brs, 2H), 2.13-2.23 (m, 3H), 1.76-1.88 (m, 2H), 1.66-1.74 (m, 1H).

Example 10

Preparation of 3-(2-Fluoro-6-methoxy-4-prop-1-ynyl-phenyl)-bicyclo[3.2.1]octane-2,4-dione (Table T1, Compound A1)

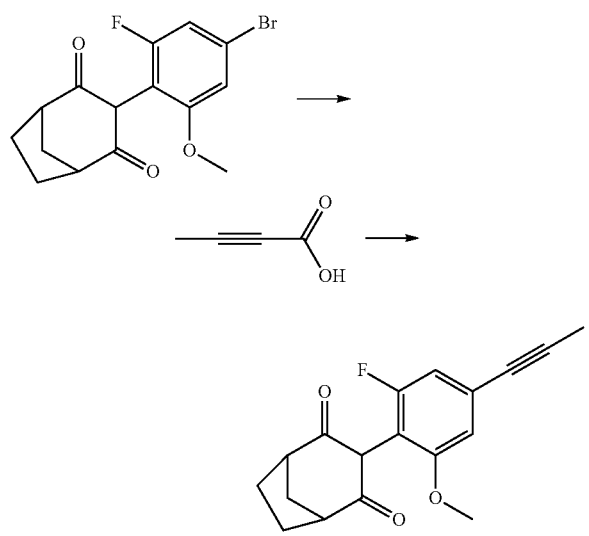

To a 5 ml microwave vial was added 3-(4-bromo-2-fluoro-6-methoxy-phenyl)bicyclo[3.2.1]octane-2,4-dione (see e.g. Example 9, 0.15 g), 2-butynoic acid (commercially available, CAS 590-93-2, 0.0407 g), bis(triphenylphosphine)palladium(II)dichloride (commercially available, CAS 13965-03-2, 0.0156 g) and 1,4-bis-(diphenylphosphino)butane (commercially available, CAS 7688-25-7, 0.0187 g). The vial was evacuated and purged with nitrogen (×3). Methyl sulfoxide (2 mL) was added followed by tetrabutylammonium fluoride (commercially available, CAS 429-41-4, 1 mol/L in THF, 1.32 mL) and mixture was heated in a microwave reactor at 110° C. for 40 minutes. The reaction mixture was partitioned between water and ethyl acetate. The aqueous phase was extracted with further ethyl acetate (×2). The combined organic layers were washed with brine and dried with magnesium sulfate. Concentration of the dried organic layer gave a yellow gum which was purified by column chromatography on silica eluting with 0-100% ethyl acetate in iso-hexane to give 3-(2-fluoro-6-methoxy-4-prop-1-ynyl-phenyl)-bicyclo[3.2.1]octane-2,4-dione as an off-white solid.

$^1$H-NMR (400 MHz, CDCl$_3$) δ (delta) 6.70-6.81 (m, 2H), 3.71-3.77 (m, 3H), 3.19-3.22 (m, 1H), 3.02 (m, 1H), 2.08-2.28 (m, 4H), 2.04-2.05 (m, 3H), 1.92-1.97 (m, 1H), 1.60-1.67 (m, 1H). LC-MS RT atropisomers present: UV detector two peaks present RT 0.67 and 0.68 min, Corona one peak at 0.69 min, MH+301.

Compounds A2 to A7 in Table T1 could be prepared using this or a similar method.

Example 11

Preparation of [3-(2-fluoro-6-methoxy-4-prop-1-ynyl-phenyl)-4-oxo-2-bicyclo[3.2.1]oct-2-enyl]benzoate

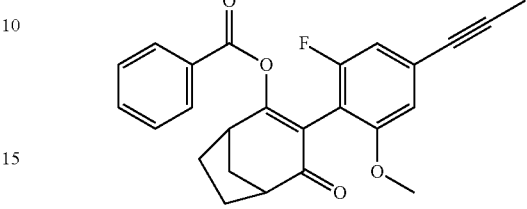

To a solution of 3-(2-fluoro-6-methoxy-4-prop-1-ynyl-phenyl)bicyclo[3.2.1]octane-2,4-dione (0.100 g) and 4-(dimethylamino)pyridine (0.002 g) in dichloromethane (3.33 mL) was added pyridine (0.054 mL) and benzoyl chloride (0.058 mL). The reaction was stirred at room temperature for 1 hour, and then was concentrated and purified by column chromatography on silica eluting with 5-55% ethyl acetate in iso-hexane to give [3-(2-fluoro-6-methoxy-4-prop-1-ynyl-phenyl)-4-oxo-2-bicyclo[3.2.1]oct-2-enyl]benzoate (0.118 g).

Example 12

Preparation of 3-(4-bromo-2-fluoro-6-methoxy-phenyl)-2-methoxy-bicyclo[3.2.1]oct-2-en-4-one

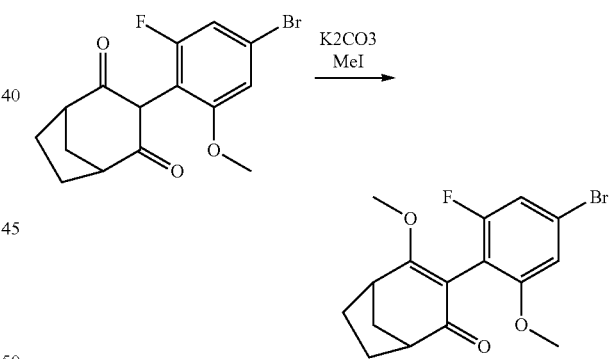

To a solution of 3-(4-bromo-2-fluoro-6-methoxy-phenyl)bicyclo[3.2.1]octane-2,4-dione (1 g, e.g. as prepared in Example 7) in acetone (29.31 mL) was added potassium carbonate (1.02292 g), iodomethane (0.365 mL) and water (0.1466 mL). The reaction mixture was stirred at room temperature for 4 hours. At this point a few drops of water were added and the reaction was allowed to stir at for a further 3 hours and then allowed to stand overnight. The reaction was quenched with water and extracted with dichloromethane (3×). The organic phases were combined, dried with magnesium sulfate and concentrated under reduced pressure to give 3-(4-bromo-2-fluoro-6-methoxy-phenyl)-2-methoxy-bicyclo[3.2.1]oct-2-en-4-one (0.818 g) as a brown gum.

$^1$H NMR (500 MHz, CDCl$_3$) δ (delta) 6.87 (ddd, 1H), 6.81 (d, 1H), 3.74 (d, 3H), 3.70 (d, 3H), 3.25 (t, 1H), 3.02

(d, 1H), 2.22 (dd, 1H), 2.16-2.08 (m, 2H), 1.95-1.88 (m, 1H), 1.84-1.76 (m, 1H), 1.67 (qd, 1H).

Example 13

Preparation of 3-[2-fluoro-6-methoxy-4-(2-trimethylsilylethynyl)phenyl]-2-methoxy-bicyclo[3.2.1]oct-2-en-4-one

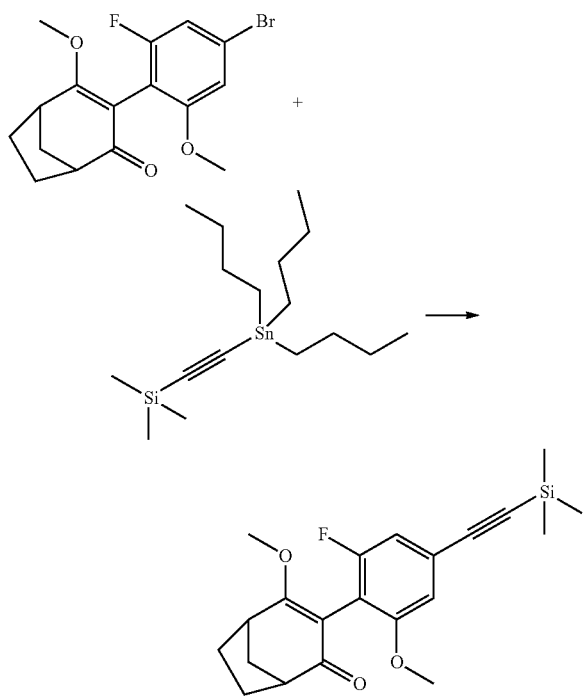

To a solution of 3-(4-bromo-2-fluoro-6-methoxy-phenyl)-2-methoxy-bicyclo[3.2.1]oct-2-en-4-one (0.8 g) in toluene (40 mL) was added [1,1'-bis(diphenylphosphino)ferrocene]-dichloropalladium (II) (0.08 g, CAS 72287-26-4) and trimethyl(2-tributylstannylethynyl)silane (1 g) and the reaction stirred at 160 C in air for 1.25 hours. The reaction was allowed to cool to room temperature and filtered through celite. The filtrate was partitioned between water and ethyl acetate and the aqueous phase was extracted with further ethyl acetate (3×). The combined organic layers were washed with brine, dried with magnesium sulphate, concentrated under reduced pressure and purified by chromatography on silica eluting with ethyl acetate in iso-hexane to give 3-[2-fluoro-6-methoxy-4-(2-trimethylsilylethynyl)phenyl]-2-methoxy-bicyclo[3.2.1]oct-2-en-4-one (0.609 g) as a brown gum.

$^1$H NMR (500 MHz, CDCl$_3$) δ (delta)=6.80 (ddd, 1H), 6.75 (d, 1H), 3.77-3.72 (m, 3H), 3.66 (d, 3H), 3.21 (t, 1H), 3.04-3.00 (m, 1H), 2.22 (dd, 1H), 2.16-2.08 (m, 2H), 1.95-1.89 (m, 1H), 1.84-1.76 (m, 1H), 1.66 (qd, 1H), 0.24 (s, 9H).

Example 14

Preparation of 3-(4-ethynyl-2-fluoro-6-methoxy-phenyl)-2-methoxy-bicyclo[3.2.1]oct-2-en-4-one

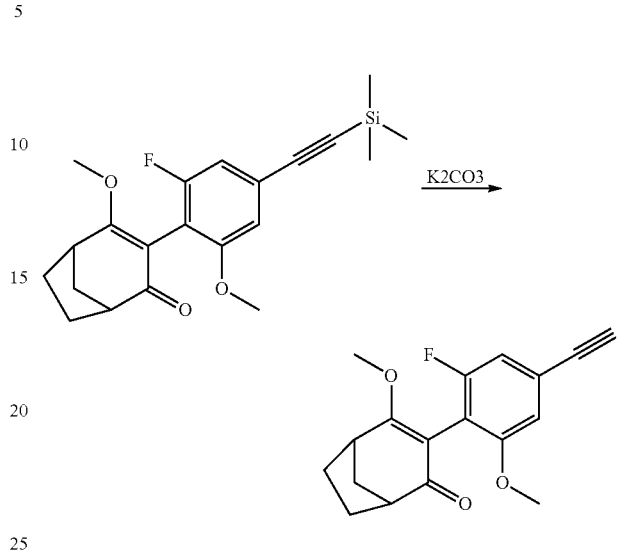

To a solution of 3-[2-fluoro-6-methoxy-4-(2-trimethylsilylethynyl)phenyl]-2-methoxy-bicyclo[3.2.1]oct-2-en-4-one (0.600 g) in methanol (16.1 mL) was added potassium carbonate (0.452 g) and the mixture stirred at room temperature for 2 hours. The reaction was diluted with water and acidified with 2M hydrochloric acid and extracted with dichloromethane (3×). The organic phases were combined, dried with magnesium sulfate and concentrated under reduced pressure to give 3-(4-ethynyl-2-fluoro-6-methoxy-phenyl)-2-methoxy-bicyclo[3.2.1]oct-2-en-4-one (415 mg) as a brown gum.

$^1$H NMR (400 MHz, CDCl$_3$) δ (delta)=6.83 (ddd, 1H), 6.78 (d, 1H), 3.77-3.72 (m, 3H), 3.71-3.67 (m, 3H), 3.23 (brs, 1H), 3.06 (s, 1H), 3.02 (brs, 1H), 2.23 (d, 1H), 2.16-2.09 (m, 2H), 1.96-1.89 (m, 1H), 1.85-1.77 (m, 1H), 1.70-1.64 (m, 1H).

Example 15

Preparation of 3-[4-(2-chloroethynyl)-2-fluoro-6-methoxy-phenyl]-2-methoxy-bicyclo[3.2.1]oct-2-en-4-one

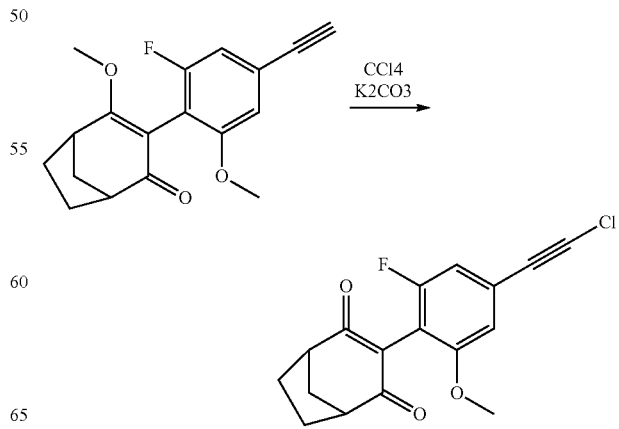

To a solution of 3-(4-ethynyl-2-fluoro-6-methoxy-phenyl)-2-methoxy-bicyclo[3.2.1]oct-2-en-4-one (0.100 g) in carbon tetrachloride (0.999 mL) was added potassium carbonate (0.0514 g) and tetrabutylammonium fluoride trihydrate (0.158 g) and the reaction stirred at room temperature for 1 hour 45 min. The reaction mixture was concentrated and used crude in the next step.

Example 16

Preparation of 3-[4-(2-chloroethynyl)-2-fluoro-6-methoxy-phenyl]bicyclo[3.2.1]octane-2,4-dione

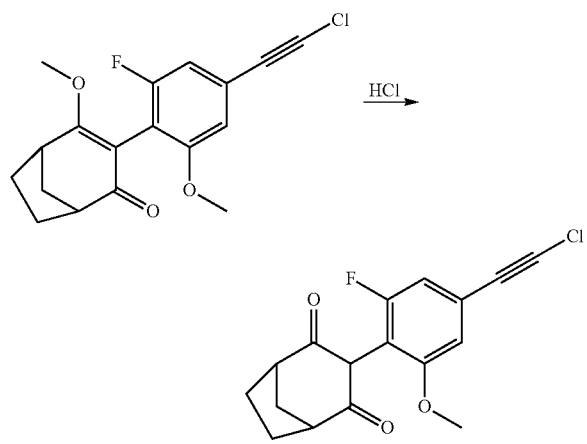

Crude 3-[4-(2-chloroethynyl)-2-fluoro-6-methoxy-phenyl]-2-methoxy-bicyclo[3.2.1]oct-2-en-4-one was dissolved in acetone (1.99 mL) and hydrochloric acid (2M) (1.99 mL) was added and the reaction was heated at 60° C. for 1 hour.

The reaction was concentrated and purified by chromatography on silica eluting with ethyl acetate in iso-hexane to give 3-[4-(2-chloroethynyl)-2-fluoro-6-methoxy-phenyl]bicyclo[3.2.1]octane-2,4-dione (25 mg) as a colourless gum.

$^1$H NMR (400 MHz, CDCl$_3$) δ (delta)=6.85-6.72 (m, 2H), 3.77-3.69 (m, 3H), 2.99 (brs, 2H), 2.25-2.14 (m, 2H), 2.13-2.04 (m, 2H), 1.82 (t, 2H).

Additional compounds in Table T1 and Table P1 below illustrate the present invention, and are particular and/or preferred embodiments of the compounds of formula (I) according to the present invention. For the most part, these compounds can generally be prepared by method(s) similar to those disclosed in the Examples hereinabove and/or disclosed in the "Processes for preparation of compounds" section hereinabove using appropriate starting materials, and/or in an analogous manner.

TABLE T1

| Compound Number | Structure | $^1$H NMR δ (delta) (CDCl$_3$ unless stated), or other physical data |
|---|---|---|
| A1 | 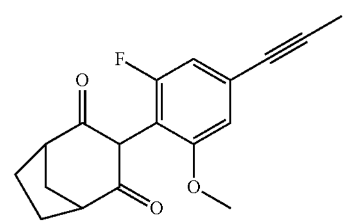 [SMILES: CC#Cc1cc(F)c(C2C(=O)C3CCC(C3)C2=O)c(OC)c1] | $^1$H NMR δ: 6.70-6.81 (m, 2H), 3.71-3.77 (m, 3H), 3.19-3.22 (m, 1H), 3.02 (m, 1H), 2.08-2.28 (m, 4H), 2.04-2.05 (m, 3H), 1.92-1.97 (m, 1H), 1.60-1.67 (m, 1H). 1H missing due to cyclic dione proton exchange. |
| A2 | 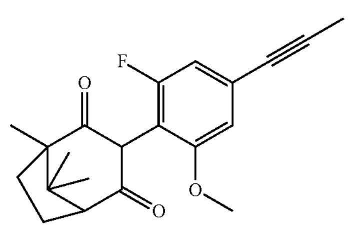 [SMILES: CC#Cc1cc(F)c(C2C(=O)C3CCC(C)(C2=O)C3(C)C)c(OC)c1] | $^1$H NMR (d$_4$-methanol) δ: 6.76-6.78 (m, 1H), 6.68-6.72 (m, 1H), 3.72-3.74 (m, 3H), 2.52-2.54 (m, 1H), 2.32-2.35 (m, 1H), 2.04 (s, 3H), 1.93-2.00 (m, 1H), 1.73-1.85 (m, 2H), 1.09-1.15 (m, 6H), 1.02 (s, 3H). 1H missing due to cyclic dione proton exchange. |
| A3 | 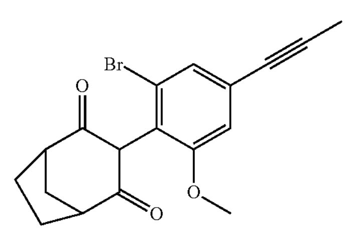 [SMILES: CC#Cc1cc(Br)c(C2C(=O)C3CCC(C3)C2=O)c(OC)c1] | $^1$H NMR δ: 7.26-7.29 (m, 1H), 6.86-6.87 (m, 1H), 5.59-5.67 (m, 1H), 3.70-3.74 (m, 3H), 3.01-3.02 (m, 2H), 2.24-2.30 (m, 1H), 2.09-2.13 (m, 2H), 2.05 (s, 3H), 1.78-1.96 (m, 2H), 1.62-1.69 (m, 1H) |

TABLE T1-continued

| Compound Number | Structure | $^1$H NMR δ (delta) (CDCl$_3$ unless stated), or other physical data |
|---|---|---|
| A4 | 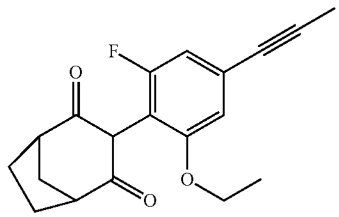 [SMILES: CC#Cc1cc(F)c(C2C(=O)C3CCC(C3)C2=O)c(OCC)c1] | $^1$H NMR (d$_4$-methanol) δ: 6.72-6.74 (m, 1H), 6.65-6.69 (m, 1H), 3.91-4.01 (m, 2H), 2.97-2.99 (m, 2H), 2.15-2.20 (m, 3H), 2.03 (s, 3H), 1.80-1.86 (m, 2H), 1.66-1.72 (m, 1H), 1.26-1.33 (m, 3H). 1H missing due to cyclic dione proton exchange. |
| A5 | 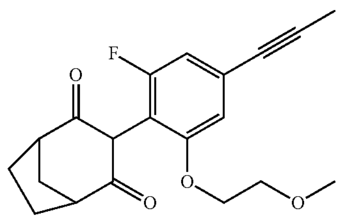 [SMILES: CC#Cc1cc(F)c(C2C(=O)C3CCC(C3)C2=O)c(OCCOC)c1] | $^1$H NMR (d$_4$-methanol) δ: 6.75-6.79 (m, 1H), 6.69-6.71 (m, 1H), 3.99-4.07 (m, 2H), 3.62-3.68 (m, 2H), 3.36-3.40 (m, 3H), 2.97-2.99 (m, 2H), 2.14-2.23 (m, 3H), 2.03 (s, 3H), 1.80-1.90 (m, 2H), 1.67-1.72 (m, 1H). 1H missing due to cyclic dione proton exchange. |
| A6 | 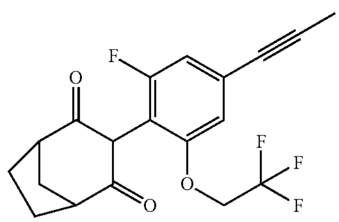 [SMILES: CC#Cc1cc(F)c(C2C(=O)C3CCC(C3)C2=O)c(OCC(F)(F)F)c1] | $^1$H NMR (d$_4$-methanol) δ: 6.76-6.88 (m, 2H), 4.37-4.47 (m, 2H), 2.99 (brs, 2H), 2.14-2.22 (m, 3H), 2.03-2.05 (m, 3H), 1.83-1.85 (m, 2H), 1.68-1.72 (m, 1H). 1H missing due to cyclic dione proton exchange. |
| A7 | 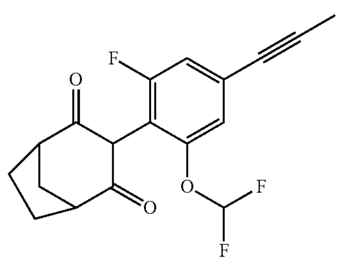 [SMILES: CC#Cc1cc(F)c(C2C(=O)C3CCC(C3)C2=O)c(OC(F)F)c1] | $^1$H NMR (d$_4$-methanol) δ: 6.94-7.01 (m, 2H), 6.34-6.77 (m, 1H), 3.01 (m, 2H), 2.18-2.21 (m, 3H), 2.05 (s, 3H), 1.80-1.88 (m, 2H), 1.69-1.74 (m, 1H). 1H missing due to cyclic dione proton exchange. |
| A8 | 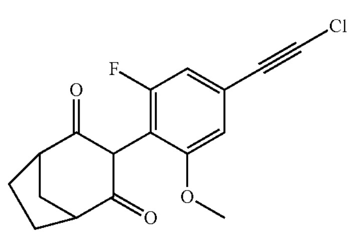 [SMILES: COc1cc(C#CCl)cc(F)c1C1C(=O)C2CCC(C2)C1=O] | $^1$H NMR δ: 6.85-6.72 (m, 2H), 3.77-3.69 (m, 3H), 2.99 (brs, 2H), 2.25-2.14 (m, 2H), 2.13-2.04 (m, 2H), 1.82 (t, 2H). |
| A9 | 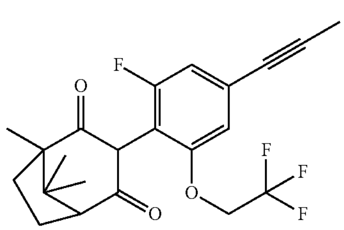 [SMILES: CC#Cc1cc(F)c(C2C(=O)C3CCC(C)(C2=O)C3(C)C)c(OCC(F)(F)F)c1] | $^1$H NMR (d$_4$-methanol) δ: 6.77-6.86 (m, 2H) 4.38-4.49 (m, 2H) 3.37 (brs, 1H) 2.51-2.57 (m, 1H) 2.34 (d, 1H) 2.03 (d, 3H) 1.91-1.99 (m, 1H) 1.73-1.84 (m, 1H) 1.07-1.16 (m, 6H) 1.02 (d, 3H). 1H missing due to cyclic dione proton exchange. |

TABLE T1-continued

| Compound Number | Structure | $^1$H NMR δ (delta) (CDCl$_3$ unless stated), or other physical data |
|---|---|---|
| A10 | 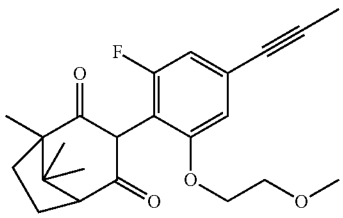 | $^1$H NMR (d$_4$-methanol) δ: 6.77 (d, 1H) 6.70 (t, 1H) 3.98-4.08 (m, 2H) 3.63 (t, 2H) 3.35-3.36 (m, 3H) 3.24-3.26 (m, 1H) 2.50-2.55 (m, 1H) 2.31 (d, 1H) 2.03 (d, 3H) 1.71-2.01 (m, 2H) 1.07-1.14 (m, 6H) 1.03 (s, 3H). 1H missing due to cyclic dione proton exchange. |

It should be noted that certain compounds of the invention may exist as a mixture of isomers, including sometimes atropisomers, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

TABLE T2

The following compound B1 is not a compound of formula (I) according to the present invention. However, a further, independent, aspect of the invention provides a compound B1, optionally present as an agrochemically acceptable salt (e.g. metal, sulfonium or ammonium salt) thereof:

| Compound Number | Structure | $^1$H NMR δ (delta) (CDCl$_3$ unless stated), or other physical data |
|---|---|---|
| B1 | 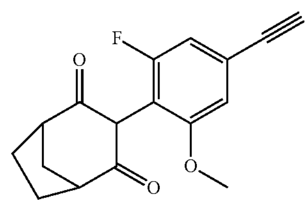 [SMILES: C#Cc1cc(F)c(C2C(=O)C3CCC(C3)C2=O)c(OC)c1] | Compound synthesized and tested (see Biological Examples) |

TABLE P1

Additional compounds in Table P1 below illustrate the present invention, and are preferred embodimens of the compounds of formula (I) according to the present invention.

| Compound Number | Structure | $^1$H NMR δ (delta) (CDCl$_3$ unless stated), or other physical data |
|---|---|---|
| P1 | 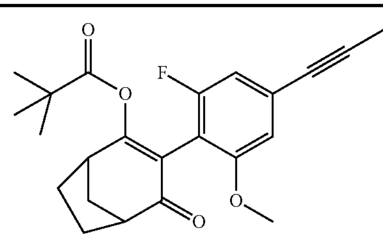 | $^1$H NMR (400 MHz, CDCl$_3$) 6.64-6.74 (m, 2H), 3.70 (d, 3H), 3.03-3.14 (m, 2H), 2.39 (d, 1H), 2.11-2.24 (m, 2H), 2.01-2.09 (m, 1H), 2.04 (s, 3H), 1.75-1.88 (m, 1H), 1.71 (m, 1H), 1.02-1.09 (m, 9H) |
| P2 | 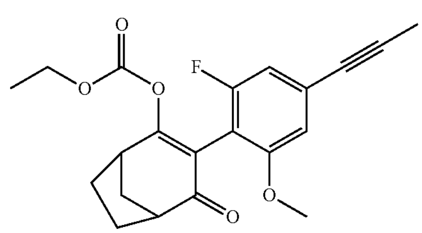 [SMILES: CC#Cc1cc(F)c(C2=C(OC(=O)OCC)C3CCC(C3)C2=O)c(OC)c1] | $^1$H NMR (400 MHz, CDCl$_3$) 6.66-6.75 (m, 2H), 4.13-4.23 (m, 2H), 3.71 (d, 3H), 3.16-3.26 (m, 1H), 3.07-3.15 (m, 1H), 2.37 (d, 1H), 2.17 (m, 3H), 2.04 (s, 3H), 1.83 (m, 1H), 1.68-1.77 (m, 1H), 1.21-1.31 (m, 3H) |

TABLE P1-continued

Additional compounds in Table P1 below illustrate the present invention, and are preferred embodimens of the compounds of formula (I) according to the present invention.

| Compound Number | Structure | $^1$H NMR δ (delta) (CDCl$_3$ unless stated), or other physical data |
|---|---|---|
| P3 | 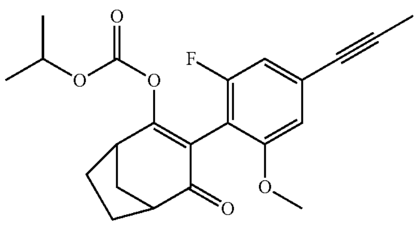 [SMILES: CC#Cc1cc(F)c(C2=C(OC(=O)OC(C)C)C3CCC(C3)C2=O)c(OC)c1] | $^1$H NMR (400 MHz, CDCl$_3$) 6.65-6.75 (m, 2H), 4.77-4.89 (m, 1H), 3.68-3.74 (m, 3H), 3.20 (d, 1H), 3.06-3.15 (m, 1H), 2.36 (d, 1H), 2.11-2.23 (m, 2H), 2.01-2.11 (m, 4H), 1.83 (m, 1H), 1.73 (m, 1H), 1.20-1.29 (m, 6H) |
| P4 | 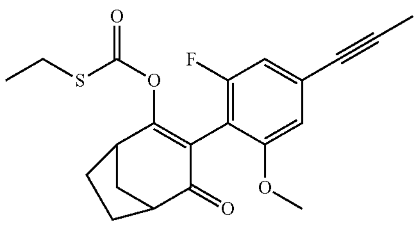 | $^1$H NMR (400 MHz, CDCl$_3$) 6.65-6.77 (m, 2H), 3.71 (d, 3H), 3.07-3.24 (m, 2H), 2.77-2.86 (m, 2H), 2.36 (m, 1H), 2.01-2.25 (m, 6H), 1.76-1.88 (m, 1H), 1.66-1.75 (m, 1H), 1.25 (m, 3H) |
| P5 | 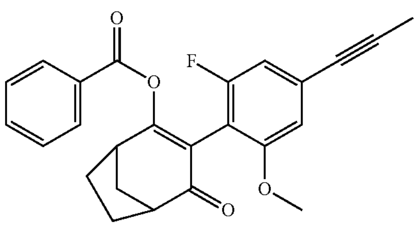 [SMILES: CC#Cc1cc(F)c(C2=C(OC(=O)c3ccccc3)C3CCC(C3)C2=O)c(OC)c1] | $^1$H NMR (400 MHz, CDCl$_3$) 7.82-7.88 (m, 2H), 7.57 (m, 1H), 7.36-7.44 (m, 2H), 6.55-6.74 (m, 2H), 3.55-3.68 (m, 3H), 3.26-3.41 (m, 1H), 3.13-3.20 (m, 1H), 2.33-2.51 (m, 1H), 2.06-2.27 (m, 3H), 2.01 (s, 3H), 1.82-1.94 (m, 1H), 1.72-1.81 (m, 1H) |

The compounds of the following Tables 1 to 6 are also particular and/or preferred embodiments of the compounds of formula (I) according to the present invention.

For the most part, these compounds can generally be prepared by method(s) similar to those disclosed in the Examples hereinabove and/or disclosed in the "Processes for preparation of compounds" section hereinabove using appropriate starting materials, and/or in an analogous manner.

Table 1 covers 28 compounds of the following formula

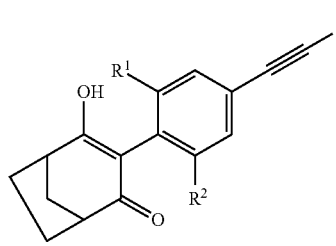

wherein X, R$^1$ and R$^2$ are as defined in Table 1.

TABLE 1

| Compound Number | R$^1$ | R$^2$ | X |
|---|---|---|---|
| 1.01 | fluorine | methoxy | methyl |
| 1.02 | fluorine | ethoxy | methyl |
| 1.03 | fluorine | trifluoromethoxy | methyl |
| 1.04 | fluorine | difluoromethoxy | methyl |
| 1.05 | fluorine | 2,2,2-trifluoroethoxy | methyl |
| 1.06 | fluorine | 2-methoxyethoxy | methyl |
| 1.07 | fluorine | ethynyl | methyl |
| 1.08 | fluorine | methoxy | chlorine |
| 1.09 | fluorine | ethoxy | chlorine |
| 1.10 | fluorine | trifluoromethoxy | chlorine |
| 1.11 | fluorine | difluoromethoxy | chlorine |
| 1.12 | fluorine | 2,2,2-trifluoroethoxy | chlorine |
| 1.13 | fluorine | 2-methoxyethoxy | chlorine |
| 1.14 | fluorine | ethynyl | chlorine |
| 1.15 | bromine | methoxy | methyl |
| 1.16 | bromine | ethoxy | methyl |
| 1.17 | bromine | trifluoromethoxy | methyl |
| 1.18 | bromine | difluoromethoxy | methyl |
| 1.19 | bromine | 2,2,2-trifluoroethoxy | methyl |
| 1.20 | bromine | 2-methoxyethoxy | methyl |
| 1.21 | bromine | ethynyl | methyl |
| 1.22 | bromine | methoxy | chlorine |
| 1.23 | bromine | ethoxy | chlorine |
| 1.24 | bromine | trifluoromethoxy | chlorine |
| 1.25 | bromine | difluoromethoxy | chlorine |
| 1.26 | bromine | 2,2,2-trifluoroethoxy | chlorine |
| 1.27 | bromine | 2-methoxyethoxy | chlorine |
| 1.28 | bromine | ethynyl | chlorine |

Table 2 covers 28 compounds of the following type

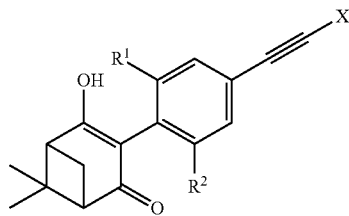

wherein $R^1$, $R^2$ and X are as defined in Table 1.

Table 3 covers 28 compounds of the following type

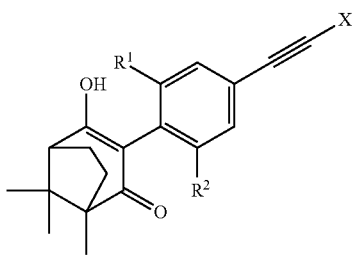

wherein $R^1$, $R^2$ and X are as defined in Table 1.

Table 4 covers 28 compounds of the following type

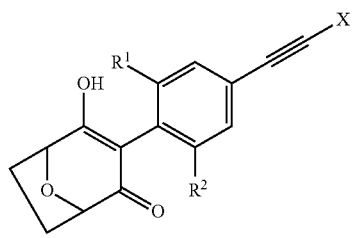

wherein $R^1$, $R^2$ and X are as defined in Table 1.

Table 5 covers 28 compounds of the following type

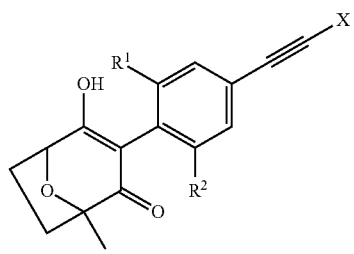

wherein $R^1$, $R^2$ and X are as defined in Table 1.

Table 6 covers 28 compounds of the following type

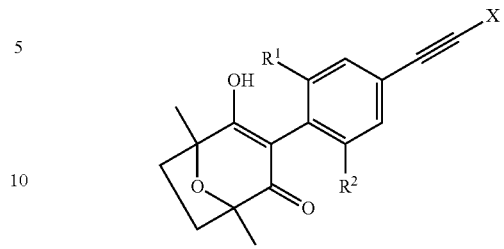

wherein $R^1$, $R^2$ and X are as defined in Table 1.

BIOLOGICAL EXAMPLES

Biological Example 1

Glasshouse Assay for Herbicidal Activity

Seeds of a variety of test plant species were sown in standard soil** in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient (the test herbicide) in acetone/water (50:50) solution containing 0.5% Tween 20 (polyoxyethylene sorbitan monolaurate, CAS Reg. No. 9005-64-5). The test plants were then grown on under controlled conditions in a glasshouse (at 24/16° C., day/night; 14 hours light; 65% humidity) and watered twice daily. 13 Days after application of the test herbicide, for pre- and post-emergence, the test was evaluated visually for percentage phytotoxicity to each plant (where 100%=total damage to plant; 0%=no damage to plant). Generally, each test herbicide is only tested on 1 plant per plant species for each application rate tested and for each application timing.

**The "standard soil" in Biological Example 1 is usually a "sand" or "sandy loam" type of soil.

Biological Example 1A

Post-Emergence Application—Herbicidal Activity Results (Percentage Phytotoxicity)

Test Weeds:

Dicotyledonous weeds: ABUTH=*Abutilon theophrasti*; AMARE=*Amaranthus retroflexus*. Grassy monocotyledonous weeds: SETFA=*Setaria faberi*; ALOMY=*Alopecurus myosuroides*; ECHCG=*Echinochloa crus-galli*; ZEAMX=*Zea mays* (corn, maize, e.g. volunteer corn).

| Compound No. | Application Rate (g/ha) | ABUTH | AMARE | SETFA | ALOMY | ECHCG | ZEAMX |
|---|---|---|---|---|---|---|---|
| A1 (test 1) | 250 | 80 | 30 | 100 | 100 | 100 | 100 |
| A1 (test 1) | 30 | 30 | 20 | 100 | 100 | 100 | 100 |
| A1 (test 1) | 8 | 0 | 0 | 80 | 80 | 100 | 100 |
| A1 (test 2)* | 250 | 20 | 30 | 90 | — | 100 | 100 |
| A1 (test 2)* | 30 | 0 | 0 | 70 | — | 90 | 90 |
| A1 (test 2)* | 8 | 0 | 0 | 50 | — | 70 | 80 |

-continued

| Compound No. | Application Rate (g/ha) | ABUTH | AMARE | SETFA | ALOMY | ECHCG | ZEAMX |
|---|---|---|---|---|---|---|---|
| A2 | 250 | 0 | 0 | 90 | 90 | 100 | 100 |
| A2 | 30 | 0 | 0 | 90 | 80 | 100 | 100 |
| A3 | 250 | 10 | 20 | 100 | 100 | 100 | 100 |
| A3 | 30 | 0 | 0 | 80 | 70 | 90 | 90 |
| A4 | 250 | 30 | 50 | 100 | 90 | 100 | 100 |
| A4 | 30 | 10 | 20 | 70 | 80 | 90 | 100 |
| A5 | 250 | 30 | 30 | 80 | 70 | 100 | 100 |
| A6 | 250 | 20 | 50 | 80 | 80 | 100 | 100 |
| A7 | 250 | 70 | 60 | 90 | 90 | 100 | 100 |
| A7 | 30 | 0 | 50 | 70 | 60 | 90 | 80 |
| A8 | 250 | 0 | 10 | 70 | 70 | 70 | 50 |
| A9 | 250 | 0 | 0 | 20 | 10 | 10 | 20 |
| A10 | 250 | 0 | 0 | 0 | 0 | 0 | 40 |
| P1 | 250 | 80 | 40 | 100 | 100 | 100 | 100 |
| P1 | 30 | 0 | 10 | 80 | 90 | 100 | 100 |
| P1 | 8 | 0 | 0 | 70 | 60 | 80 | 100 |
| P2 | 250 | 80 | 40 | 100 | 90 | 100 | 100 |
| P2 | 30 | 30 | 20 | 90 | 90 | 100 | 100 |
| P2 | 8 | 10 | 20 | 60 | 70 | 90 | 90 |
| P3 | 250 | 80 | 40 | 100 | 100 | 100 | 100 |
| P3 | 30 | 10 | 0 | 80 | 80 | 100 | 100 |
| P3 | 8 | 10 | 0 | 60 | 60 | 80 | 90 |
| P4 | 250 | 80 | 20 | 100 | 90 | 100 | 100 |
| P4 | 30 | 20 | 30 | 80 | 90 | 100 | 100 |
| P4 | 8 | 10 | 20 | 70 | 80 | 90 | 100 |
| P5 | 250 | 80 | 20 | 90 | 90 | 100 | 100 |
| P5 | 30 | 10 | 0 | 80 | 90 | 100 | 100 |
| P5 | 8 | 0 | 0 | 60 | 70 | 90 | 100 |
| B1 | 250 | 70 | 20 | 90 | 80 | 100 | 100 |
| B1 | 30 | 50 | 0 | 70 | 20 | 70 | 90 |
| B1 | 8 | 50 | 0 | 70 | 0 | 20 | 80 |

Note:
A [—] in the table above indicates that that compound was not tested on that plant.

*In test 2 on compound A1, the post-emergence herbicidal activity against LOLPE (*Lolium perenne*) was 100%, 90% and 60%, at 250, 30 and 8 g/ha respectively.

It can be seen that compound A1, having a 2-fluoro-6-methoxy-4-(prop-1-ynyl)-phenyl moiety, appears to be a more potent herbicide (in tests 1 and 2), versus the grassy monocotyledonous weeds ALOMY and ECHCG, than compound B1 which has a 2-fluoro-6-methoxy-4-ethynyl-phenyl moiety, when applied post-emergence at 30 and 8 g/ha under the conditions stated.

Biological Example 1B

Pre-Emergence Application—Herbicidal Activity Results (Percentage Phytotoxicity)

Test Weeds:
Dicotyledonous weeds: ABUTH=*Abutilon theophrasti*; AMARE=*Amaranthus retroflexus*. Grassy monocotyledonous weeds: SETFA=*Setaria faberi*; ALOMY=*Alopecurus myosuroides*; ECHCG=*Echinochloa crus-galli*; ZEAMX= *Zea mays* (corn, maize, e.g. volunteer corn).

| Compound No. | Application Rate (g/ha) | ABUTH | AMARE | SETFA | ALOMY | ECHCG | ZEAMX |
|---|---|---|---|---|---|---|---|
| A1 (test 1) | 250 | 20 | 20 | 100 | 100 | 100 | 100 |
| A1 (test 1) | 30 | 0 | 0 | 80 | 100 | 100 | 100 |
| A1 (test 1) | 8 | 0 | 0 | 50 | 70 | 100 | 60 |
| A1 (test 2)* | 250 | 0 | 30 | 80 | — | 100 | 100 |
| A1 (test 2)* | 30 | 0 | 0 | 40 | — | 30 | 90 |
| A1 (test 2)* | 8 | 0 | 0 | 40 | — | 30 | 70 |
| A2 | 250 | 60 | 40 | 100 | 90 | 100 | 100 |
| A2 | 30 | 60 | 10 | 70 | 70 | 90 | 60 |
| A3 | 250 | 10 | 20 | 100 | 100 | 100 | 100 |
| A4 | 250 | 30 | 50 | 70 | 90 | 100 | 100 |

-continued

| Compound No. | Application Rate (g/ha) | ABUTH | AMARE | SETFA | ALOMY | ECHCG | ZEAMX |
|---|---|---|---|---|---|---|---|
| A4 | 30 | 20 | 40 | 50 | 70 | 90 | 80 |
| A5 | 250 | 20 | 50 | 60 | 40 | 80 | 90 |
| A6 | 250 | 30 | 60 | 70 | 60 | 80 | 80 |
| A7 | 250 | 30 | 70 | 70 | 100 | 100 | 100 |
| A7 | 30 | 20 | 40 | 50 | 60 | 60 | 80 |
| A8 | 250 | 0 | 40 | 60 | 60 | 60 | 70 |
| A8 | 30 | 10 | 50 | 60 | 40 | 30 | 60 |
| P1 | 250 | 30 | 70 | 80 | 100 | 100 | 100 |
| P1 | 30 | 10 | 50 | 40 | 70 | 90 | 90 |
| P2 | 250 | 60 | 70 | 90 | 100 | 100 | 100 |
| P2 | 30 | 20 | 40 | 50 | 80 | 80 | 90 |
| P3 | 250 | 10 | 60 | 80 | 100 | 100 | 100 |
| P3 | 30 | 0 | 30 | 20 | 70 | 80 | 80 |
| P4 | 250 | 40 | 60 | 90 | 100 | 100 | 100 |
| P4 | 30 | 0 | 30 | 60 | 80 | 100 | 90 |
| P5 | 250 | 60 | 70 | 80 | 100 | 100 | 100 |
| P5 | 30 | 0 | 20 | 60 | 70 | 80 | 80 |
| B1 | 250 | 0 | 30 | 100 | 90 | 90 | 100 |
| B1 | 30 | 20 | 50 | 60 | 10 | 50 | 70 |
| B1 | 8 | 10 | 30 | 40 | 0 | 50 | 0 |

Note:
A [—] in the table above indicates that that compound was not tested on that plant.
*In test 2 on compound A1, the pre-emergence herbicidal activity against LOLPE (*Lolium perenne*) was 100%, 80% and 60%, at 250, 30 and 8 g/ha respectively.

It can be seen that compound A1, having a 2-fluoro-6-methoxy-4-(prop-1-ynyl)-phenyl moiety, appears to be a more potent herbicide (in tests 1 and 2), versus the grassy monocotyledonous weeds/plants ALOMY and ZEAMX, than compound B1 which has a 2-fluoro-6-methoxy-4-ethynyl-phenyl moiety, when applied pre-emergence at 30 and 8 g/ha under the conditions stated.

Biological Example 2

Glasshouse Assay for Herbicidal Activity

Seeds of a variety of monocotyledonous and dicotyledonous test plants are sown in standard soil in pots. The plants are cultivated for one day (for pre-emergence) or for about 12 days (range=10-13 days) (for post-emergence) under controlled conditions in a glasshouse (warm climate species at 24/18° C., cool climate species at 20/16° C., both at day/night; 16 hours light; 65% humidity).

An "instant formulation", known as the "IF50", containing 50 g/litre (i.e. 5% w/v) of the "technical" (i.e. unformulated) active ingredient is prepared by dissolving the active ingredient in a mixture of organic solvents and emulsifier, details of which are provided in the Table below. This IF50 is then mixed with a small, variable amount of acetone to aid dissolution, before addition of a 0.2% v/v aqueous solution of the adjuvant X-77 (which is a mixture of alkyl aryl polyoxyethylene glycols and free fatty acids in isopropanol, CAS Registry number 11097-66-8), as the aqueous diluent, to form an aqueous spray solution which contains a predetermined concentration of the active ingredient (which varies depending on the application rate of the active ingredient to the plants) and 0.2% v/v of the adjuvant X-77. This aqueous spray solution is then sprayed onto the plants, after one day's cultivation (for pre-emergence) or after about 12 days' cultivation (for post-emergence).

TABLE

Composition of the mixture of organic solvents and emulsifier to be used as a base for the instant formulation (IF50).

| Component | Supplier | Chemical description | CAS Registry number | Amount/ % w/w |
|---|---|---|---|---|
| Emulsogen EL360 ™ | Clariant | castor oil ethoxylate (as emulsifier) | 61791-12-6 | 11.12 |
| N-methyl-pyrrolidone | widely available | 1-methyl-2-pyrrolidone | 872-50-4 | 44.44 |
| Dowanol DPM ™ glycol ether | Dow | dipropylene glycol monomethyl ether | 34590-94-8 | 44.44 |

The test plants are then grown on, in a glasshouse (greenhouse) under controlled conditions (at either 24/18° C. or 20/16° C. (day/night) as mentioned above; 16 hours light; 65% humidity) and are watered twice daily. Either 14 or 15 days after application of the herbicide (14 or 15 DAA) (for post-emergence), or 20 days after application of the herbicide (20 DAA) (for pre-emergence), the test plants are evaluated visually, and an assessed percentage phytotoxicity score is given for each herbicidal application on each plant species (where 100%=total damage to plant; 0%=no damage to plant).

Some of the typical test plants are as follows:

Cool climate crop plants: *Triticum aestivum* (TRZAW, winter wheat), *Brassica napus* (BRSNN, rape, also called oilseed rape or rapeseed), *Beta vulgaris* (BEAVA, sugarbeet).

Warm climate crop plants: *Glycine max* (GLXMA, soybean).

Cool climate ("cool season") grassy monocotyledonous weeds: *Alopecurus myosuroides* (ALOMY), *Avena fatua* (AVEFA), *Lolium perenne* (LOLPE), *Poa annua* (POAAN), *Bromus tectorum* (BROTE).

Warm climate ("warm season") grassy monocotyledonous weeds: *Setaria faberi* (SETFA), SORVU (*Sorghum bicolor* (L.) *Moench* ssp. Bicolor, or *Sorghum vulgare* Pers.), *Digitaria sanguinalis* (DIGSA), *Echinochloa crus-galli* (ECHCG), *Brachiaria plantaginea* (BRAPL); *Zea mays* (ZEAMX, corn, maize, e.g. volunteer corn).

Biological Example 2

Post-Emergence Herbicidal Activity Results

| Compound Number | Appl. Rate (g/ha) | TRZAW | ZEAMX | GLXMA | BRSNN | BEAVA | ALOMY | AVEFA | LOLPE | SETFA | SORVU | DIGSA | ECHCG | BRAPL |
|---|---|---|---|---|---|---|---|---|---|---|---|---|---|---|
| A1 (test 1) | 250 g/ha | 100 | 100 | 60 | 80 | 30 | 100 | 100 | 100 | 100 | 100 | 100 | 100 | — |
| A1 * (test 1) | 30 g/ha | 80 | 100 | 20 | 40 | 10 | 90 | 80 | 80 | 70 | 100 | 100 | 100 | — |
| A1 (test 2) | 250 g/ha | 90 | 100 | 10 | 80 | 20 | 90 | 100 | 100 | 100 | 100 | 100 | 100 | 100 |
| A1 * (test 2) | 30 g/ha | 70 | 90 | 0 | 40 | 0 | 80 | 90 | 90 | 90 | 90 | 100 | 100 | 90 |
| A2 | 250 g/ha | 0 | 90 | 20 | 10 | 0 | 60 | 0 | 0 | 80 | 90 | 80 | 90 | — |
| A7 | 250 g/ha | 70 | 100 | 20 | 60 | 10 | 70 | 40 | 40 | 90 | 100 | 100 | 100 | 100 |
| A7 | 125 g/ha | 70 | 90 | 20 | 50 | 0 | 70 | 30 | 30 | 90 | 90 | 100 | 100 | 100 |
| A7 | 30 g/ha | 30 | 80 | 20 | 30 | 0 | 30 | 10 | 0 | 60 | 50 | 90 | 90 | 90 |
| P1 | 250 g/ha | 90 | 100 | 20 | 80 | 0 | 90 | 90 | 100 | 90 | 100 | 100 | 100 | 90 |
| P1 * | 30 g/ha | 60 | 100 | 0 | 10 | 0 | 80 | 80 | 100 | 80 | 100 | 90 | 100 | 100 |
| P3 | 250 g/ha | 90 | 100 | 0 | 80 | 0 | 90 | 90 | 100 | 100 | 100 | 100 | 100 | 100 |
| P3 * | 30 g/ha | 80 | 100 | 0 | 10 | 0 | 70 | 90 | 90 | 100 | 100 | 100 | 100 | 100 |
| P4 | 250 g/ha | 100 | 100 | 20 | 80 | 0 | 100 | 100 | 100 | 100 | 100 | 100 | 100 | 100 |
| P4 * | 30 g/ha | 80 | 100 | 10 | 50 | 0 | 80 | 90 | 90 | 90 | 100 | 80 | 90 | 100 |
| P5 | 250 g/ha | - | 100 | 0 | 80 | 0 | 90 | 90 | 100 | 90 | 100 | 100 | 100 | 100 |
| P5 * | 30 g/ha | 50 | 90 | 0 | 50 | 0 | 70 | 80 | 80 | 80 | 80 | 100 | 100 | 90 |
| X9 (Ref.) | 30 g/ha | 0 | — | 0 | 0 | — | 0 | 0 | 0 | 70 | — | 30 | 20 | 70 |
| X10 (Ref.) (test 1) | 30 g/ha | 0 | — | 0 | 0 | — | 80 | 30 | 70 | 100 | —*** | 100 | 50 | 80 |
| X10 ** (Ref.) (test 2) | 30 g/ha | 30 | 80 | 0 | 0 | 0 | 70 | 80 | 70 | 90 | 60 | 90 | 90 | 90 |

| Compound Number | Appl. Rate (g/ha) | TRZAW | ZEAMX | GLXMA | BRSNN | BEAVA | ALOMY | AVEFA | LOLPE | SETFA | SORVU | DIGSA | ECHCG | BRAPL |
|---|---|---|---|---|---|---|---|---|---|---|---|---|---|---|
| Compound Number | Appl. Rate (g/ha) | TRZAW | ZEAMX | GLXMA | BRSNN | BEAVA | ALOMY | AVEFA | LOLPE | SETFA | SORVU | DIGSA | ECHCG | BRAPL |

Note 1:
A [—] in the table above indicates that that compound was not tested on that plant.

Note 2:
Extra data from Biological Example 2 is shown in *, , and * below:
* Compounds A1 (test 1), A1 (test 2), P1, P3, P4 and P5 of the invention showed phytotoxicity versus *Poa annua* (POAAN) of 70%, 70%, 80%, 80%, 90% and 80% respectively, when applied post-emergence at 30 g/ha. Compounds A1 (test 1), A1 (test 2), P1, P3, P4 and P5 of the invention showed phytotoxicity versus *Bromus tectorum* (BROTE) of 70%, 70%, 70%, 70%, 90% and 50% respectively, when applied post-emergence at 30 g/ha.
** Reference (Comparator) Compound X10 (test 2) showed 0% phytotoxicity versus *Poa annua* (POAAN) and 40% phytotoxicity versus *Bromus tectorum* (BROTE), when applied post-emergence at 30 g/ha.
*** Reference (Comparator) Compound X10 (test 1) showed 70% phytotoxicity versus an unidentified *Sorghum* species when applied post-emergence at 30 g/ha.

Note 3:
Reference compound X9 is

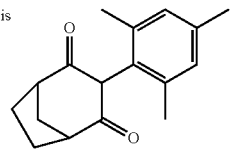

Note 4:
Reference (Comparator) compound X10 is

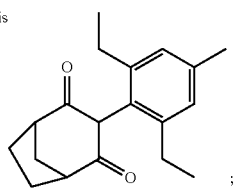

this is compound 21.115 disclosed on page 105 of WO 01/17972 A2.

Note 5:
The herbicidal activity data (e.g. post-emergence) shown above in Biological Example 2 for Reference/Comparator compounds X9 and X10 (test 1) is thought likely to have been measured some years ago (ca. 2003), probably using a variant of the above-described test method. Also, for the post-emergence activity of X9 and X10 (test 1), it is not currently known exactly how many days after application of the herbicide the phytotoxicity on the plants was measured. Therefore, for Reference Compound X10, the data for X10 (test 2) (done ca. 2014 at the same time as that of Compound A1, test 2) is likely to be more comparable to the data in Biological Example 2 for the compounds of the present invention, in particular Compound A1, than the data for X10 (test 1).

From the results shown above in Biological Example 2, Compound A1

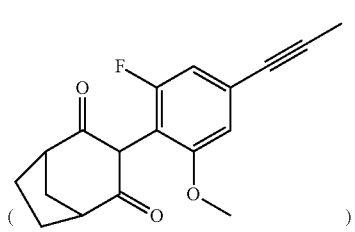 [SMILES: CC#Cc1cc(F)c(C2C(=O)C3CCC(C3)C2=O)c(OC)c1]

of the present invention appears to have higher post-emergence activities at 30 g/ha against the grassy monocotyledonous weeds *Lolium perenne* (LOLPE), *Poa annua* (POAAN), *Bromus tectorum* (BROTE) and SORVU (*Sorghum bicolor* (L.) Moench ssp. Bicolor, or *Sorghum vulgare* Pers.), than those of Reference (Comparator) compound X10 disclosed as compound 21.115 in WO 01/17972 A2.

Biological Example 3

Assay for Biological Example 3—Glasshouse Assay for Herbicidal Activity, Using Various Adjuvant Systems Materials and Methods
Herbicide Application: Post-emergence foliar spray application, 200 L/ha, usually one or two replicates for the weeds (depending on application rate), and two replicates for soybean.

Climate: Standard warm conditions (tropical), in glasshouse. Specifically, the glasshouse bay conditions are 24° C./18° C. day/night; 16/8 hours light/dark; 65% humidity.

Plants: The herbicidal application takes place at the following growth stages for plants which include inter alia one or more of the following plants (usually the herbicidal application takes place on at least the following plants: DIGSA, ELEIN, SETFA, ZEAMX, GLXMA Nikko, and GLXMA TMG133, and often also either BRADC or BRAPP):

*Brachiaria decumbens* (BRADC)—growth stage (GS) 12 or 13 (or GS 12)—or, if BRADC is not used, then usually *Brachiaria platyphylla* (BRAPP)—growth stage 12 or 13
*Digitaria sanguinalis* (DIGSA)—growth stage 12 or 13
*Eleusine indica* (ELEIN)—growth stage 12 or 13
*Setaria faberi* (SETFA)—growth stage 12 or 13
*Echinochloa crus-galli* (ECHCG)—growth stage 12 or 13
*Sorghum halepense* (annual) (SORHA)—growth stage 12 or 13
*Panicum dichotomiflorum* (PANDI)—growth stage 12 or 13
*Zea mays* (ZEAMX, maize/corn, e.g. can occur as volunteer corn) cultivar "Garland"—growth stage 12 or 13
*Glycine max* (GLXMA, soybean) cultivar "Nikko"—growth stage: $1^{st}$ trifoliate
*Glycine max* (GLXMA, soybean) cultivar "TMG133"—which is Roundup Ready™ glyphosate-tolerant soybean cultivar TMG133 (typically available from Monsanto in Brazil)—growth stage: 1$^{st}$ trifoliate.

Herbicidal Compositions Tested:

Each test compound is applied with one of the following adjuvant systems (all percentages are final concentrations in the aqueous spray mixture):

Adjuvant system 1: 0.5% v/v Adigor™*, 1.0% v/v AMS (ammonium sulphate) and 12.5% v/v IPA (isopropyl alcohol).

Adjuvant system 2: 0.5% v/v Hexamoll™ DINCH**, 1.0% v/v AMS (ammonium sulphate) and 12.5% v/v IPA (isopropyl alcohol).

Adjuvant system 3: 0.5% v/v tris-(2-ethylhexyl)phosphate ("TEHP"), 1.0% v/v AMS (ammonium sulphate) and 12.5% v/v IPA (isopropyl alcohol).

***Adigor™ (currently available in many countries from Syngenta) is an emulsifiable concentrate which consists of:
(i) ethoxylated alcohols, which typically includes ethoxylated higher alcohols (e.g. ethoxylates of alcohols wherein the alcohols are within the range of $C_{12}$-$C_{22}$); and
(ii) a mixture of heavy aromatic hydrocarbons, which typically includes (e.g. includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and
(iii) about 47% w/w and/or about 45% w/v (with respect to the emulsifiable concentrate) of methylated rapeseed oil (rapeseed oil methyl ester) (e.g. Agnique ME 18 RD-F™), as an adjuvant.

**Hexamoll™ DINCH™ is 1,2-cyclohexane dicarboxylic acid di-isononyl ester

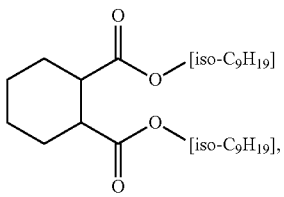

CAS Registry no. 166412-78-8), and is usually available from BASF. "Isononyl" in this context is thought to mean a mixture of two or more branched isomers of $C_9H_{19}$.

Method:

Seeds of the weed (including volunteer) plants, typically including inter alia Digitaria sanguinalis (DIGSA), Eleusine indica (ELEIN), Setaria faberi (SETFA), Zea mays (ZEAMX, corn), and sometimes also [either Brachiaria decumbens (BRADC) or Brachiaria platyphylla (BRAPP)], are sown in seed trays (troughs) containing clay loam soil (pH 7.0, 2.2% organic matter, "Trough Mix A"); and soybean seed is sown in pots containing the same soil with 3 soybean seedlings per pot. The plants are sprayed with the test herbicide when they reach the growth stages mentioned above.

The test herbicidal solutions are prepared by mixing the appropriate aliquots of the test substance(s) and one of the adjuvant systems indicated above*** in deionised water to give the desired treatment concentration.

The herbicidal application is made as a foliar spray, using a tracksprayer. Following the herbicidal application, the plants are watered twice per day for the duration of the test. A visual assessment of the % herbicidal damage is made 7 and 14 Days After herbicide Application (DAA) (or, in a minority of cases, 7 and 15 DAA), and the results are recorded as % visual herbicidal damage where 0%=no damage to plants and 100%=plant totally killed.

***Adjuvant system=either Adigor™ or Hexamoll DINCH™ or tris-(2-ethylhexyl)phosphate at 0.5% v/v, and 12.5% v/v IPA (isopropyl alcohol), and 1.0% v/v AMS (ammonium sulphate); all percentages are final concentrations in the aqueous spray mixture.

Biological Example 3

Post-Emergence Activity—Results at 14 or 15 Days after Herbicide Application

Compounds A1, A3, A4, A5, A6, A7, A8, P1, P2 and P4, which are compounds of formula (I) according to the present invention, were tested in a test method substantially as described above.

Compounds A3, A4, A5, A6 and A7 were tested using the 0.5% v/v tris-(2-ethylhexyl)phosphate+1.0% v/v AMS+12.5% v/v IPA adjuvant system. Compounds A8, P1, P2 and P4 were tested using the 0.5% v/v Adigor™+1.0% v/v AMS+12.5% v/v IPA adjuvant system. Compound A1 was tested using the 0.5% v/v Hexamol Dinch™+1.0% v/v AMS+12.5% v/v IPA adjuvant system.

The percentages of herbicidal damage/plant control, at 14 Days After herbicide Application (DAA) (or, in a minority of cases, at 15 DAA), for the Compounds tested and for some of the plants tested, were in the following percentage ranges.

Control of Brachiaria decumbens (BRADC), a Warm-climate (Warm-season) Grassy Weed At 14 DAA, certain test compounds (Compound A1 or A7) showed percentage control of (percentage phytotoxicities on) Brachiaria decumbens (BRADC) in the range of from 90% to 97%, when applied post-emergence at an application rate of 8g/ha.

At 14 or 15 DAA, certain test compounds (Compound P1, P2 or P4) showed percentage control of Brachiaria decumbens (BRADC) in the range of from 70% to 80%, when applied post-emergence at an application rate of 8g/ha.

At 14 DAA, Compound A8 showed percentage control of Brachiaria decumbens (BRADC) of 15%, when applied post-emergence at an application rate of 8g/ha.

Control of Digitaria sanguinalis (DIGSA), a Warm-climate (Warm-season) Grassy Weed At 14 or 15 DAA, certain test compounds (Compound A1, A3, A4, A7, P2 or P4) showed percentage control of (percentage phytotoxicities on) Digitaria sanguinalis (DIGSA) in the range of from 85% to 98%, when applied post-emergence at an application rate of 8g/ha.

At 14 or 15 DAA, Compound P1 showed a percentage control of Digitaria sanguinalis (DIGSA) of 70%, when applied post-emergence at an application rate of 8g/ha.

At 14 DAA, Compound A8 showed a percentage control of Digitaria sanguinalis (DIGSA) of 30%, when applied post-emergence at an application rate of 8g/ha.

At 14 or 15 DAA, Compound A6 showed a percentage control of Digitaria sanguinalis (DIGSA) of 5%, when applied post-emergence at an application rate of 8g/ha.

At 14 or 15 DAA, Compound A5 showed a percentage control of Digitaria sanguinalis (DIGSA) of 0%, when applied post-emergence at an application rate of 8g/ha.

Control of Eleusine indica (ELEIN), a Warm-climate (Warm-season) Grassy Weed

At 14 or 15 DAA, certain test compounds (Compound A1, A7, P2 or P4) showed percentage control of (percentage phytotoxicities on) Eleusine indica (ELEIN) in the range of from 90% to 98%, when applied post-emergence at an application rate of 8g/ha.

At 14 or 15 DAA, certain test compounds (Compound A4 or P1) showed percentage control of *Eleusine indica* (ELEIN) in the range of from 75% to 85%, when applied post-emergence at an application rate of 8g/ha.

At 15 DAA, Compound A3 showed a percentage control of *Eleusine indica* (ELEIN) of 55%, when applied post-emergence at an application rate of 8g/ha.

At 14 or 15 DAA, certain test compounds (Compound A6 or A8) showed percentage control of *Eleusine indica* (ELEIN) of 5%, when applied post-emergence at an application rate of 8g/ha.

At 14 or 15 DAA, Compound A5 showed a percentage control of *Eleusine indica* (ELEIN) of 0%, when applied post-emergence at an application rate of 8g/ha.

Control of *Setaria faberi* (SETFA), a Warm-climate (Warm-season) Grassy Weed

At 14 or 15 DAA, certain test compounds (Compound A1, A3, A4 or A7) showed percentage control of (percentage phytotoxicities on) *Setaria faberi* (SETFA) in the range of from 85% to 90%, when applied post-emergence at an application rate of 8g/ha.

At 14 or 15 DAA, certain test compounds (Compound P1, P2 or P4) showed percentage control of *Setaria faberi* (SETFA) in the range of from 65% to 75%, when applied post-emergence at an application rate of 8g/ha.

At 14 or 15 DAA, certain test compounds (Compound A5 or A6) showed percentage control of *Setaria faberi* (SETFA) of 25%, when applied post-emergence at an application rate of 8g/ha.

At 14 DAA, Compound A8 showed a percentage control of *Setaria faberi* (SETFA) of 10%, when applied post-emergence at an application rate of 8g/ha.

Control of *Zea mays* (ZEAMX, Corn), a Warm-climate (Warm-season) Grassy Plant

*Zea mays* (ZEAMX, maize/corn) is often present as a "volunteer" weed ("volunteer" corn) in fields where it was planted as a crop in preceding growing season(s) and where the present field crop is not corn.

At 14 or 15 DAA, certain test compounds (Compound A1, A3, A4, A7, P1, P2 or P4) showed a percentage control of (percentage phytotoxicities on) *Zea mays* (ZEAMX, corn) in the range of from 90% to 100%, when applied post-emergence at an application rate of 8g/ha.

At 14 or 15 DAA, certain test compounds (Compound A5 or A8) showed a percentage control of *Zea mays* (ZEAMX, corn) in the range of from 15% to 30%, when applied post-emergence at an application rate of 8g/ha.

At 14 or 15 DAA, Compound A6 showed a percentage control of *Zea mays* (ZEAMX, corn) of 0%, when applied post-emergence at an application rate of 8g/ha.

Phytotoxicity on *Glycine max* (GLXMA, Soybean) Cultivar "Nikko"

At 14 or 15 DAA, the test compounds (Compound A1, A3, A4, A5, A6, A7, A8, P1, P2 or P4) showed percentage phytotoxicities on *Glycine max* (GLXMA, soybean) cultivar "Nikko" in the range of from 2% to 15%, when applied post-emergence at an application rate of 120g/ha.

Phytotoxicity on *Glycine max* (GLXMA, Soybean) Cultivar "TMG133"

*Glycine max* (GLXMA, soybean) cultivar "TMG133" is Roundup Ready™ glyphosate-tolerant soybean cultivar TMG133, and is typically available from Monsanto in Brazil.

At 14 or 15 DAA, the test compounds (Compound A1, A3, A4, A5, A6, A7, A8, P1, P2 or P4) showed percentage phytotoxicities on *Glycine max* (GLXMA, soybean) cultivar "TMG133" in the range of from 1% to 10%, when applied post-emergence at an application rate of 120g/ha.

The invention claimed is:
1. A compound of formula (I)

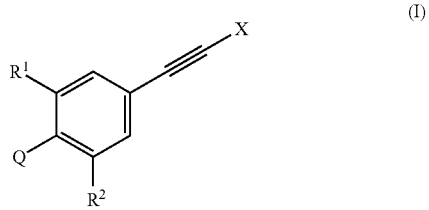

wherein:

X is methyl or chlorine;

$R^1$ is fluorine or bromine;

$R^2$ is ethynyl, $C_1$-$C_3$alkoxy-, $C_1$-$C_3$haloalkoxy-, or $C_1$-$C_3$alkoxy-$C_1$-$C_3$alkoxy-; and Q is a group of formula Q2:

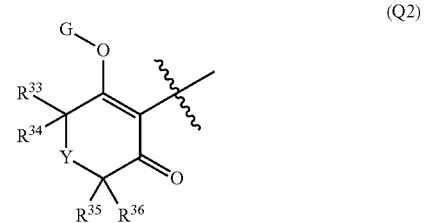

wherein in Q2:

$R^{33}$ and $R^{36}$, independently of each other, are hydrogen, $C_1$-$C_5$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl, $C_3$-$C_4$cycloalkyl, or an unsubstituted 4, 5 or 6 membered monocyclic heterocyclyl having one ring heteroatom independently selected from oxygen, sulfur and nitrogen, said heterocyclyl being attached at a ring carbon atom within the heterocyclyl;

provided that no more than one of $R^{33}$ and $R^{36}$ is alkenyl, alkynyl, alkoxyalkyl, alkylthioalkyl, alkylsulfinylalkyl, alkylsulfonylalkyl, cycloalkyl or heterocyclyl; and $R^{34}$ and $R^{35}$ taken together are —$(CH_2)_{n34}$— or —$(CH_2)_{n35}$—$C(R^{37a})(R^{37b})$—$(CH_2)_{n36}$—;

wherein $R^{37a}$ is $C_1$-$C_2$alkyl; $R^{37b}$ is hydrogen or $C_1$-$C_2$alkyl;

n34 is 1, 2 or 3; and n35 and n36 are independently 0, 1 or 2 provided that n35+n36 is 0, 1 or 2; and Y is O, S, S(O), S(O)$_2$, N($C_1$-$C_2$alkyl), N($C_1$-$C_2$alkoxy), C(O), $CR^{38}R^{39}$ or —$CR^{310}R^{311}CR^{312}R^{313}$—; and $R^{38}$ and $R^{39}$ are, independently of each other: hydrogen, $C_1$-$C_6$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl; $C_3$-$C_6$cycloalkyl or $C_3$-$C_6$cycloalkyl substituted by one or two substituents which independently are $C_1$-$C_3$alkyl or $C_1$-$C_2$fluoroalkyl, and in which one ring $CH_2$ moiety of a $C_4$-$C_6$cycloalkyl is optionally replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; $C_3$-$C_6$cycloalkyl substituted by one substituent being $C_1$-$C_3$alkoxy and optionally further substituted by one substituent being $C_1$-$C_2$alkyl; $C_5$-$C_6$cycloalkenyl or $C_5$-$C_6$cycloalkenyl substituted by one or two $C_1$-$C_3$alkyl substituents; $C_3$-$C_6$cycloalkyl$C_1$-$C_2$alkyl- or $C_3$-$C_6$cycloalkyl$C_1$-$C_2$alkyl- substituted by one or two ring substituents which independently are $C_1$-$C_3$alkyl or $C_1$-$C_2$fluoroalkyl, and in which one ring $CH_2$ moiety of a $C_4$-$C_6$cycloalkyl$C_1$-$C_2$alkyl- is optionally replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; $C_3$-$C_6$cycloalkyl$C_1$-$C_2$alkyl- substituted by one ring substituent being $C_1$-$C_3$alkoxy and optionally further substituted by one ring substituent being $C_1$-$C_2$alkyl; or HetA or HetA-$CH_2$—;

wherein HetA is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, —C(O)—N($R^{6H}$)($R^{6J}$), S$R^{6E}$, S(O)$R^{6E}$, —S(O)$_2$—$R^{6E}$, —N($R^{6F}$)($R^{6G}$), hydroxy, $C_2$-$C_3$alkenyl, —C($R^{6BB}$)=C($R^{6C1}$)($R^{6C2}$), $C_2$-$C_3$alkynyl, —C≡C—$R^{6AA}$, $C_1$-$C_3$alkoxy, $C_1$-$C_2$fluoroalkoxy, cyclopropyloxy, $CH_2$=CH—$CH_2$—O—, HC≡C—$CH_2$—O—, halogen, cyano or nitro; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;

provided that no more than one of $R^{38}$ and $R^{39}$ is an optionally substituted cycloalkyl, an optionally substituted cycloalkyl in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl, an optionally substituted cycloalkyl-alkyl-, an optionally substituted cycloalkyl-alkyl- in which one ring $CH_2$ moiety has been replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety, or HetA or HetA-$CH_2$—;

or $R^{38}$ is hydrogen or $C_1$-$C_2$alkyl, and $R^{39}$ is $C_1$-$C_2$alkoxy;

or $R^{38}$ and $R^{39}$ taken together are —$(CH_2)_{n37}$— or —$(CH_2)_{n38}$—$X^{32}$—$(CH_2)_{n39}$—;

wherein $X^{32}$ is O, S, S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl], N($C_1$-$C_2$alkoxy), C(H)($C_1$-$C_3$alkyl), C($C_1$-$C_2$alkyl)$_2$ or C(H)($C_1$-$C_3$alkoxy);

n37 is 2, 3, 4, 5 or 6; and n38 and n39 are independently 0, 1, 2 or 3 provided that n38+n39 is 2, 3, 4 or 5; and $R^{310}$, $R^{311}$, $R^{312}$ and $R^{313}$ are independently of each other hydrogen or $C_1$-$C_4$alkyl provided that no more than one of $R^{310}$, $R^{311}$, $R^{312}$ and $R^{313}$ is $C_3$-$C_4$alkyl;

and wherein:

$R^{6AA}$ is $C_1$fluoroalkyl, fluorine, chlorine or bromine;

$R^{6BB}$, $R^{6C1}$ and $R^{6C2}$ independently are hydrogen, methyl, $C_1$fluoroalkyl, fluorine or chlorine; provided that $R^{6BB}$, $R^{6C1}$ and $R^{6C2}$ in total contain no more than one carbon atom, and $R^{6BB}$, $R^{6C1}$ and $R^{6C2}$ in total comprise no more than one chlorine; and provided that —C($R^{6BB}$)=C($R^{6C1}$)($R^{6C2}$) is not $C_2$-$C_3$alkenyl;

$R^{6E}$ is $C_1$-$C_3$alkyl, $C_1$fluoroalkyl, or —N($R^{6H}$)($R^{6J}$);

$R^{6F}$ is —C(O)—$C_1$-$C_2$alkyl, —C(O)—$C_1$fluoroalkyl, —S(O)$_2$—$C_1$-$C_2$alkyl, —S(O)$_2$—$C_1$fluoroalkyl, $C_1$-$C_2$alkyl, or $C_1$fluoroalkyl;

$R^{6G}$ and $R^{6J}$ independently are hydrogen, methyl or $C_1$fluoroalkyl;

$R^{6H}$ is hydrogen, $C_1$-$C_2$alkyl, or $C_1$fluoroalkyl;

and wherein:

G is hydrogen, an agriculturally acceptable metal, or an agriculturally acceptable sulfonium or ammonium group; or G is —C($X^a$)—$R^a$, —C($X^b$)—$X^c$—$R^b$, —C($X^d$)—N($R^c$)—$R^d$, —SO$_2$—$R^e$, —P($X^e$)($R^f$)—$R^g$, —$CH_2$—$X^f$—$R^h$; or phenyl-$CH_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_6$alkoxy-C(O)—CH=CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-;

$X^a$, $X^b$, $X^c$, $X^d$, $X^e$ and $X^f$ are independently of each other oxygen or sulfur;

$R^a$ is H, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, form an unsubstituted 4, 5, 6 or 7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

and wherein "heteroaryl" means an aromatic ring system containing at least one ring heteroatom and consisting either of a single ring or of two fused rings;

and wherein the compound of formula (I) is optionally present as an agrochemically acceptable salt thereof.

2. A compound according to claim 1 wherein X is methyl.

3. A compound according to claim 1 wherein $R^1$ is fluorine.

4. A compound according to claim 1, wherein $R^1$ is bromine.

5. A compound according to claim 1 wherein $R^2$ is —O—$R^{2A}$, and wherein $R^{2A}$ is methyl, ethyl, trifluoromethyl, difluoromethyl, trifluoroethyl, or —$CH_2CH_2OCH_3$.

6. A compound according to claim 1 wherein $R^2$ is —O—$R^{2A}$, and wherein $R^{2A}$ is methyl, ethyl, trifluoromethyl or difluoromethyl.

7. A compound according to claim 6, wherein $R^1$ is fluorine and X is methyl.

8. A compound according to claim 1 wherein $R^2$ is —O—$R^{2A}$, and wherein $R^{2A}$ is methyl.

9. A compound according to claim 1, wherein G is hydrogen; an agriculturally acceptable metal, or an agriculturally acceptable sulfonium or ammonium group; or G is —C($X^a$)—$R^a$ or —C($X^b$)—$X^c$—$R^b$.

10. A compound according to claim 9, wherein:

$X^a$ and $X^b$ are oxygen, and $X^c$ is oxygen or sulfur;

$R^a$ is $C_1$-$C_{10}$alkyl, $C_2$-$C_6$alkenyl, $C_2$-$C_6$alkynyl, $C_3$-$C_6$cycloalkyl, $C_1$-$C_4$alkoxy$C_1$-$C_4$alkyl, $C_3$-$C_7$cycloalkyl$C_1$alkyl; or phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, or cyano; and $R^b$ is $C_1$-$C_{10}$alkyl, $C_2$-$C_5$alkenyl-$CH_2$—, $C_2$-$C_4$alkenyl-CH(Me)-, $C_2$-$C_5$alkynyl-$CH_2$—, $C_2$-$C_4$alkynyl-CH(Me)-, $C_3$-$C_6$cycloalkyl, $C_1$-$C_4$alkoxy$C_1$-$C_4$alkyl, $C_3$-$C_7$cycloalkyl$C_1$alkyl; or phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, or cyano.

11. A compound according to claim 1, wherein $R^{33}$ and $R^{36}$, independently of each other, are hydrogen, $C_1$-$C_3$alkyl or $C_1$-$C_2$alkoxy$C_1$-$C_2$alkyl; provided that no more than one of $R^{33}$ and $R^{36}$ is alkoxyalkyl;

and $R^{34}$ and $R^{35}$ taken together are —$(CH_2)_{n34}$— or —$(CH_2)_{n35}$—$C(R^{37a})(R^{37b})$—$(CH_2)_{n36}$—;
wherein $R^{37a}$ is $C_1$-$C_2$alkyl; $R^{37b}$ is hydrogen or $C_1$-$C_2$alkyl;
n34 is 2 or 3; and
n35 and n36 are independently 0, 1 or 2 provided that n35+n36 is 1 or 2.

12. The compound according to claim 1, wherein
$R^{33}$ and $R^{36}$, independently of each other, are hydrogen or $C_1$-$C_2$alkyl; and
$R^{34}$ and $R^{35}$ taken together are —$(CH_2)_{n34}$— wherein n34 is 2 or 3.

13. The compound according to claim 1, wherein
$R^{38}$ and $R^{39}$, independently of each other, are hydrogen or $C_1$-$C_3$alkyl.

14. A compound according to claim 1, wherein Y is O or $CR^{38}R^{39}$.

15. A compound according to claim 1, wherein
Y is $CR^{38}R^{39}$; and
$R^{34}$ and $R^{35}$ taken together are —$(CH_2)_{n34}$— or —$(CH_2)_{n35}$—$C(R^{37a})(R^{37b})$—$(CH_2)_{n36}$—;
wherein $R^{37a}$ is $C_1$-$C_2$alkyl; $R^{37b}$ is hydrogen or $C_1$-$C_2$alkyl;
n34 is 2 or 3; and
n35 and n36 are independently 0, 1 or 2 provided that n35+n36 is 1 or 2.

16. A compound according to claim 15, wherein
$R^{33}$ and $R^{36}$, independently of each other, are hydrogen or $C_1$-$C_2$alkyl; and
$R^{34}$ and $R^{35}$ taken together are —$(CH_2)_{n34}$— wherein n34 is 2 or 3.

17. A compound according to claim 1, wherein Y is $CH_2$.

18. A compound according to claim 1 wherein:
$R^1$ is fluorine,
X is methyl,
$R^2$ is $OR^{2A}$, wherein $R^{2A}$ is selected from methyl, ethyl and difluoromethyl,
and Q is Q2 wherein:
Y is $CR^{38}R^{39}$, and $R^{38}$ and $R^{39}$ are each independently hydrogen or methyl, and
$R^{34}$ and $R^{35}$ taken together are —$(CH_2)_{n34}$—or —$(CH_2)_{n35}$—$C(R^{37a})(R^{37b})$—$(CH_2)_{n36}$.

19. A compound according to claim 1, which is compound A1, A2, A3, A4, A5, A6, A7, A8, P1, P2, P3, P4 or P5:

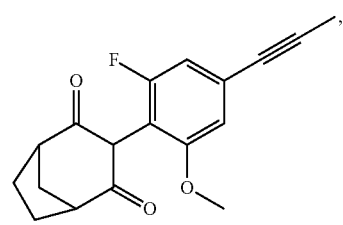

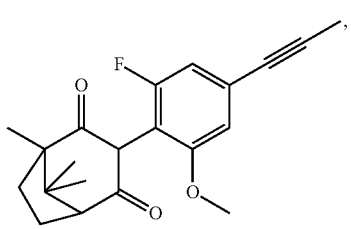

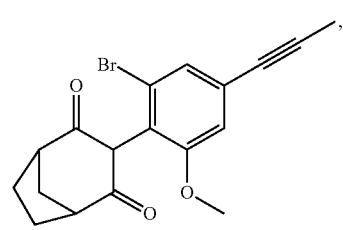

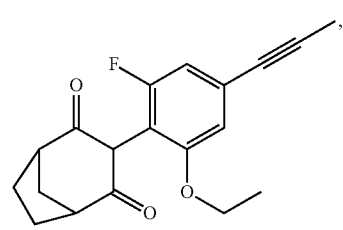

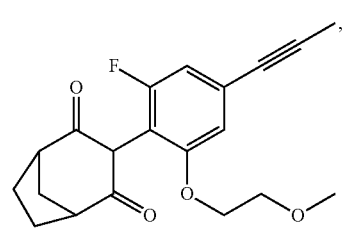

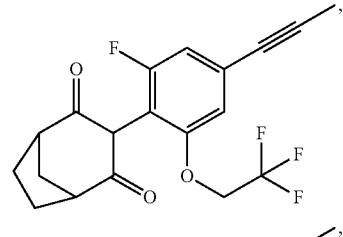

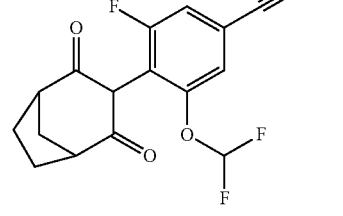

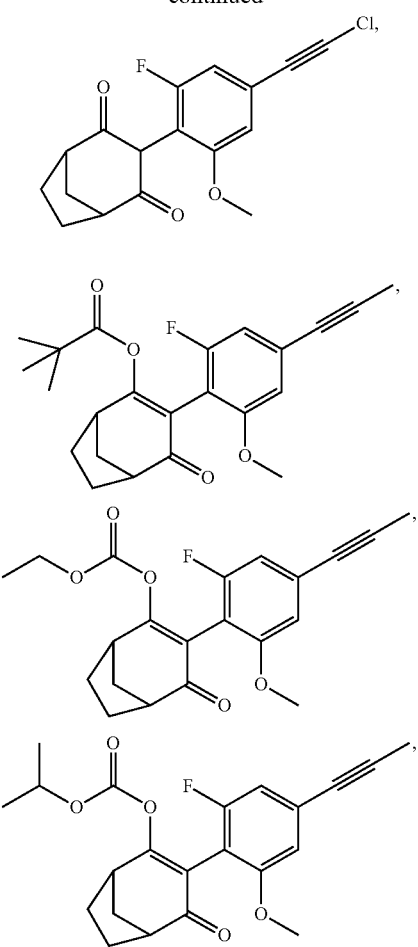
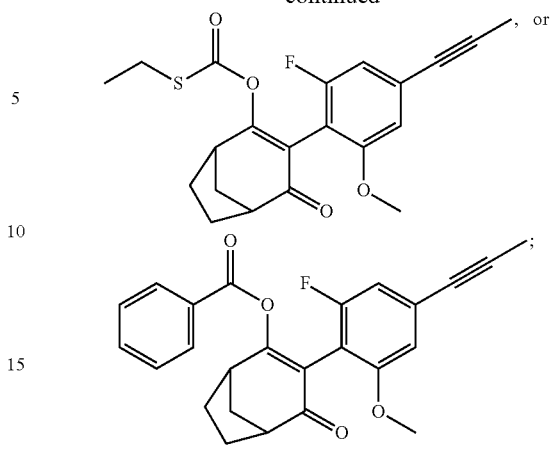

in each case optionally present as an agrochemically acceptable salt thereof.

20. A herbicidal composition which comprises:
(i) a compound of formula (I), as defined in claim 1, and
(ii) an agrochemically acceptable carrier, diluent and/or solvent; and
(iii) optionally one or more further herbicides and/or optionally a safener.

21. A method of controlling grassy monocotyledonous weeds in crops of useful plants, comprising applying a compound of formula (I), as defined in claim 1, or a herbicidal composition according to claim 20, to the weeds and/or to the plants and/or to the locus thereof.

22. A method as claimed in claim 21, wherein the crops of useful plants comprise wheat, barley, rye, triticale, sugarcane, soybean, peanut, pulse crops, cotton, rape, sunflower, linseed, sugarbeet, fodder beet, potato, and/or dicotyledonous vegetables.

* * * * *